(12) United States Patent
Womble et al.

(10) Patent No.: US 8,932,360 B2
(45) Date of Patent: Jan. 13, 2015

(54) IMPLANTS FOR SPINAL THERAPY

(71) Applicant: Baxano Surgical, Inc., Raleigh, NC (US)

(72) Inventors: Thomas Matthew Womble, Leland, NC (US); Leighton LaPierre, Wilmington, MA (US)

(73) Assignee: Baxano Surgical, Inc., Raleigh, NC (US)

(*) Notice: Subject to any disclaimer, the term of this patent is extended or adjusted under 35 U.S.C. 154(b) by 0 days.

(21) Appl. No.: 14/152,883

(22) Filed: Jan. 10, 2014

(65) Prior Publication Data

US 2014/0128979 A1   May 8, 2014

Related U.S. Application Data

(63) Continuation of application No. 13/658,426, filed on Oct. 23, 2012, now Pat. No. 8,795,167.

(60) Provisional application No. 61/629,228, filed on Nov. 15, 2011.

(51) Int. Cl.

| A61F 2/44 | (2006.01) |
|---|---|
| A61F 2/46 | (2006.01) |
| A61B 17/064 | (2006.01) |
| A61B 17/068 | (2006.01) |
| A61B 1/32 | (2006.01) |
| A61B 17/70 | (2006.01) |

(52) U.S. Cl.
CPC ............ *A61F 2/4611* (2013.01); *A61B 17/0642* (2013.01); *A61B 17/0682* (2013.01); *A61B 1/32* (2013.01); *A61B 17/70* (2013.01); *A61F 2/4455* (2013.01); *A61B 2017/0641* (2013.01)
USPC ........................................................ 623/17.16

(58) Field of Classification Search
USPC ...................................................... 623/17.16
See application file for complete search history.

(56) References Cited

U.S. PATENT DOCUMENTS

| 5,860,973 | A | 1/1999 | Michelson |
|---|---|---|---|
| 6,206,924 | B1 | 3/2001 | Timm |
| 6,454,805 | B1 | 9/2002 | Baccelli |
| 6,468,311 | B2 | 10/2002 | Boyd et al. |
| 6,491,724 | B1 | 12/2002 | Ferree |
| 6,558,424 | B2 | 5/2003 | Thalgott |
| 6,740,091 | B2 | 5/2004 | Kohrs |

(Continued)

OTHER PUBLICATIONS

International Search Report and Written Opinion for PCT/US2012/064465 dated Feb. 5, 2013 for implant claims corresponding to a portion of the present application. (10 pages).

*Primary Examiner* — Sameh Boles
(74) *Attorney, Agent, or Firm* — Kevin E Flynn; Flynn IP Law

(57) ABSTRACT

Minimally invasive surgical techniques including techniques and implants for provision of therapy to a spine from a lateral approach. Implants that may be used with other approaches to the spine are disclosed. Minimally invasive surgical techniques using one or more extended retractors to create an extended access route such as the non-limiting example of lateral access to the spine. Minimally invasive surgical techniques using internal retractors that may be reversibly expanded with a removable retractor inserter to create an extended access route. A linkage jack to expand a set of two or more extended retractors to create an extended access route.

8 Claims, 42 Drawing Sheets

(56) References Cited

U.S. PATENT DOCUMENTS

| | | |
|---|---|---|
| 6,743,255 B2 | 6/2004 | Ferree |
| 7,044,972 B2 | 5/2006 | Mathys, Jr. |
| 7,063,725 B2 | 6/2006 | Foley |
| 7,066,961 B2 | 6/2006 | Michelson |
| 7,112,224 B2 | 9/2006 | Liu |
| 7,135,043 B2 | 11/2006 | Nakahara |
| 7,137,997 B2 | 11/2006 | Paul |
| 7,169,183 B2 | 1/2007 | Liu |
| 7,491,241 B2 | 2/2009 | Errico |
| 7,550,008 B2 | 6/2009 | Ralph |
| 7,588,599 B2 | 9/2009 | Sweeney |
| 7,695,513 B2 | 4/2010 | Zucherman |
| 7,749,269 B2 | 7/2010 | Peterman |
| 7,763,078 B2 | 7/2010 | Peterman |
| 7,776,095 B2 | 8/2010 | Peterman |
| 7,799,081 B2 | 9/2010 | McKinley |
| 7,815,682 B1 | 10/2010 | Peterson |
| 7,918,891 B1 * | 4/2011 | Curran et al. .............. 623/17.16 |
| 2003/0135275 A1 | 7/2003 | Garcia |
| 2005/0125029 A1 | 6/2005 | Bernard |
| 2007/0067035 A1 | 3/2007 | Falahee |
| 2007/0093897 A1 | 4/2007 | Gerbec |
| 2007/0093898 A1 | 4/2007 | Schwab |
| 2007/0118220 A1 | 5/2007 | Liu |
| 2008/0015695 A1 | 1/2008 | Eckman |
| 2008/0071372 A1 | 3/2008 | Butler |
| 2008/0154377 A1 | 6/2008 | Voellmicke |
| 2008/0221695 A1 | 9/2008 | Jacofsky |
| 2008/0243255 A1 | 10/2008 | Butler |
| 2008/0294262 A1 | 11/2008 | Levieux |
| 2008/0306596 A1 | 12/2008 | Jones |
| 2009/0088765 A1 | 4/2009 | Butler |
| 2009/0099601 A1 | 4/2009 | Aferzon |
| 2009/0105824 A1 | 4/2009 | Jones |
| 2009/0198339 A1 | 8/2009 | Kleiner |
| 2009/0210062 A1 | 8/2009 | Thalgott |
| 2009/0222100 A1 | 9/2009 | Cipoletti |
| 2009/0299479 A1 | 12/2009 | Jones |
| 2009/0306715 A1 | 12/2009 | Jackson |
| 2010/0094422 A1 | 4/2010 | Hansell |
| 2010/0137988 A1 | 6/2010 | Markworth |
| 2010/0179594 A1 | 7/2010 | Theofilos |
| 2010/0204798 A1 | 8/2010 | Gerbec |
| 2011/0022090 A1 | 1/2011 | Gordon |
| 2011/0035007 A1 | 2/2011 | Patel |
| 2011/0106261 A1 | 5/2011 | Chin |
| 2011/0118840 A1 | 5/2011 | Huntsman |

* cited by examiner

500

FIG. 45
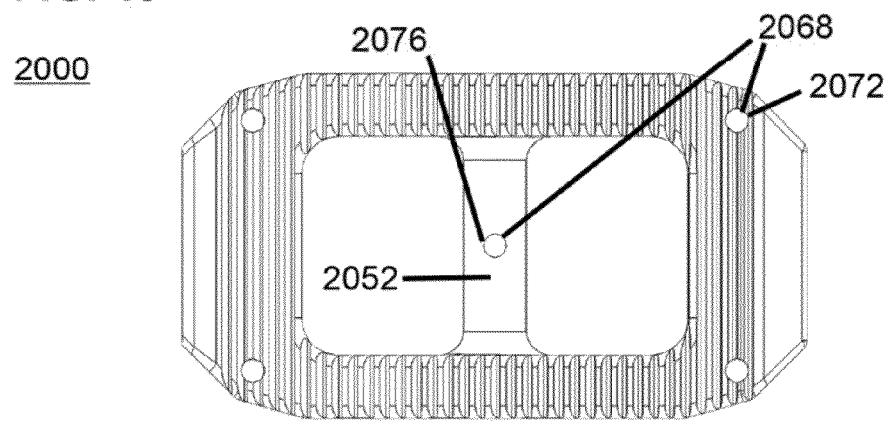
FIG. 46
FIG. 47
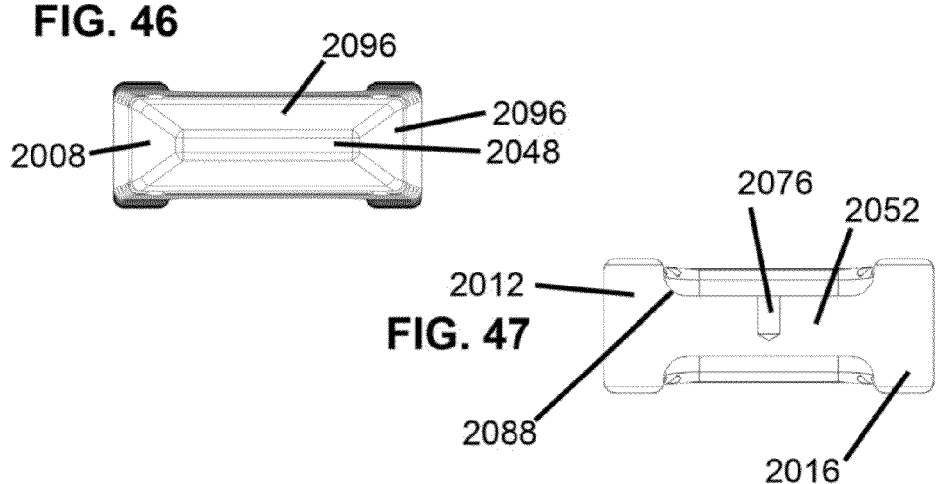
FIG. 48
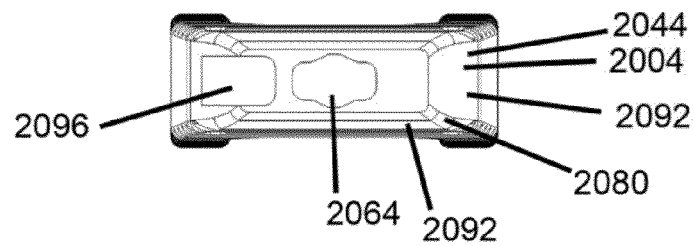

FIG. 52
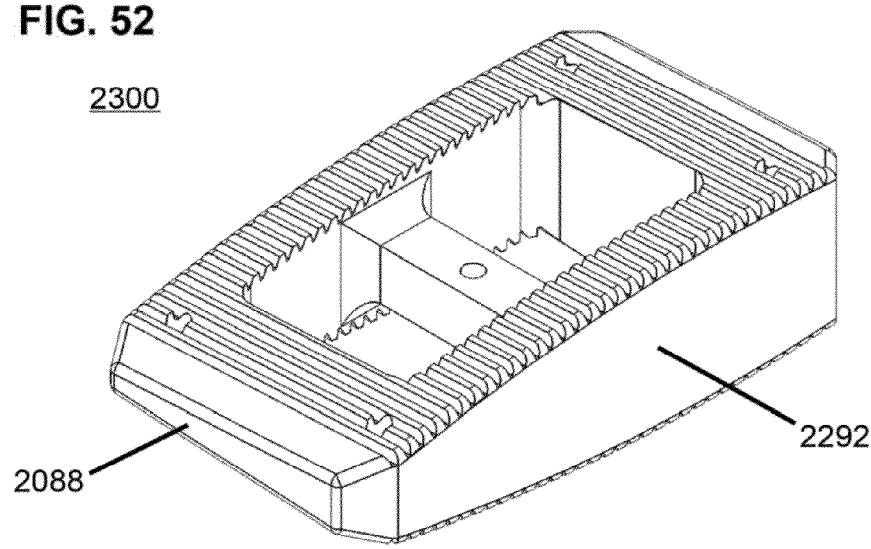
FIG. 53
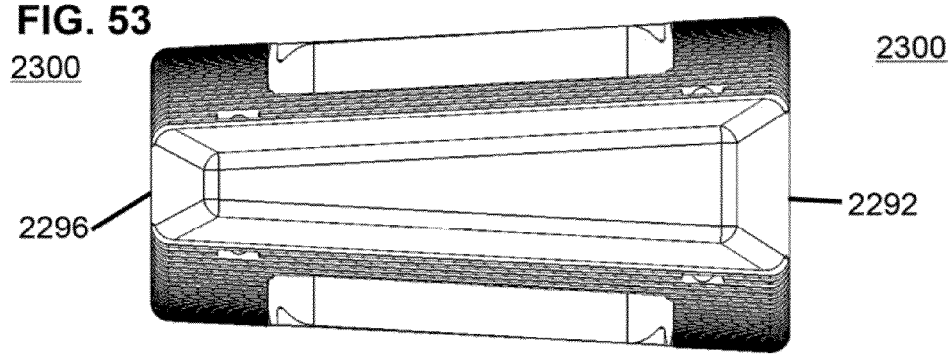
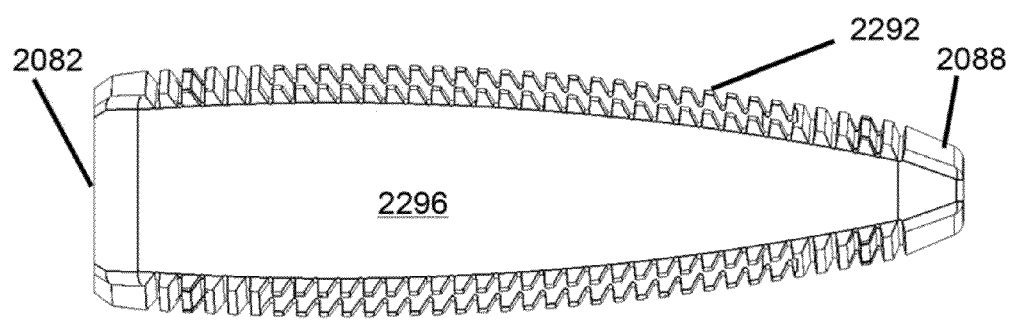
FIG. 54

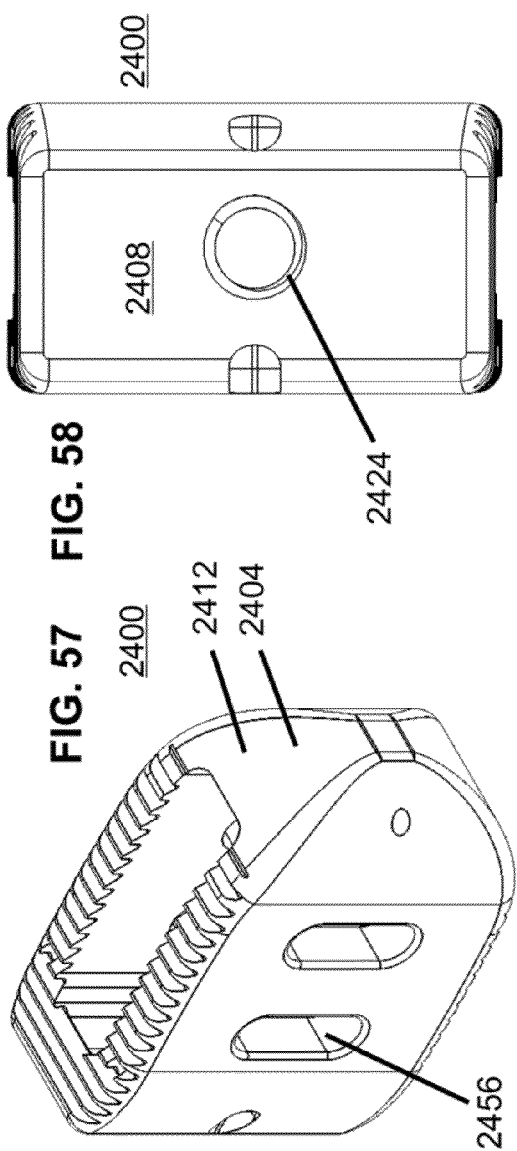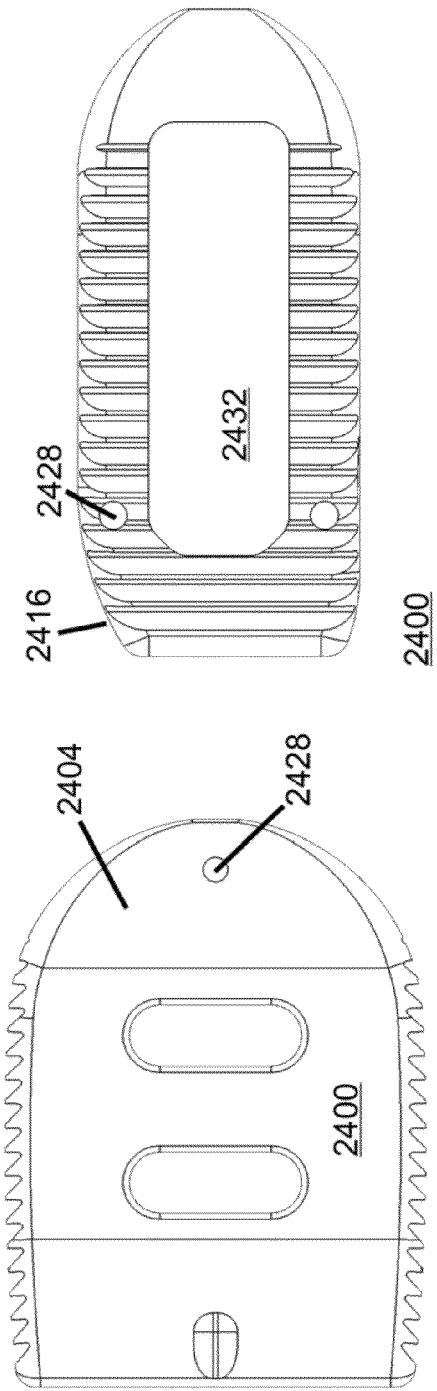

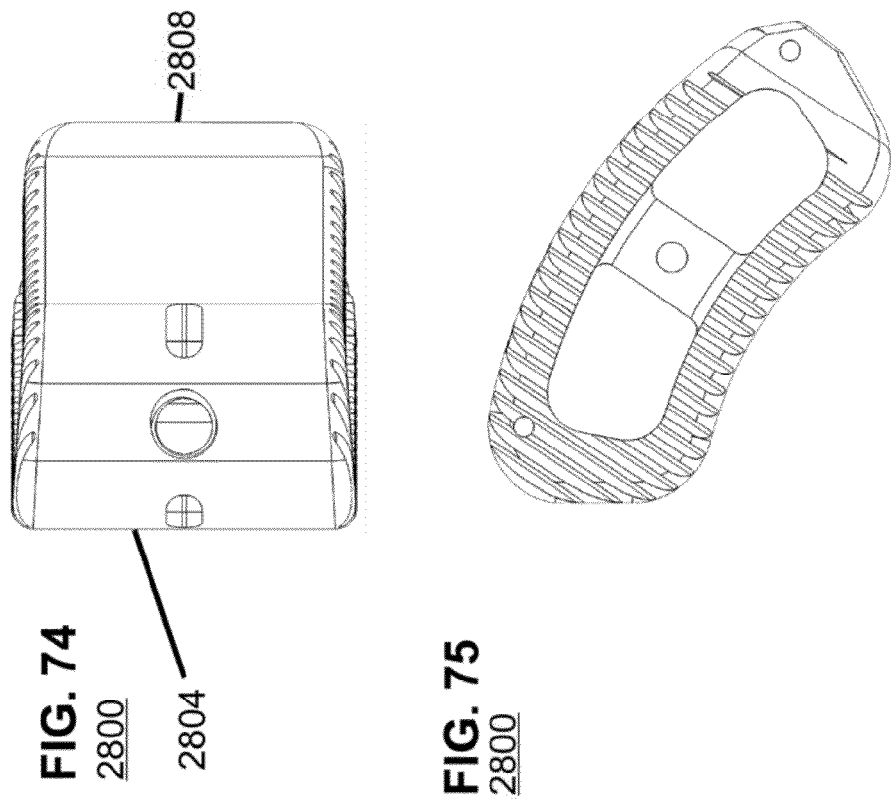
FIG. 74
2800          2804
FIG. 75
2800
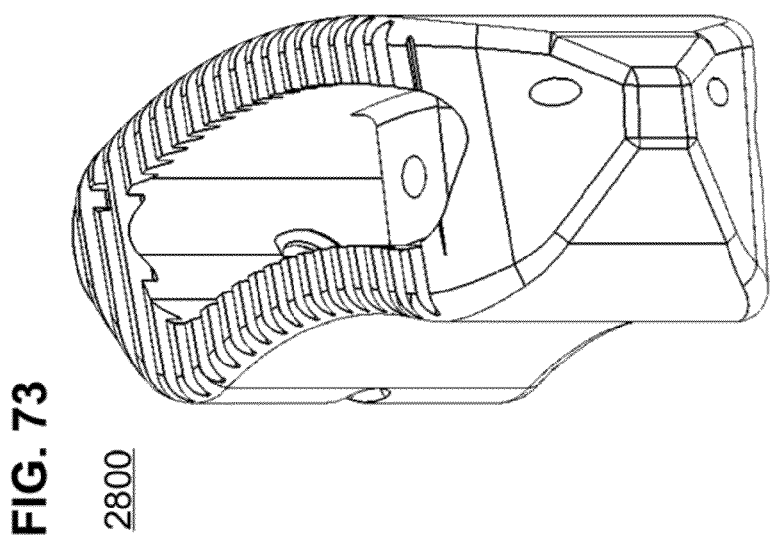
FIG. 73
2800

IMPLANTS FOR SPINAL THERAPY

This application is a continuation application of co-pending U.S. application Ser. No. 13/658,426, filed Oct. 23, 2012 for Spinal Therapy Lateral Approach Access Instruments and Implants and incorporates the '426 application by reference in its entirety. Through the '426 application, this application claims the benefit of U.S. Provisional Application No. 61/629,228, filed Nov. 15, 2011 for Spinal Interbody System Apparatus and Method and incorporates the '228 application by reference in its entirety.

While the '228 application has been incorporated by reference to provide additional detail it should be noted that this provisional was written at an earlier time and had a different focus from the present application. Thus, to the extent that the teachings or use of terminology differ in any of these incorporated applications from the present application, the present application controls.

BACKGROUND

Field of the Disclosure

This disclosure relates generally to minimally invasive surgical techniques including techniques and implants for provision of therapy to a spine from a lateral approach. Implants that may be used with other approaches to the spine are disclosed. Minimally invasive surgical techniques using one or more extended retractors to create an extended access route such as the non-limiting example of lateral access to the spine are disclosed.

GENERAL COMMENTS AND TERMINOLOGY

In the context of the present disclosure, as used herein the term "assembly" refers to implants, instruments and instruments systems which are configured to comprise multiple components, which may or may not be contiguous. It is further understood that individual components may themselves be configured as sub-assemblies, e.g., comprising a plurality of component materials, and that the formation of the components may involve intermediate processes or appliances.

It will also be understood that upon formation of assemblies from multiple components and deployment, individual components of the present disclosure may or may not remain as discernibly distinct. It will also be understood that, for convenience, system components may be packaged and provided either individually, or as in "kits," and either as reusable or disposable.

As used herein, the term "biocompatible" refers to an absence of chronic inflammation response or cytotoxicity when or if physiological tissues are in contact with, or exposed to (e.g., wear debris) the materials and devices of the present disclosure. In addition to biocompatibility, in another aspect of the present disclosure it is preferred that the materials comprising the instrument systems are sterilizable.

In one aspect of the present disclosure, certain components of the device assemblies and systems of the present disclosure are configured to comprise biocompatible materials and are able to withstand, without wear, multiple cycles/procedures without failing. It will be further understood that the length and dimensions of instruments and components described herein will depend in part on the target site selection of the treatment procedure and the physical characteristics of the patient, as well as the construction materials and intended functionality, as will be apparent to those of skill in the art In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

In the context of this discussion: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. Proximal is closer to the beginning of the channel and thus the surgeon; distal is further from the beginning of the channel and in use more distant from the surgeon. When referencing tools including cutters or other tools distal would be the end intended for insertion into the access channel and proximal refers to the other end, generally the end closer to the handle for the tool.

The sequence of operations (or steps) is not limited to the order presented in the claims or figures unless specifically indicated otherwise.

SUMMARY

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 45 is a top view of an implant.

FIG. 46 is a front view of an implant.

FIG. 47 shows a cross section of the implant from FIG. 42 taken through the midline of the cross bar.

FIG. 48 shows a view of the trailing end portion of the implant from FIG. 42.

FIG. 52 is a front perspective view of an oblique lordotic implant.

FIG. 53 is a front view of the oblique lordotic implant of FIG. 52.

FIG. 54 is a side front view of the oblique lordotic implant of FIG. 52.

FIG. 57 is a front perspective view of an implant.

FIG. 58 is a rear view of the implant in FIG. 57.

FIG. 59 is a side view of the implant in FIG. 57.

FIG. 60 is a top view of the implant in FIG. 57.

Figures 69, 70, 71, 72:
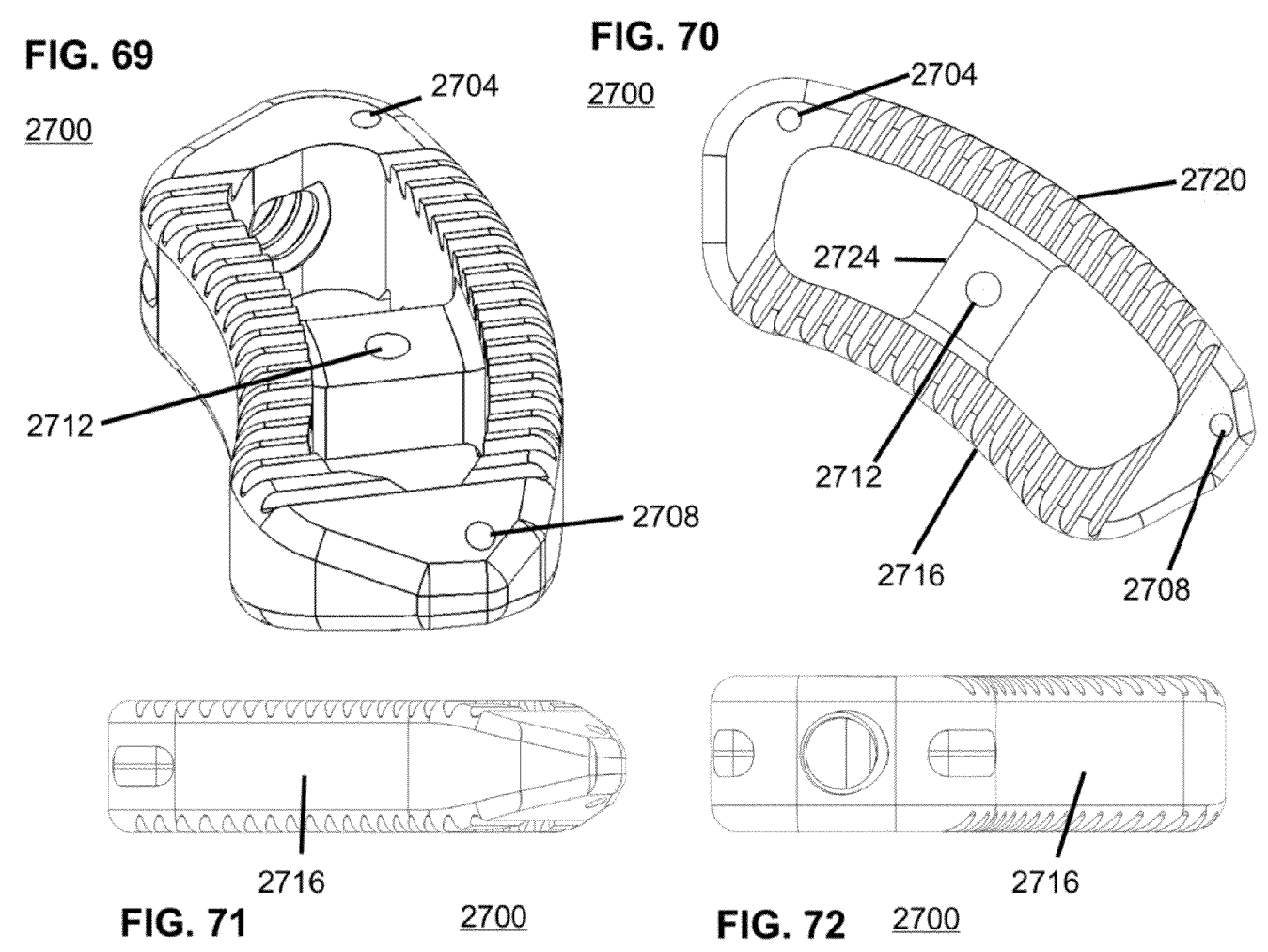

FIG. 69 is a front perspective view of an implant.

FIG. 70 is a top view of the implant of FIG. 69.

FIG. 71 is a side view of the implant of FIG. 69.

FIG. 72 is a rear view of the implant of FIG. 69.

FIG. 73 is a front perspective view of an implant.

FIG. 74 is a rear view of the implant from FIG. 73.

FIG. 75 is a top view of the implant from FIG. 73.

DETAILED DESCRIPTION

Figure 1:
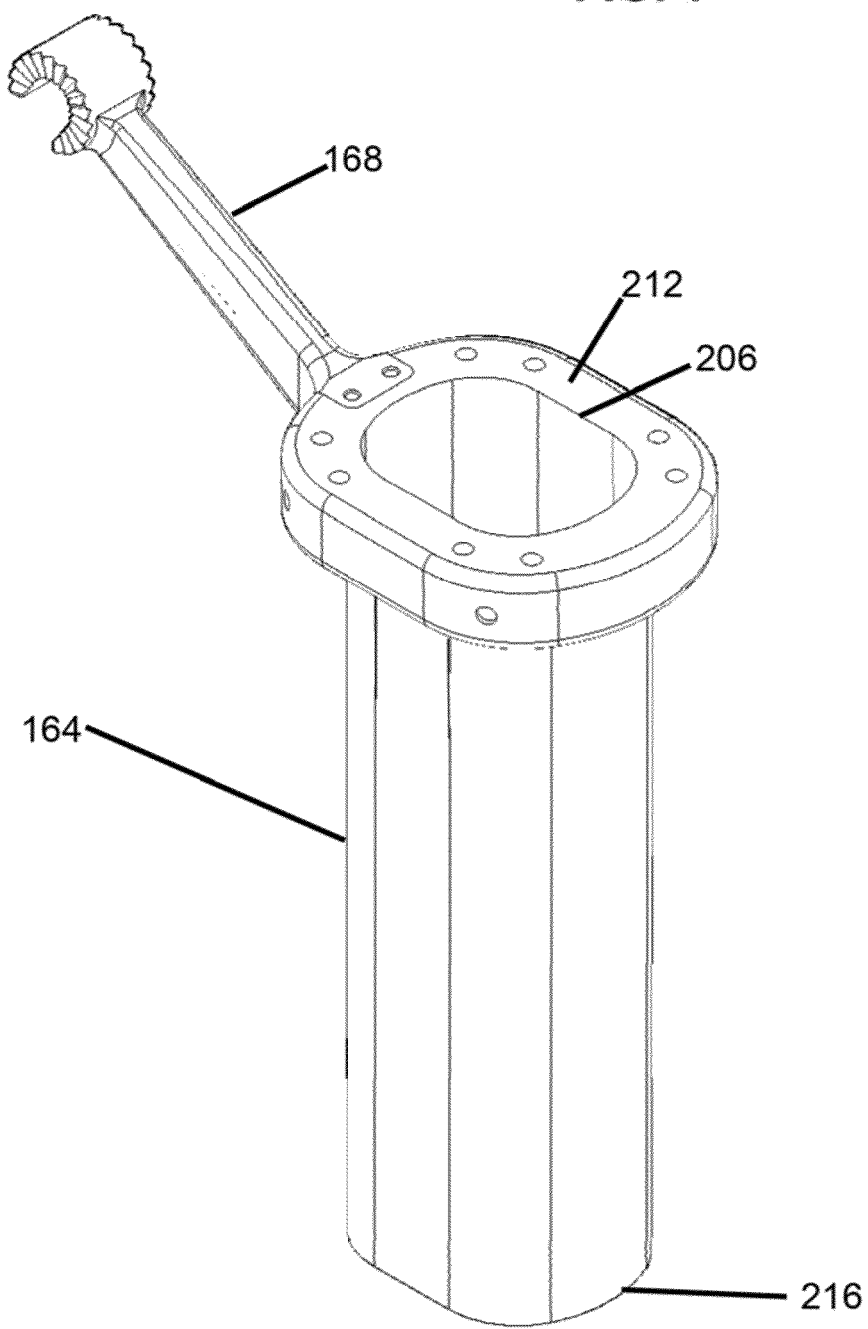
FIG. 1 is a top perspective view of a channel retractor.

The present application has a range of teachings that may be used to advantage in a number of settings. However, to provide these teachings with clarity, it is useful to describe one use of many of the teachings in great detail. The use described below is to access a lateral portion of a human spine using a lateral approach in order to provide therapy such as a fusion procedure to a vertebral motion segment. This process may be broken down to a natural sequence of:
  Positioning the patient,
  Creating an access channel to the psoas muscle
  Creating an opening through the psoas muscle
  Enlarging an access channel through the psoas muscle.

Preparing the disc space

Delivering an implant which may include fusion promoting materials.

Closing the access path.

Psoas Muscle.

The psoas muscle is a major muscle in the human body used to stabilize the base of the spine. The psoas muscle is involved in hip flexion and rotation. The psoas muscle runs on both lateral sides of the lumbar spine. The psoas muscle is of interest for spine surgery in that this tough muscle must be traversed to access lumbar discs from a lateral approach.

Positioning the Patient.

Those of skill in the art are familiar with various techniques for positioning a patient to facilitate access to a spinal disc space from a lateral approach. This knowledge includes making adjustments as needed to provide access around the iliac crest for lateral access to the lumbo-sacral spine. Thus, this description will be brief and should be considered exemplary rather than limiting to the teachings of the present disclosure.

A patient may be positioned in a lateral decubitus position on a radiolucent breaking table. The patient may be stabilized and secured to the table with surgical tape:

A) just below the iliac crest

B) over the thoracic region;

C) from the iliac crest to the knee, then secured to the table; and

D) from the table to the knee, past the ankle, then secured back to the table.

Placing the table break at the iliac crest may work well when targeting the L3/L4 or L4/L5 disc spaces. When targeting the L1/L2 or the L2/L3 disc spaces it may be helpful to position the patient so that the table break is cephalad of the iliac crest. After positioning, a true Anterior/Posterior (A/P) image may be obtained of the targeted disc using a C-arm imaging device (not shown). Likewise a true lateral image may be obtained using the C-arm imaging device. A line in the anterior/posterior direction may be drawn on the patient to represent the midline of the targeted disc. Additional lines may be added to represent the front, back, and midline of the disc space in the lateral direction.

After conventional draping and preparation of the surgical site, at table mounted retractor arm (not shown) may be mounted to the table for use later in the process.

Access to Psoas.

Make an anterior-to-posterior incision over the center marking of the disc space. This incision may be 35 to 40 millimeters in length for some patients. The incision may be transverse, vertical, or oblique depending on preference.

Using finger or blunt dissection, open the incision down to fascia over the external oblique muscles. Incise fascia in line with the muscle fibers. Continue blunt or finger dissection through the muscle layers into the retroperitoneal space to the psoas muscle. After blunt or finger dissection has made a pathway to the psoas muscle, the access channel may be enlarged through conventional means such as a sequence of dilation tubes of increasing diameter and decreasing length. The term enlarge is meant to include the various processes known in the art to increase the volume of an opening. This would include dilation, dissection, retraction, or combinations thereof, and analogous actions.

Depth indications on the outermost dilator may be used to select a channel retractor. For example the first outermost dilator has depth markings for 100 millimeters, 120 millimeters and 140 millimeters on one side along the longitudinal shaft of the outermost dilator. The surgeon notes the value of the marker closest to the patient's skin and selects a corresponding channel retractor (discussed below) to insert over the outer surface of the outermost dilator. The channel retractor is advanced distally down to the psoas muscle and then secured with the table mounted retractor arm with a stabilization arm. All of the tissue dilators are removed and a lateral fluoroscopic image is obtained to confirm placement of the channel retractor is centered over the targeted disc space. If the channel retractor is not centered, adjustments are made so that the channel retractor is positioned directly over the targeted disc.

FIG. 1 shows an example of a channel retractor 164. Note that the channel retractor 164 may have a substantially uniform cross section (as taken with respect to the longitudinal axis). The cross section of the channel retractor 164 may be round (uniform radius), elliptical, square, oblong, or other shapes. In many instances the cross section will have rounded surfaces even for shapes such as a square or rectangle that is longer than it is wide. The cross section of the channel retractor 164 in FIG. 1 may be described as a rounded rectangle as it has a pair of curved ends separated by straight walls. The channel retractor 164 is sometimes called a tubular retractor as it comprises a lumen that is an opening at a proximal end 212 extending throughout its length to an opening at a distal end 216, the channel retractor 164 thus having an inner perimeter 206. The channel retractor 164 may have a stabilizer arm 168 for use to connect to a table mounted retractor arm.

Creating an Opening in the Psoas Muscle.

To prepare for work on the psoas muscle, it may be useful to add lighting. One way to add lighting is to plug one end of a fiber optic cable into a light source in accordance with manufacturer's instructions. The other end of the fiber optic cable may be attached to a stadium mount light. The stadium mount light may then be attached to the proximal end of the channel retractor 164 so that the outer surface of the psoas muscle near the distal end of the channel retractor 164 is well lit. The proximal end of the channel retractor 164 may be adapted to allow the surgeon a choice of several locations for mounting the stadium mount light to the channel retractor 164.

As nerves are in the psoas muscle and care is taken to avoid damaging the nerves, those of skill in the art understand the process of neuromonitoring to locate the positioning of the nerves. As neuromonitoring is not the focus of the present application, details on the process of neuromonitoring are not included here.

Figure 2:
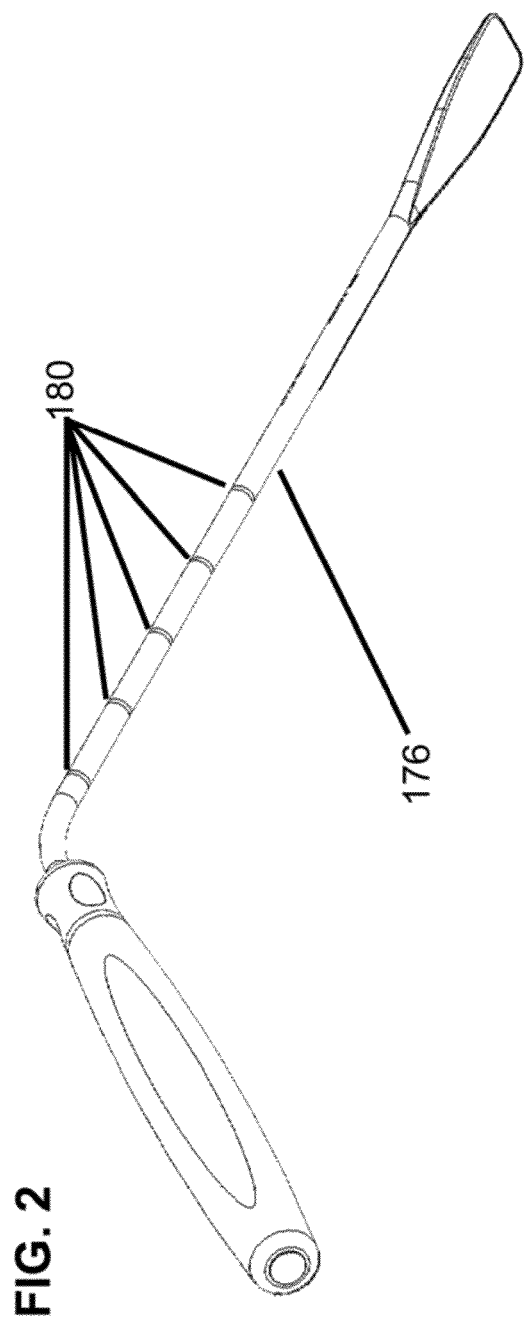
FIG. 2 is an angled Cobb dissector.

The top surface of the psoas muscle is split between the muscle fibers typically using a Penfield dissector or a Cobb dissector. Some surgeons may prefer a straight dissector, and some may prefer an angled dissector. FIG. 2 shows an angled Cobb dissector 176 that may be used. The angled Cobb dissector 176 has a set of insertion depth markings 180 that may be used as an input by the surgeon to select components of the appropriate length for secondary retraction steps.

After the psoas muscle is split, some surgeons will choose to insert a 90 degree nerve retractor down the side of the dissector used to maintain the split in the psoas muscle.

A guide pin (not shown) may be inserted along the nerve retractor (or dissector) through the split in the psoas muscle into the interior of the targeted disc space. The distal end of the guide pin may be inserted five to ten millimeters into the disc space. Once the guide pin is positioned, the nerve retractor may be removed from the incision.

A lateral fluoroscopy image may be taken to confirm that the guide pin is in the anterior/posterior center of the disc space. If the guide pin is properly positioned, an A/P fluoroscopic view may be used to confirm that the channel retractor 164 is centered over the guide pin. Once the channel retractor 164 position has been adjusted to be centered over the centered guide pin, the guide pin may be removed.

While it is thought that work on the psoas muscle is best done after the channel retractor 164 is placed over the series of dilators, one of skill in the art will recognize that work to create the initial opening in the psoas muscle could happen before placing the channel retractor 164 such as through use of tools that are inserted through the outermost dilator (after one, some or all of the inner dilators are removed).

Creating an Access Channel in the Psoas Muscle.

Enlarging the small opening created by the initial opening in the tough fibrous psoas muscle is challenging. Once the channel retractor 164 is properly aligned and provides a working channel from outside the patient to the edge of the psoas muscle. However, sufficient force needs to be applied to expand the psoas muscle and then the enlarged opening in the psoas muscle should be maintained as a working channel to the disc space to allow for the surgical procedure on the disc, such as a fusion procedure.

The present disclosure sets forth three different categories of solutions for extending the working channel beyond the channel retractor 164 and through a dense tissue such as the psoas muscle. The retraction of tissue up to the psoas muscle may be called primary retraction, and the retraction of tissue through the psoas muscle to the spine may be called secondary retraction. The first family of solutions may be called tube in a tube solutions. The second family of solutions may be called internal retractor insertion. The third family may be called linkage jacks.

Tube in a Tube.

Figure 3:
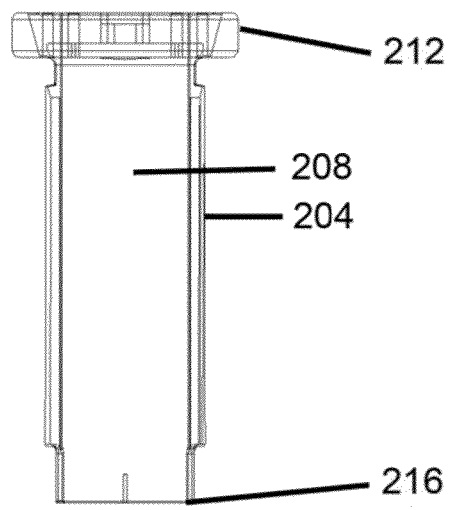
FIG. 3 is a cross section of a channel retractor.

FIG. 3 to FIG. 7 illustrate the concept of a tube in a tube secondary retraction system. In FIG. 3, a cross section of a channel retractor 204 is shown. As will be evident from looking at this set of drawings, this channel retractor 204 has a circular rather than rounded rectangular cross section as shown above. The channel retractor 204 has a closed inner perimeter that defines a working channel 208 through a first tissue from the proximal end 212 outside the patient to a distal end 216 placed adjacent to the edge of a second tissue such as the psoas muscle. As this process may be used in situations where the psoas muscle is not the second tissue, the concept of first and second tissue can be summarized that second tissue is tissue beyond the distal end of the channel retractor that is spread apart or simply maintained apart and the first tissue is the tissue that contains the channel retractor.

Figure 4:
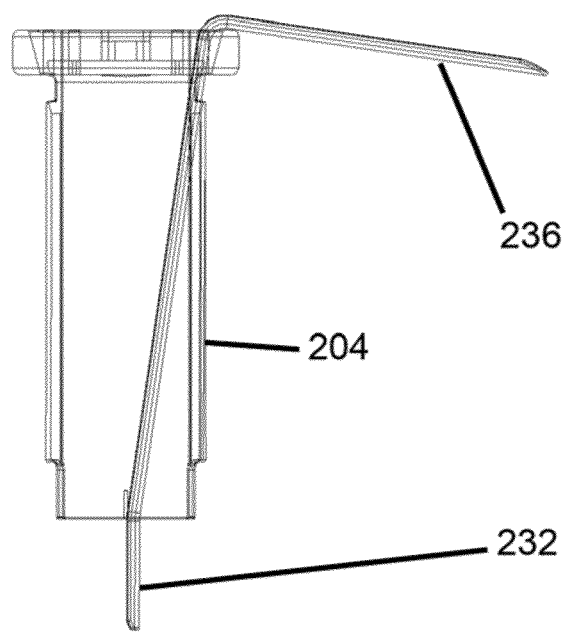
FIG. 4 is a cross section of a channel retractor with an extended retractor.

FIG. 4 shows the cross section of FIG. 3 after the distal end portion 232 of a first extended retractor 236 is moved through the channel retractor 204 and into the opening made in the psoas muscle as described above. The first extended retractor 236 may be made from a material such as 17-4 stainless steel, aluminum, or carbon fiber composite.

Figure 5:
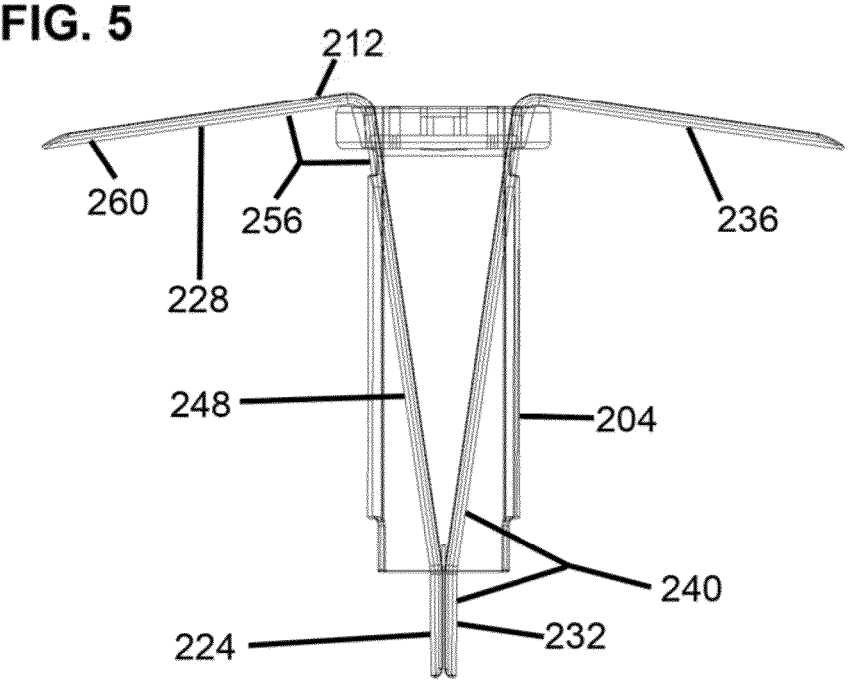
FIG. 5 is a cross section of a channel retractor with two extended retractors.

FIG. 5 shows the cross section of FIG. 4 after a distal end portion 224 of a second extended retractor 228 is moved through the channel retractor 204 and into the opening made in the psoas muscle. Notice that the first extended retractor 236 and second extended retractor 228 each have a first angle 240 between the distal end portion 224, 232 for insertion into the psoas muscle and the intermediate portion 248 for traversing the channel retractor 204. The intermediate portion 248 may be called the channel retractor portion. This obtuse first angle 240 allows the two distal end portions 224 and 232 to be substantially aligned for placement adjacent to one another in an opening in the psoas muscle. The first extended retractor 236 and the second extended retractor 228 each have a second angle 256 of approximately ninety degrees for placement at the proximal end 212 of the channel retractor 204 to allow a handle portion 260 for the first extended retractor 236 and second extended retractor 228 to be out of the way of the surgeon, so the surgeon can easily have direct visualization of the psoas muscle.

One of skill in the art will appreciate that rather than moving the first extended retractor 236, then moving the second extended retractor 228 at different times, at least some of the movement could be to move both extended retractors towards the opening in the second tissue for a concurrent period of time.

Figure 6:
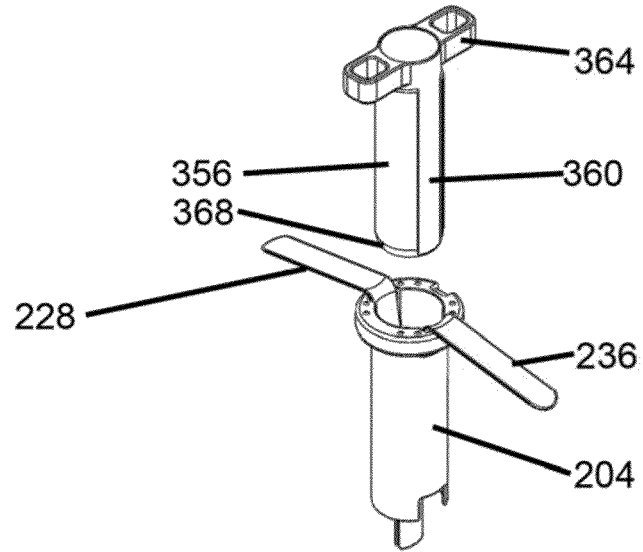
FIG. 6 shows an inner sleeve in proximity to a channel retractor with extended retractors.

FIG. 6 illustrates inserting an inner sleeve 356 into the channel retractor 204 to force the first extended retractor 236 and second extended retractor 228 to substantially opposite sidewall portions of the inner perimeter 206 of the channel retractor 204 to gradually and controllably spread the opening in the psoas muscle. In the most basic form (not shown here) the inner sleeve could be an appropriately sized hollow cylinder.

Note that the inner sleeve 356 has a retractor receiving indentation 360 that is visible in this view. A corresponding retractor receiving indentation is on the opposite side. The distal end 368 of the inner sleeve 356 may include a bevel 368.

Figure 7:
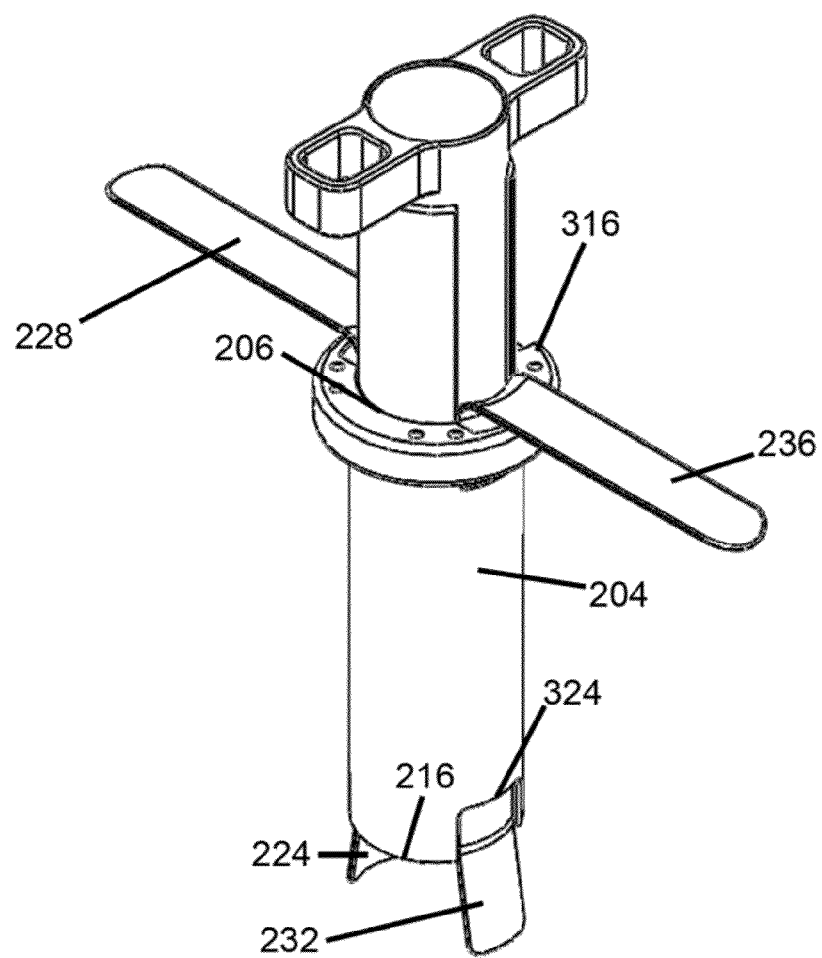
FIG. 7 is a top perspective view during insertion of the inner sleeve to form an assembly.

FIG. 7 is a top perspective view during insertion of the inner sleeve 356 to form an assembly with portions of the first extended retractor 236 and second extended retractor 228 sandwiched between the inner sleeve 356 and the inner perimeter 206 of the channel retractor 204. Note that the first extended retractor 236 and the second extended retractor 228 may be inserted to different depths. For example, the extended retractor placed on the anterior side of the opening in the psoas muscle may need to extend further distally than the extended retractor placed on the posterior side of the opening in the psoas muscle, due to anatomical differences of the spine.

One of skill in the art will appreciate that an inner sleeve may be sized to push the first extended retractor and the second extended retractor outward from the centerline of the channel retractor, but not far enough to move both the extended retractors against the inner perimeter of the channel retractor. Some surgeons may prefer a smaller expansion of the second tissue and thus may not opt to fully expand the tissue. Conversely, a surgeon may opt for an initial partial expansion followed by a second expansion to push the extended retractors all the way to the inner perimeter of the channel retractor.

Notches 324 in the distal end 216 of the channel retractor 204 allow the distal portions 224 and 232 of the extended retractors 228 and 236 to extend beyond the inner perimeter 206 of the channel retractor 204 when the extended retractors 228 and 236 are positioned elevated relative to a proximal face 316 of channel retractor 204.

Ring Clip.

Figure 8:
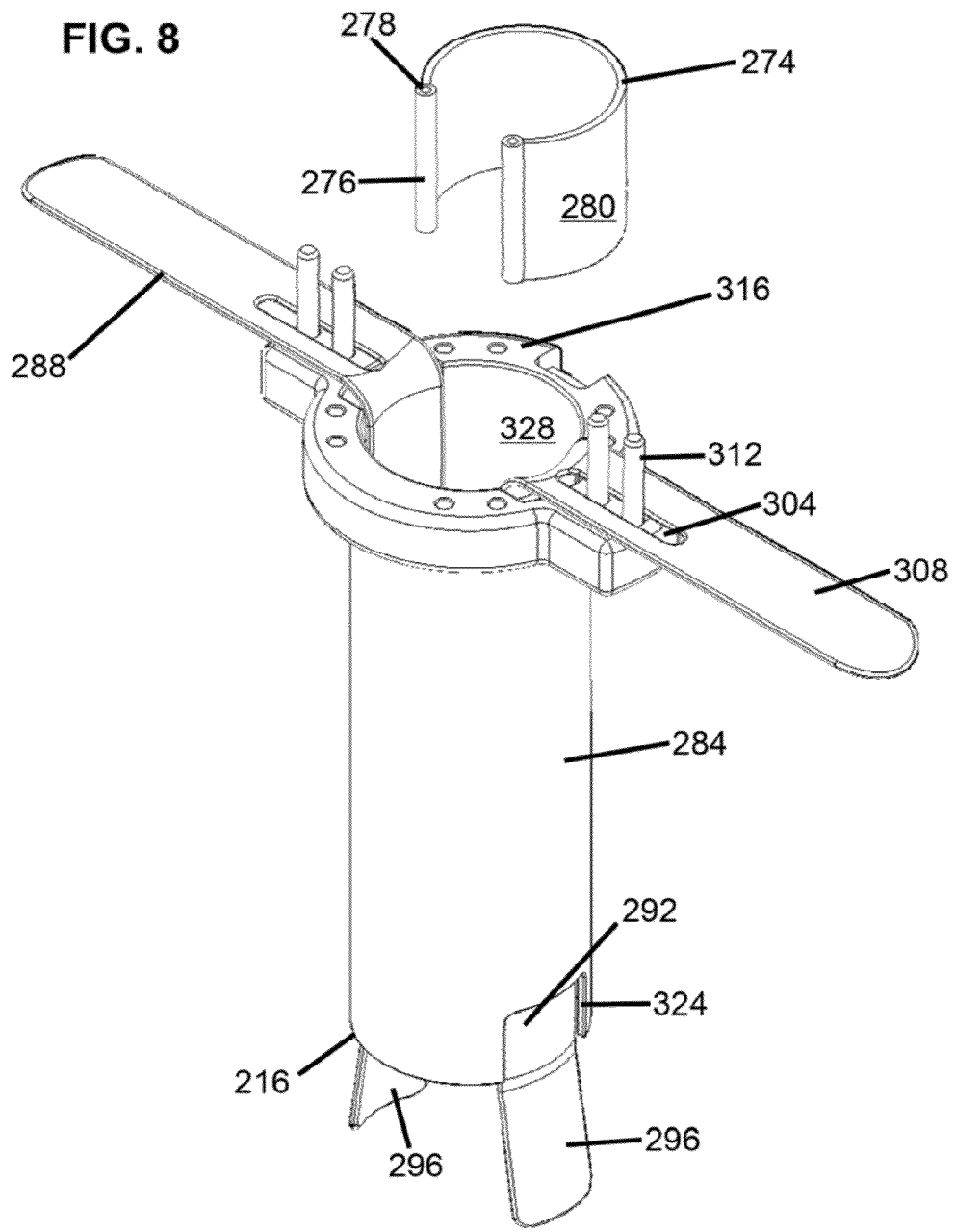
FIG. 8 is a top and side perspective view of an assembly using a ring clip 280.

FIG. 8 introduces some alternatives. As an alternative to an inner sleeve 270 that is a cylinder (having a closed perimeter around at least part of the cross sections), one may use a ring clip 280 which does not have a closed perimeter around any of the cross sections. Another way of saying does not have a closed perimeter is to say that it has an open perimeter rather than a closed perimeter.

FIG. 8 is a top and side perspective view of an assembly using a ring clip 280. The ring clip 280 used with this assembly is already within the interior of channel retractor 284 and that ring clip 280 cannot be seen from this view point. In order to facilitate the discussion of the hidden ring clip 280, a second ring clip 280 is shown in FIG. 8 near the proximal end of channel retractor 284. This second ring clip 280 is present just for discussion and is not part of the assembly with ring clip 280.

A first extended retractor 288 and a second extended retractor 292 are shown held against the inner perimeter 328 of the channel retractor 284 by the ring clip 280 within the channel retractor 284 (this ring clip is not visible in this view). The first extended retractor 288 and the second extended retractor 292 have slots 304 in their handles 308. The slots 304 in the handles 308 allow the handle 308 to be partially constrained by one or more vertical protrusions 312 (such as dowel pins) that extend upward from the proximal face 316 of the channel retractor 284. The protrusion/slot interaction allows the first extended retractor 288 and the second extended retractor 292 very limited movement around the perimeter of the channel retractor 284. However, the protrusion/slot interaction allows the first extended retractor 288 or the second extended retractor 292 to be moved proximally should one or both extended retractors need to be inserted less than the full amount, thus preserving a range of movement along the proximal/distal direction to alter an amount of extension of the distal end of the extended retractor beyond the distal end of the channel retractor 284. Notches 324 in the distal end 216 of the channel retractor 284 allow the distal portions 296 of the extended retractors 288 and 292 to extend beyond the inner diameter 328 of the channel retractor 284 when a handle 308 is positioned elevated relative to the proximal face 316 of channel retractor 284.

The proximal edge 274 of the open ends 276 of the ring clip 280 have apertures 278 which are configured to enable engagement with or grasping by a ring clip engagement tool (not shown) which can be used to compress the ring clip 280 in order to insert or remove the ring clip 280 from the channel retractor 284.

The ring clip 280 resting state at a predetermined diameter and material properties and dimensions determine the spring characteristics of the ring clip. The ring clip 280 may be fabricated, for example, from a shape memory alloy such as Nitinol™ or a stainless steel with spring-like characteristics. The contact surface between the exterior surface of the ring clip 280 and the inner surfaces of the extended retractors 288 and 292 are preferably surface-roughened, such as by coating or bead blast, or have teeth or pawls or ridges to maintain engagement between the ring clip 280 and the extended retractors 288, 292. Different diameters of ring clips 280 may be used to control the amount of muscle retraction by variation in the amount of opening of the extended retractors 288 and 292. Thus, depending on the ring clip selected the extended retractors 288, 292 may not be pushed up against the inner perimeter of the channel retractor 284.

Figure 9:
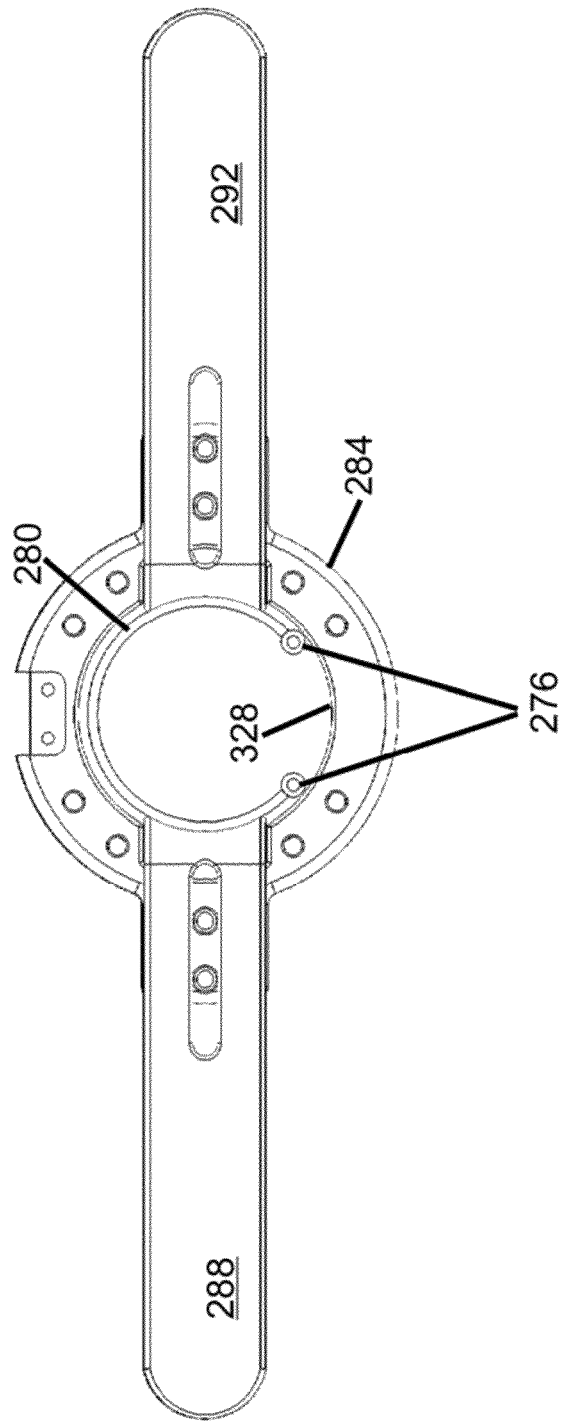
FIG. 9 is a top view of the assembly from FIG. 8 without the extra ring clip.

FIG. 9 is a top view of the assembly from FIG. 8 without the extra ring clip 280. Thus, a ring clip 280 is shown pressing outward on the first extended retractor 288 and the second extended retractor 292 to push extended retractors 288, 292 against the inner perimeter 328 of the channel retractor 284. Notice that the open ends 276 of the ring clip 280 are positioned away from either extended retractor 288 and 292.

A ring clip tool (not shown), configured similarly to a double jointed or double action pliers, may be used to engage or grasp the open ends 276 of the ring clip 280. When the ring clip tool is squeezed, squeezing causes the open ends 276 of the ring clip 280 to come together, effectively reducing the diameter of the ring clip 280. The ring clip 280 in its compressed state is then advanced distally within the channel retractor 284 and then the ring clip tool can be released. The spring force from the ring clip 280 as the released ring clip 280 expands outward pushes on the extended retractors 288, 292 and consequently pushes the distal portions 296 of the extended retractors outward.

One of skill in the art will recognize that a series of ring clips may be used so that an initial ring clip pushes the extended retractors outward but does not press the extended retractors firmly against the inner perimeter of the channel retractor. A second ring clip could be used to cause additional movement of the distal ends of the extended retractor. Likewise, if the psoas muscle resists expansion of the initial opening more than expected, a ring clip with greater spring force may be used.

One of skill in the art will recognize that when using a ring clip that both the distal end of the inner sleeve and the proximal end of the inner sleeve are inserted into the channel retractor to cause the distal portions of the first extended retractor and the second extended retractor to remain separated from the longitudinal centerline of the channel retractor. While many inner sleeves discussed in this disclosure have a proximal end that extends out the proximal end of the channel retractor, this is not required in order to use at least some of the many teachings of the present disclosure. An inner sleeve other than a ring clip such as a C-shaped inner sleeve, or a closed perimeter inner sleeve (such as a hollow cylinder) could be used with an appropriate insertion/removal tools where the both the distal end of the inner sleeve and the proximal end of the inner sleeve are inserted into the channel retractor to cause the distal portions of the first extended retractor and the second extended retractor to remain separated from the longitudinal centerline of the channel retractor.

While FIG. 8 and FIG. 9 show a pair of protrusions 312 on each side of the proximal face 316 of the channel retractor 284, one of skill in the art will recognize that a fin (not shown) could be used in place of the pair of protrusions 312. As the length of the slot 304 is longer than the distance from the inner edge of the innermost of the two protrusions 312 to the outer edge of the outermost protrusion 312, the handle 308 has some ability to move in the radial direction. As noted above, the handle 308 also has an ability to move in the proximal/distal direction until stopped by the proximal face 316 of the channel retractor 284. However as the diameters of the protrusions 312 are not much less than the width of the slot 304 in the handle 308 so the handle 308 is substantially constrained from movement around the perimeter of the channel retractor 284. This limitation impacts the distal portions 296 of the extended retractors 288, 292 and these distal portions 296 are thus maintained substantially across from each other.

Figure 10:
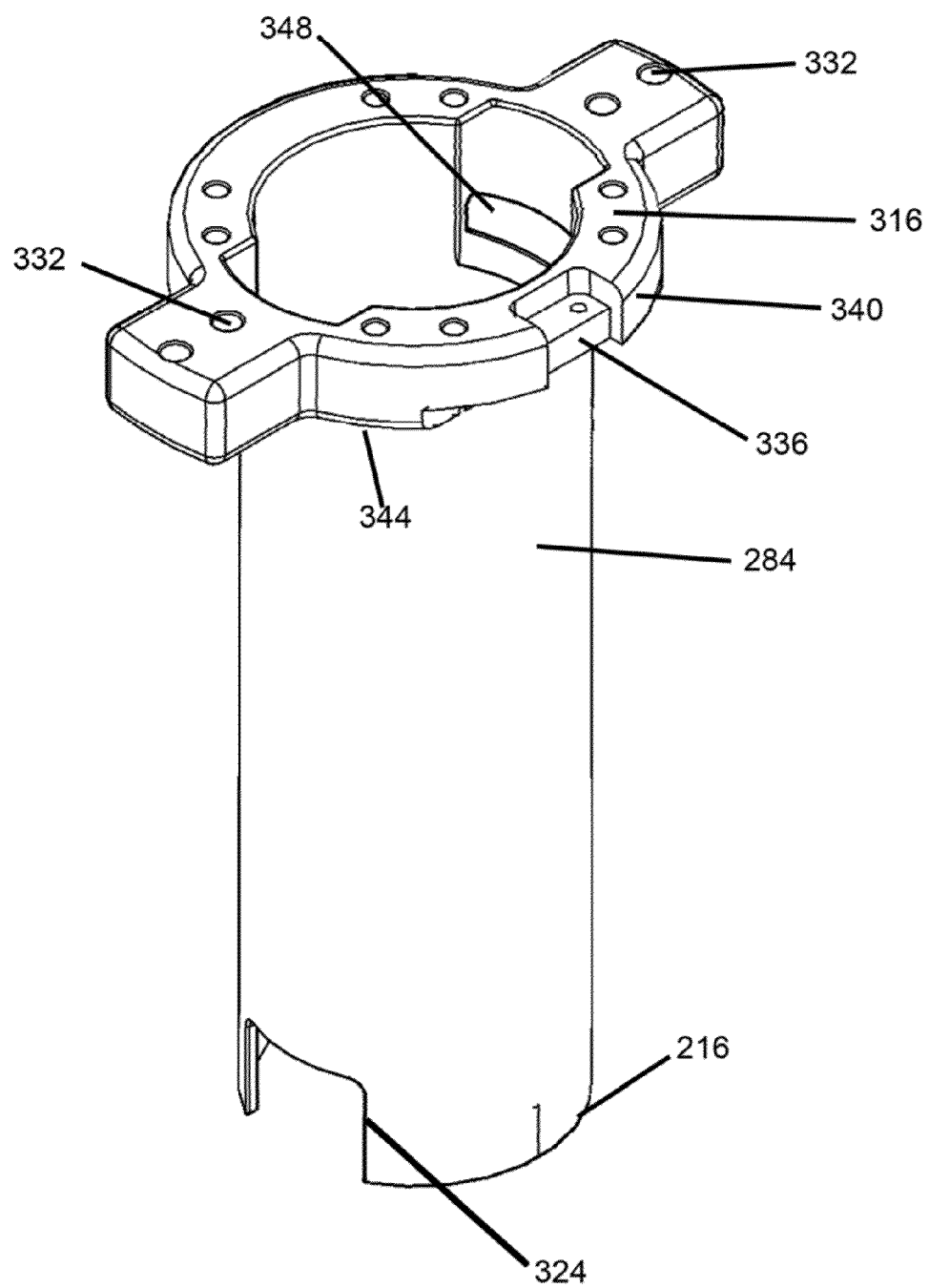
FIG. 10 is a top perspective view of a channel retractor.
Figure 11:
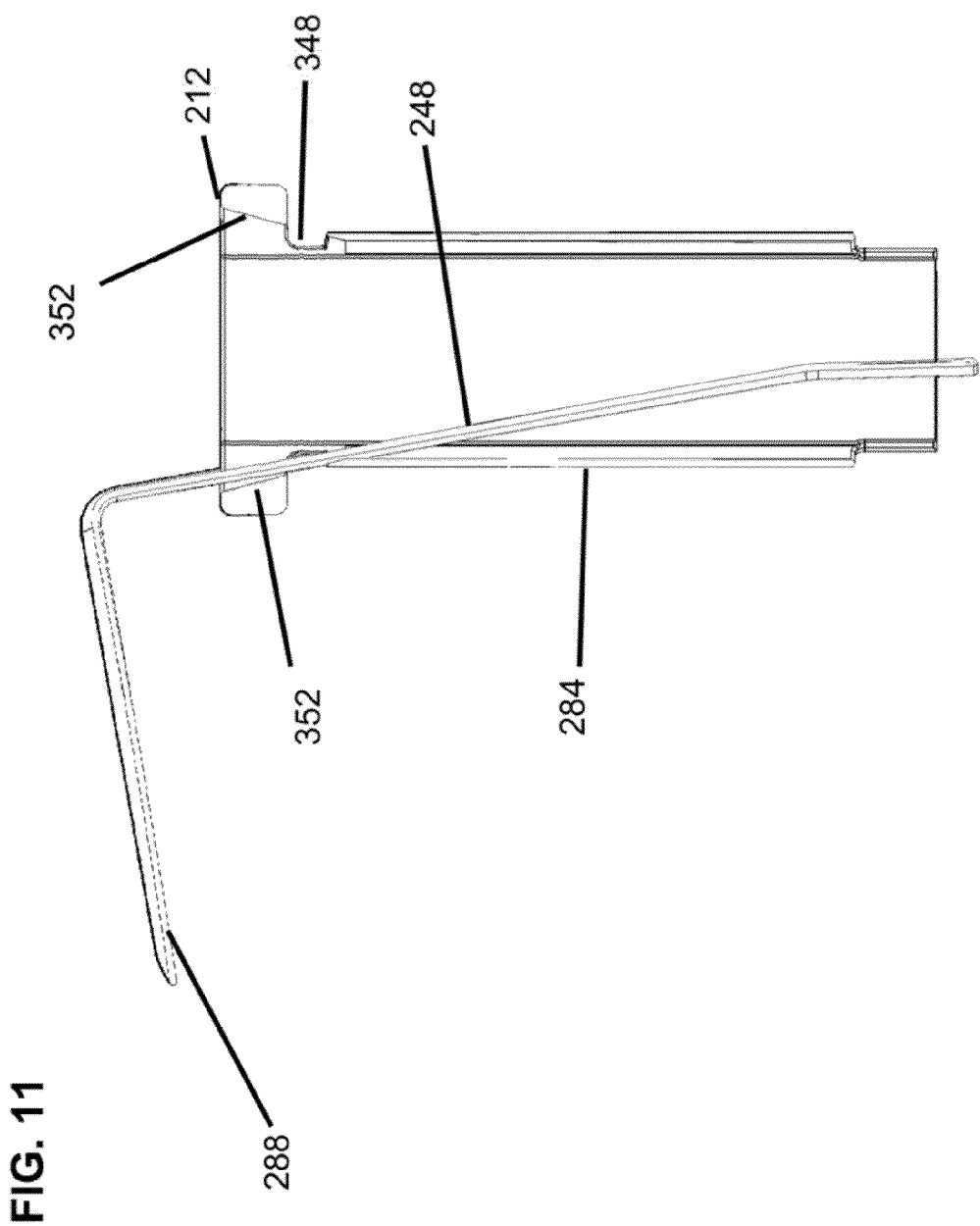
FIG. 11 is a cross section of a channel retractor with beveled portions.

Details for an example of a channel retractor 284 are shown in FIG. 10 and FIG. 11. FIG. 10 is a top perspective view of the channel retractor 284. Bores 332 for receiving dowel pins to serve as protrusions 312 to interact with the slots 304 on the extended retractors 288, 292 are visible. A connection space 336 for connecting a stabilizer arm 168 (discussed above) is visible. The connection space 336 is recessed relative to the proximal face 316 and bottom face 344 of the proximal flange 340 so that a stabilizer arm 168 may be connected without changing the thickness of the proximal flange 340. As previously noted, the distal end 216 of the channel retractor 284 includes notches 324 for receiving the distal portions 296 of the extended retractors when the extended retractors 288, 292 are pushed outwards.

FIG. 10 also reveals a proximal gap 348 in the channel retractor 284 that prevents the channel retractor 284 from limiting the ability of the two extended retractors 288 and 292 to extend their distal portions 296 into a slit in the psoas muscle.

In FIG. 11, the channel retractor 284 has a pair of beveled portions 352 near the proximal end of the channel retractor 284 to receive the portion 248 (discussed above) for traversing the channel retractor of the extended retractors 288, 292 or when the distal portions 296 of the extended retractors 288, 292 are initially positioned near the centerline of the channel retractor 284 in the narrow opening of the psoas muscle. The angle shown in FIG. 11 is a thirty degree bevel although other angles may be used. The beveled portions 352 extend down below the flange at the proximal end 212 of the channel retractor 284 and thus cause one or more proximal gap 348 in the perimeter of the channel retractor.

Component Details.

The channel retractor 284 or other channel retractors as shown throughout may be constructed of a material that is substantially transparent to fluoroscopy. The channel retractor 284 may have a series of one or more markers that are radio-opaque or at least substantially more radio-opaque than the channel retractor 284. The more opaque markers show clearly on fluoroscopy imaging to help discern the placement and alignment of the channel retractor 284 relative to various component including landmarks in the patient's body and other radio-opaque tools or components. Markers are frequently spheres or rods but other shapes could be used. Tantalum is an example of a material used for markers.

Alternatives.

Figure 12:
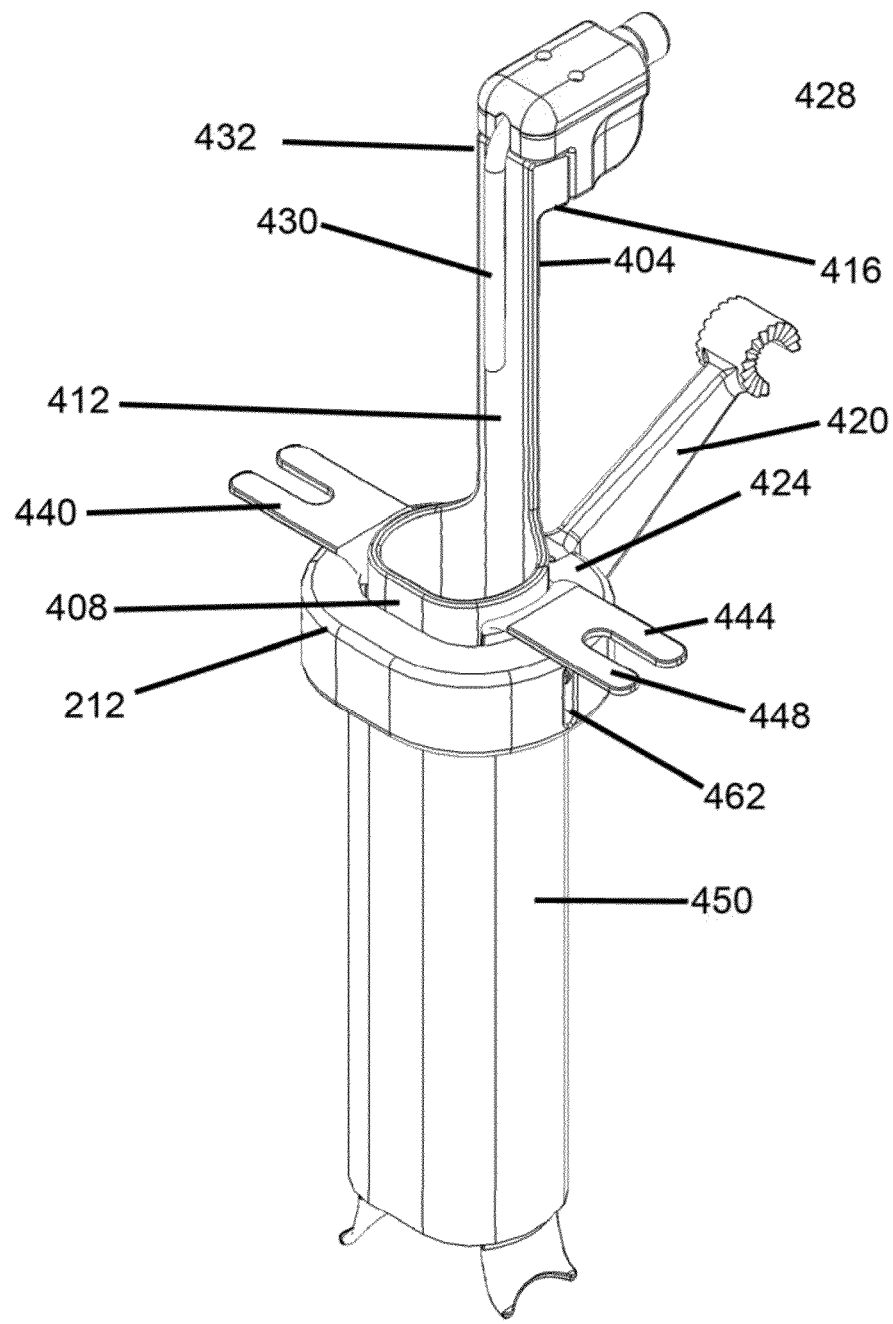
FIG. 12 shows another alternative inner sleeve.

FIG. 12 shows another alternative inner sleeve 404. This inner sleeve 404 has a first section 408 that is a closed perimeter loop and a second section 412 that is longitudinal handle. The inner sleeve 404 has a flange 416 that protrudes outward and serves as a stop when the flange 416 contacts the proximal face 424 of the channel retractor 450. The stabilizer arm 420 used in FIG. 12 connects to the proximal end 212 of the channel retractor 450 in a manner that leaves the proximal face 424 of the channel retractor 450 substantially flat.

The inner sleeve shown in FIG. 12 has an integrated light assembly 428 with a light tube 430 that conveys light from an external light source (not shown). The integrated light assembly 428 with light tube 430 is integrated with a proximal end 432 of the inner sleeve 404. This integrated light assembly 428 allows the psoas muscle to be illuminated as the inner sleeve 404 is being inserted into the channel retractor 450 to drive the extended retractors 440, 444 apart to increase the opening in the psoas muscle.

The first extended retractor 440 and the second extended retractor 444 may be interchangeable parts. A handle portion 448 of the extended retractors 440, 444 shown in FIG. 12 are substantially perpendicular to the long portions 454 of the extended retractors (mostly within the channel retractor 450) so that the handle portion 448 may serve as a stop by contacting the proximal face 424 of the channel retractor 450. The handle portions 448 of the extended retractors 440, 444 shown in FIG. 12 are relatively short but may be used with a handle extension (not shown) that interacts with the two prongs at the ends of the handle portions 448. Partially visible on one side of the channel retractor 404 is a slot 462 discussed in more detail in connection with FIG. 13.

As discussed above, if necessary, one extended retractor may not be inserted into the psoas muscle as deeply as the other extended retractor and thus may not be in contact with the proximal face 424 of the channel retractor 450.

Figure 13:
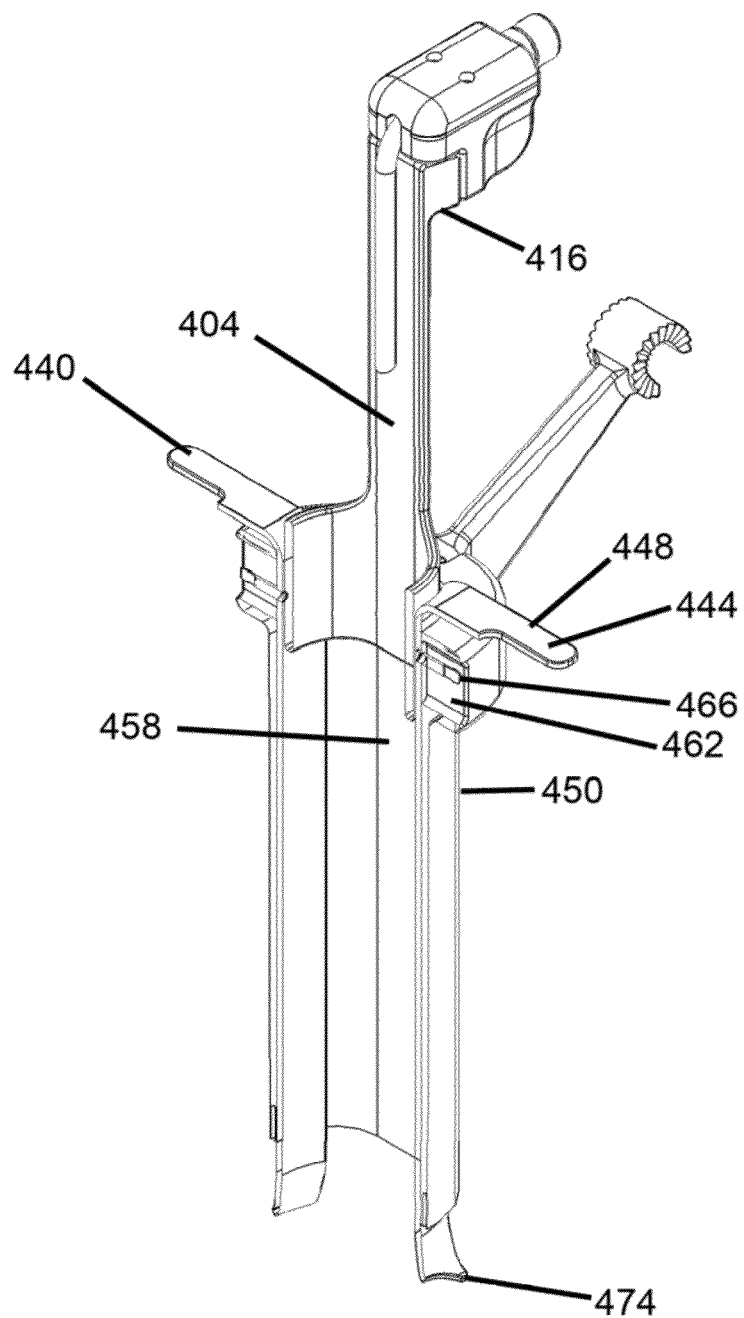
FIG. 13 is a cross section of the same assembly as shown in FIG. 12 with the cross section taken through the midlines of the two extended retractors.

FIG. 13 is a cross section of the same assembly as shown in FIG. 12 with the cross section taken through the midlines of the two extended retractors 440 and 444. As the inner sleeve 404 is moved distally in the channel retractor 450 to maintain gentle pressure on the extended retractors 440, 444 until the inner sleeve is stopped by contact from the flange 416 at the proximal end 432 of the inner sleeve 404 hitting the proximal face 424 of the channel retractor 404.

Visible in FIG. 13 are slots 462 in the channel retractor 404. Retractor protrusions 466 located near the extended retractor handle portions 448 are inserted into the slots 462 when a distal end 474 of the extended retractor 440, 444 is placed into the slit opening in the psoas muscle. Optional slot indicator lines may be placed on the proximal face 424 to assist in aligning the retractor protrusions 466 with the slots 462. As the inner sleeve 450 is advanced distally within the interior of the channel retractor 450, the interaction between the retractor protrusions 466 and the slots 462 maintain the two extended retractors 440 444 on opposite sides of the channel retractor 450. The slots 462 in the channel retractor 450 allow for a limited range of proximal/distal movement of the extended retractors 440, 444 even when pressed against the inner perimeter 458 wall of the channel retractor 450 by an inserted inner sleeve 404.

One of skill in the art will recognize that the components shown in FIG. 13 could be modified so that the slots are on the longitudinal portions of the extended retractors and the protrusions extend outward from the inner wall of the channel retractor.

One of skill in the art will recognize that the cross section of the channel retractor 450 from FIG. 12 could be something other than a rounded rectangle/oval. The cross section could be circular or some other shape. When using a circular channel retractor, care needs to be taken to place the slots in proper relationship with the patient anatomy so that the distal ends 474 of the extended retractors 440 444 are placed into the slit into the psoas rather than at an angle to the slit. The slot indicator lines may help with this alignment process.

Figure 14:
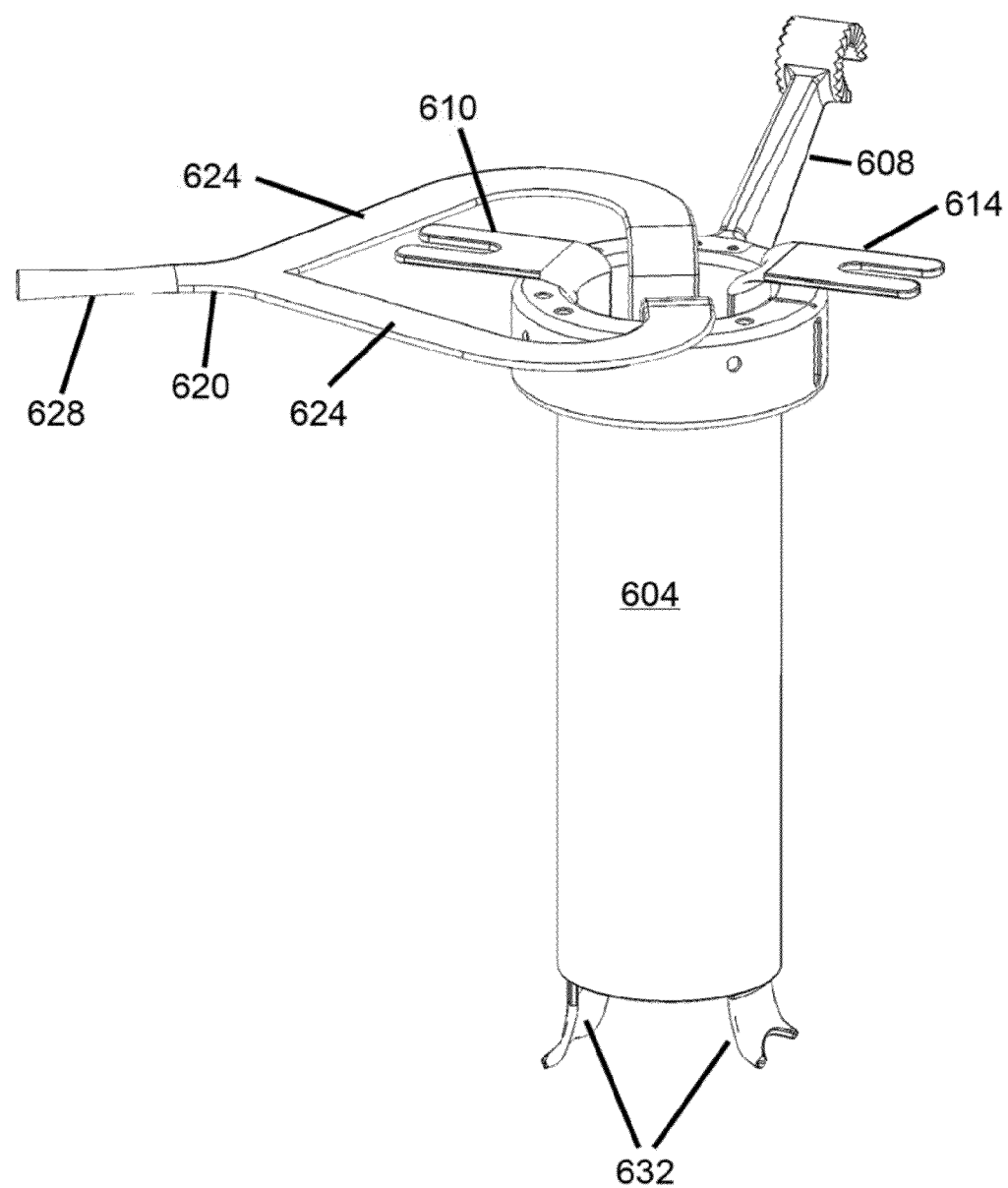
FIG. 14 shows another round channel retractor with a stabilizer arm and two extended retractors with an alternative inner sleeve.

FIG. 14 shows another round channel retractor 604 with a stabilizer arm 608 and two extended retractors 610, 614 with an alternative inner sleeve 620. This inner sleeve 620 includes integrated light pathways 624 to provide light on either side of the pair of extended retractors 610, 614. The pair of light pathways 624 joins to form a common conduit path 628 for connection to a light source (not shown). The inner sleeve 620 of FIG. 14 may benefit from a durable inner liner that protects the light pathways 624 of the inner sleeve 620 from possible damage from tools inserted through the inner sleeve 620 to work at the surgical site. Likewise, the inner sleeve 620 of FIG. 14 may benefit from an outer liner that protects the light pathways 620, 624 of the inner sleeve 620 from damage as the inner sleeve presses against the extended retractors 610, 614 with sufficient force to cause the distal portions 632 of the extended retractors 610, 614 to widen the opening through the psoas muscle.

Figure 15:
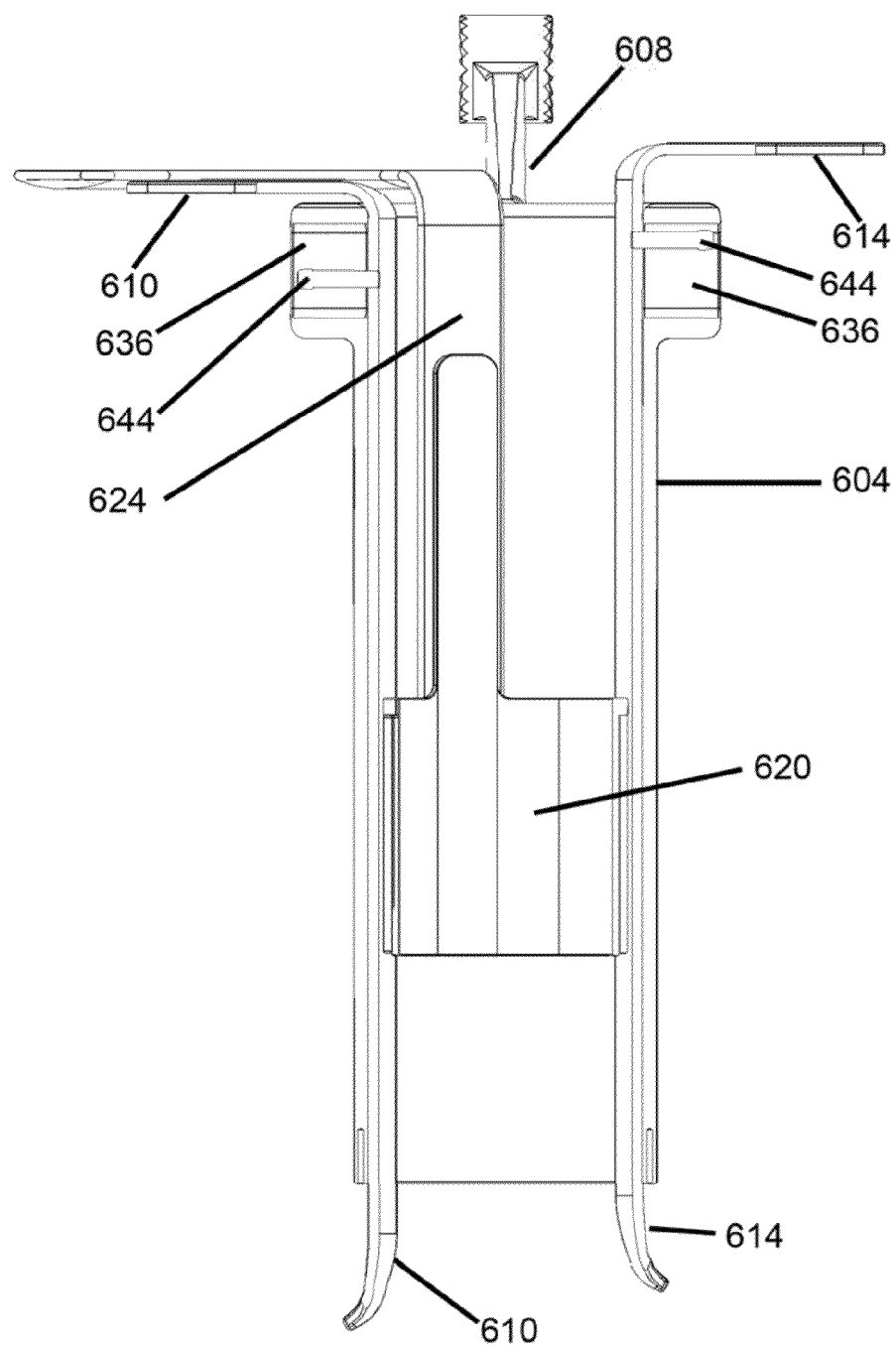
FIG. 15 shows a cross section of FIG. 14 taken through the midlines of the extended retractors.

FIG. 15 shows a cross section of FIG. 14 taken through the midlines of the extended retractors 610, 614 to reveal the slots 636 in the channel retractor 604 and the retractor protrusions 644. An inner sleeve of the type shown as element 620 may be used with a non-circular channel retractor provided that the location of the stabilizer arm 608 is accounted for in the design. Making the light pathways 624 flexible such that they have some capacity to bend around the stabilizer arm 608 may be part of the solution.

Figure 16:
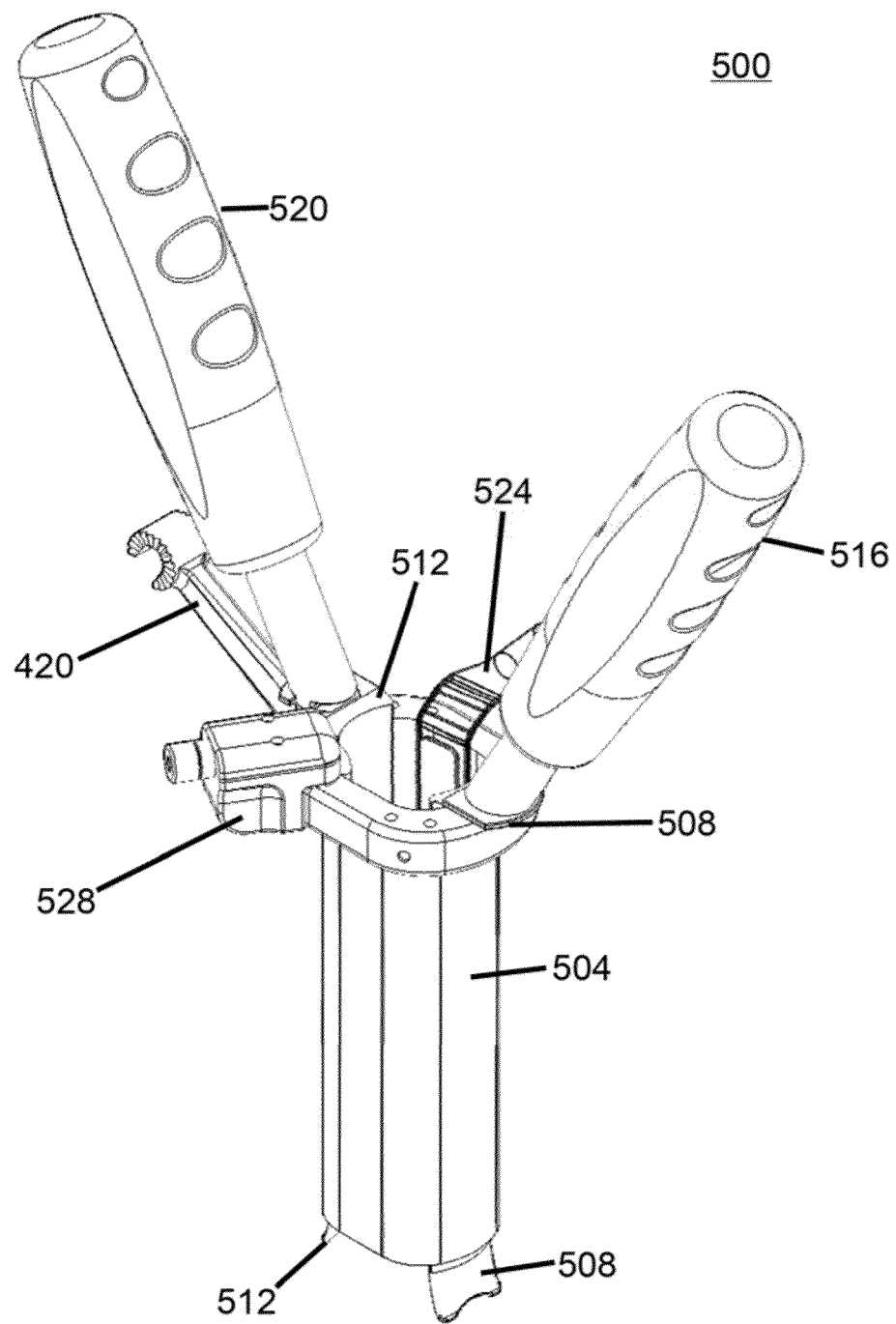
FIG. 16 shows another tube in tube assembly.

Another tube in a tube assembly 500 is shown in FIG. 16. Visible are channel retractor 504, stabilizer arm 420, first extended retractor 508, second extended retractor 512, removable handles 516 and 520, inner sleeve 524, and stadium light 528. Neither the inner sleeve 524 nor the stadium light 528 are shown connected to external light sources in order to focus on the relevant components.

Figure 17:
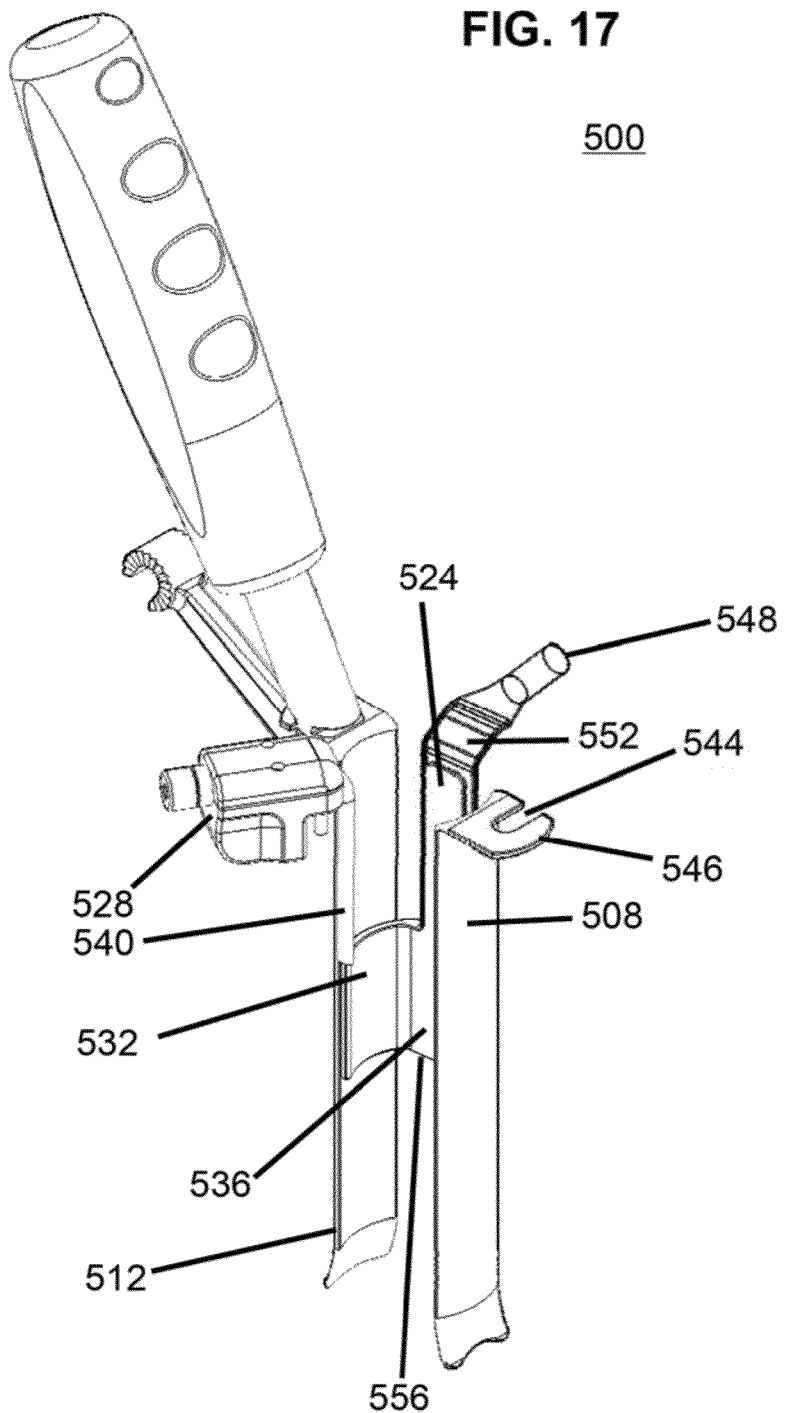
FIG. 17 is the view shown in FIG. 16 of the assembly but with the channel retractor made invisible to show components inside and with one removable handle removed.

FIG. 17 is the view shown in FIG. 16 of the assembly 500 but with the channel retractor 504 made invisible to show components inside and with one removable handle 516 removed. FIG. 17 shows that the inner sleeve 524 is a C-shaped inner sleeve with two arms 532 with an intermediate portion 536 rather than a closed perimeter type inner sleeve such as inner sleeve 620.

Illumination.

Illumination can come from light emitted from the distal light tube 540 of the stadium light. The stadium light 540 may be removed after placement of inner sleeve 524 as the inner sleeve 524 may have a light source.

Figure 18:
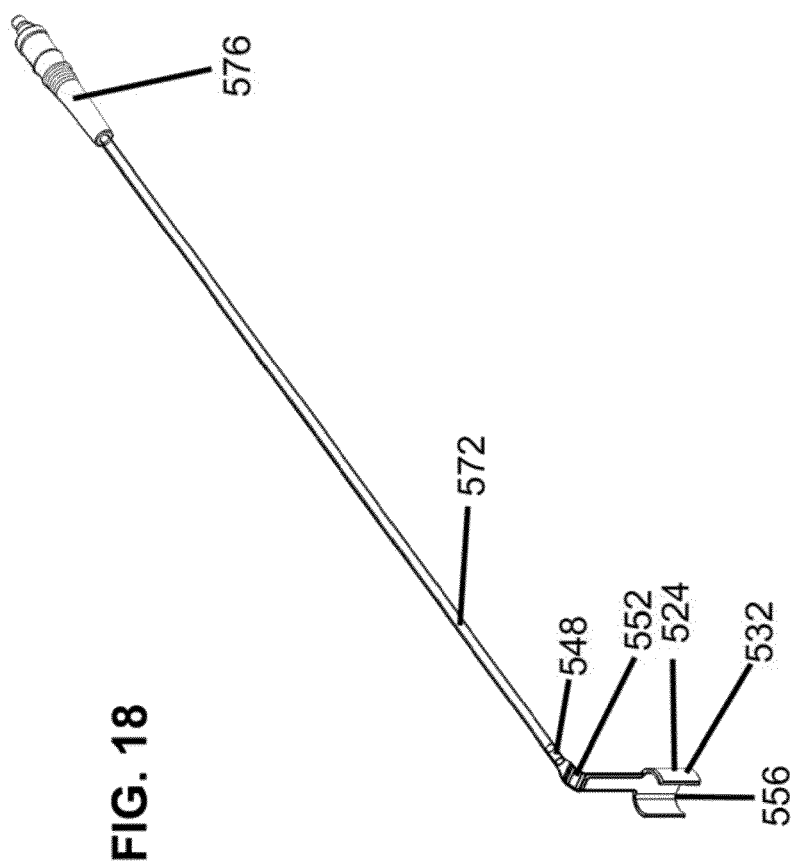
FIG. 18 shows the inner sleeve with flexible tubing connected to light connector.

FIG. 18 shows the inner sleeve 524 with flexible tubing 572 connected to light connector 576. The light connector 576 may be a male ACMI instrument connector which can connect with a female ACMI instrument connector supplying light from a suitable instrument. Light entering the light connector 576 may be conveyed through fiber optic fibers through the flexible tubing 572 to enter the inner sleeve 524 through light path 548. The array of light fibers are arranged in a ribbon zone 552 located in the proximal end of the inner sleeve 524. The array of light fibers in the ribbon zone 552 may move to the distal edge 556 of the inner sleeve 524. The array of light fibers in ribbon zone 552 may splay outward to create a light emitting portion of the distal edge 556 of the inner sleeve 524 that extends into the arms 532 to broaden the output of light and thus reduce shadows in the surgical site. Thus, splaying the array of fiber optic fibers causes light to come from an expanded portion of the distal perimeter of the inner sleeve.

Figure 19:
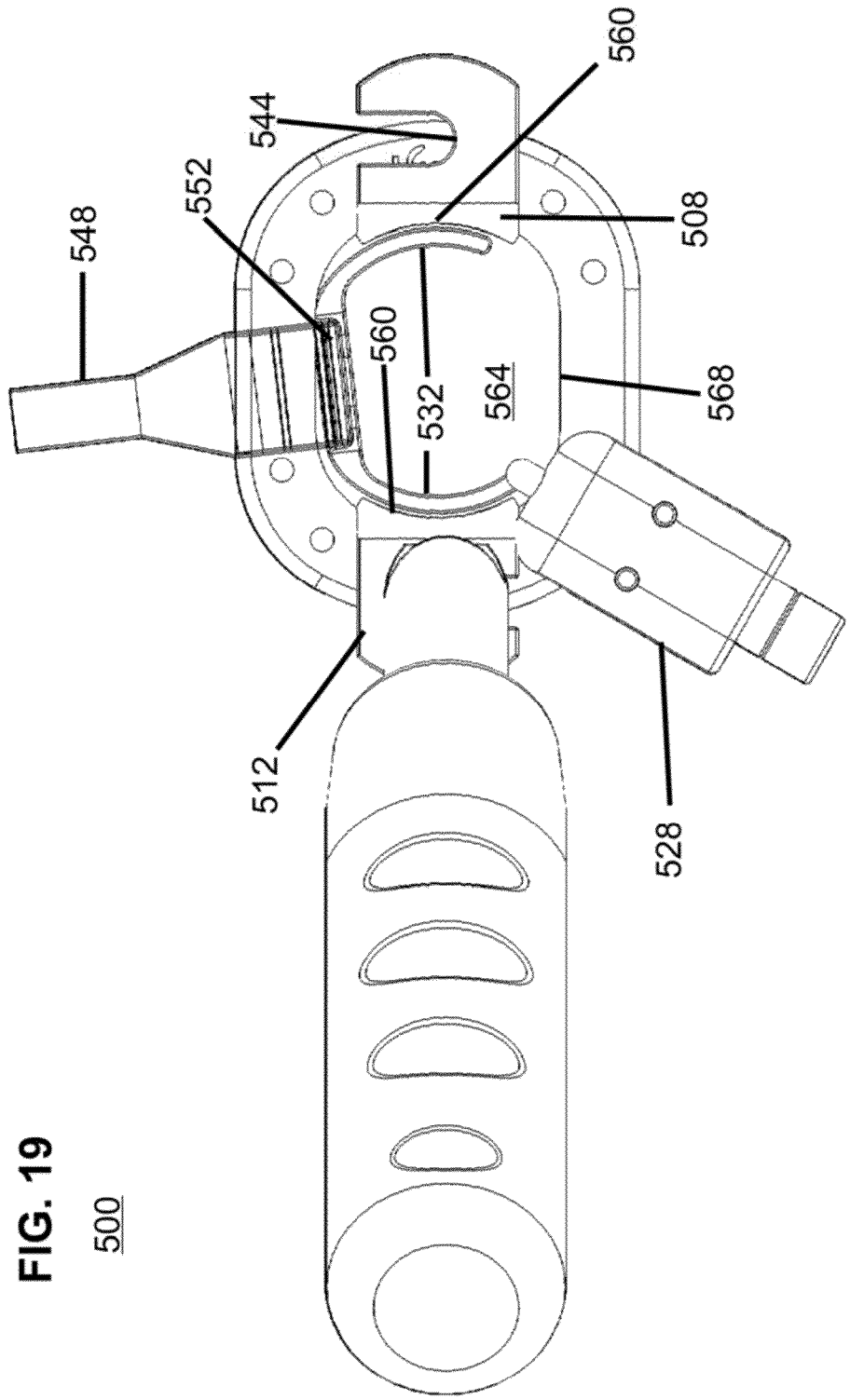
FIG. 19 shows a top view of the assembly from FIG. 16 but without removable handle.

FIG. 19 shows a top view of the assembly from FIG. 16 but without removable handle 516. Notice that inner sleeve 524 may be rotated slightly with respect to extended retractors 508 and 512 but has arms 532 that have curvature that substantially corresponds to a concave curve 560 in each of the extended retractors 508 and 516.

The extended retractor 508 is shown without removable handle 516 and reveals the lateral gap 544 along a lateral edge of the extended retractor that may be used as the interaction to connect the removable handle 516 with the extended retractor 508. An alternative would be to have a gap (not shown here) at the extreme end 546 of the extended retractor 508.

Assembly 500 leaves a working channel 564 that is a substantial fraction of the cross section of the inner perimeter 568 of channel retractor 504.

One of skill in the art will appreciate that a C-shaped inner sleeve could be made without integrated light channels. The inner sleeve could have a distal C-shaped section, an intermediate section and a proximal section with a proximal flange to serve as a stop when the proximal flange contacts the proximal face of a channel retractor. Such a C-shaped inner sleeve may be made from a material such as 7075 aluminum alloy. The C-shaped distal portion may be sized for certain operations to be about 29 millimeters wide (anterior to posterior) and about 18 millimeters deep. The material may be about 1.75 millimeters thick. In contrast the intermediate section may be about 16 millimeters wide and about 1.3 millimeters thick. The proximal to distal length of the inner sleeve may be in the range of about 100 millimeters long. When using an inner sleeve without an integrated light source, the assembly may use a stadium light such as 528 above or may use a stadium light integrated with a proximal portion of an inner sleeve such as light assembly 428 on inner sleeve 404.

When designing a C-shaped inner sleeve, one may opt for medical grade stainless steel which is sufficiently stiff to allow a relatively thin wall while providing adequate force to push apart a pair of extended retractors (sometimes called extended retractor blades) to enlarge a gap in the psoas muscle. However, medical grade stainless steel is radio-opaque and will make lateral visualization difficult for items in the channel retractor. Aluminum is relatively radio-translucent, but would require thicker walls to provide the same strength as stainless steel, if necessary. The aluminum inner sleeves may be made with Tantalum markers so that the placement of the inner sleeve may be indicated in fluoroscopic images.

One of skill in the art will appreciate that the acute angle of attachment for removable handles 516 and 520 to extended retractors 508 and 512 allow the removable handles 516 and 520 to convey force from the hands of the surgeon to the distal end portions of the extended retractors 508 and 512 to enlarge a gap in tissue distal to the distal end of the channel retractor 504. Thus, the enlargement of the tissue may be achieved before insertion of the inner sleeve 524. In this scenario, the insertion of the inner sleeve 524 serves an important function of maintaining the extended retractors 508 and 512 against the inner perimeter 568 of the channel retractor 504 to maintain the enlarged gap in the tissue.

Focus on Extended Retractors.

Figure 20:
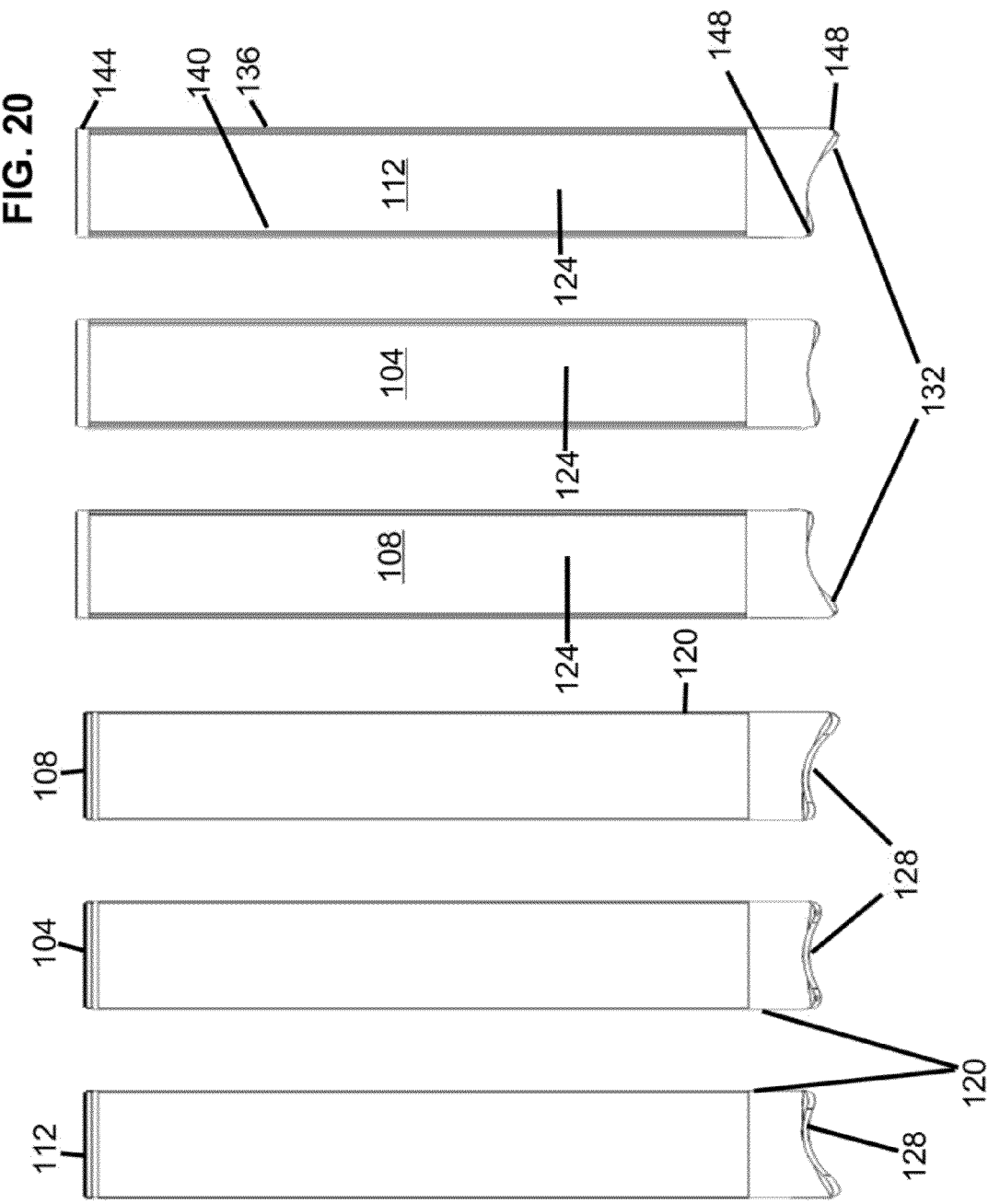
FIG. 20 shows front and back plan views of three extended retractors.

FIG. 20 shows front and back plan views of three extended retractors 104, 108, 112. The front side may be a convex side 120 with a curvature that substantially matches the inner perimeter of the applicable channel retractor. The back side may be a concave side 124 that substantially matches a curvature of the applicable inner sleeve. All three extended retractors have distal concavities 128. These distal concavities 128 help the distal tip of the extended retractor work with curved anatomical features such as the lateral sides if vertebrae or an annulus. Extended retractors 108 and 112 have asymmetric distal ends 132 in that one side is longer than the other. Thus, extended retractors 108 and 112 each have one side 140 with a first distance between a handle portion 144 and a distal tip 148 and an opposite side 136 with a second distance, less than the first distance, between the handle portion 144 and the distal tip 148. Extended retractors 108 and 112 may be used to place the distal tips 148 for the first side 140 and the second side 136 of the extended retractor adjacent to a patient's spine when the channel retractor is inserted into the patient at an oblique angle with a cephalad/caudal axis of the patient's spine. The channel retractor may have a distal end cut at an oblique angle with respect to a proximal/distal axis of the channel retractor.

Figure 21:
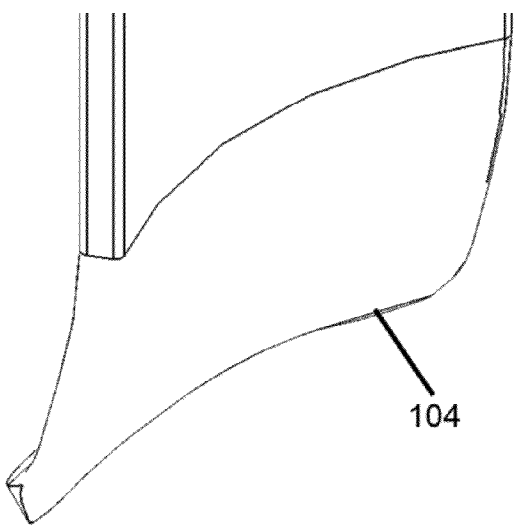
FIG. 21 shows an enlarged distal portion of extended retractor.
Figure 22:
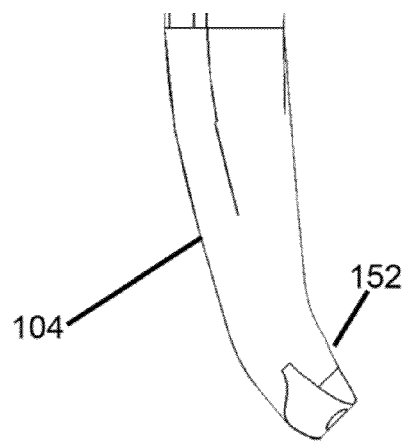
FIG. 22 shows a side view of an enlarged distal portion of extended retractor.
Figure 23:
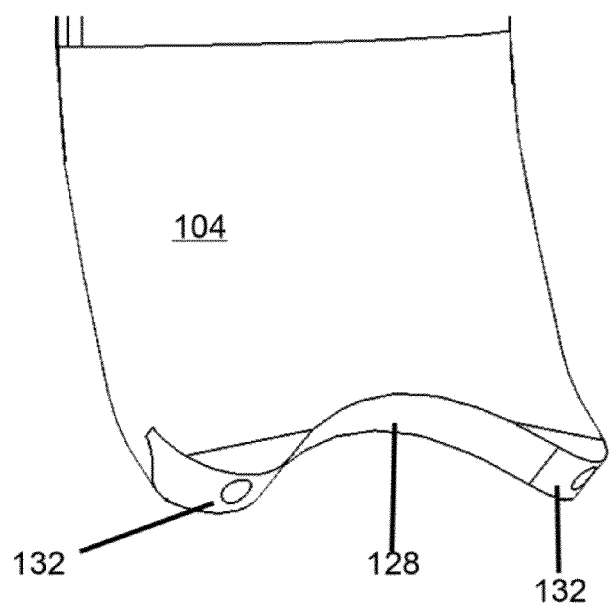
FIG. 23 shows a perspective view of the front side an enlarged distal portion of extended retractor.
Figure 24:
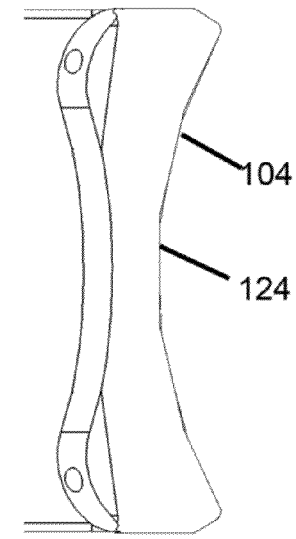
FIG. 24 shows a bottom view of an enlarged distal portion of extended retractor.

FIG. 21 shows an enlarged distal portion of extended retractor 104. FIG. 22 shows a side view of an enlarged distal portion of extended retractor 104. FIG. 23 shows a perspective view of the front side an enlarged distal portion of extended retractor 104. FIG. 24 shows a bottom view of an enlarged distal portion of extended retractor 104. These four views augment the views in FIG. 20 to show the flared tip 152 that extends away from the centerline of the channel retractor. The flared tip 152 may be useful in working the psoas muscle away from the patient's spine.

Atraumatic Soft Cover or Tip.

A soft cover or tip may be added to the distal end of the extended retractors 104, 108, 112. The soft cover or tip may be used to minimize trauma through the use of this atraumatic tip. The malleable soft cover also makes the distal end of the extended retractors 104, 108, 112 conform to the surface of the patient anatomy to make them more effective at sweeping tissue back from the spine. The malleable cover uses a softer material compared to the distal covered portion of the extended retractor covered by the malleable soft cover.

The soft cover or tip may be made of a silicone elastomer or other suitable biocompatible materials that may be sterilized in accordance with the sterilization plan for the extended retractors 104, 108, 112. One of skill in the art will be able to make the design choice on how stiff the soft cover or tip should be in order to be used effectively but atraumatically.

Process of Secondary Retraction Using Tube in Tube.

After creating a small opening through the psoas muscle with a dissector tool such as the angled Cobb dissector 176 (above), a retractor tool such as a 90 degree nerve retractor may be inserted along the dissector to retract the muscle posteriorly. Alternatively, a Penfield or Cobb distractor may be used instead of the 90 degree nerve retractor. Note that while an extended retractor may be used for this purpose as well, extended retractors which curved tips may not be the first choice for this task.

A first extended retractor may be used to retract the psoas muscle anteriorly. As the muscle is retracted, the distal tip of the extended retractor is maintained in contact with the annulus and the vertebral body. The extended retractor may come in more than one length. For example the extended retractor may come in two lengths such as 165 millimeters and 205 millimeters. As noted above, the channel retractor may come in several lengths. The choice of length for use in a procedure is impacted primarily by the choice of channel retractor length but secondarily by the thickness of the psoas muscle as the extended retractor will need to extend through the channel retractor 208 and the split psoas muscle to reach the spine. Depth markings on the angled Cobb dissector 176 or other tool may be helpful to judge insertion depth as may fluoroscopy.

While maintaining gentle pressure on the first extended retractor, the 90 degree nerve retractor may be removed.

A second extended retractor may be inserted into the split psoas to retract the psoas posteriorly while maintaining contact with the annulus or vertebral body.

Gently, inserting an inner sleeve into the channel retractor and moving the distal end of the inner sleeve towards the distal end of the channel retractor pushes the extended retractors outward. As noted above the inner sleeve may be a full perimeter sleeve, a C-shaped sleeve, or a ring clip. As noted above, the extended retractors may be engaged with the channel retractor to limit movement of the extended retractors around the perimeter of the channel retractor.

Alternatively the handles on the extended retractors may be used to apply force to create an enlargement of the opening in the psoas muscle and subsequent insertion of the inner sleeve may be used to hold the opening in the retracted position. The combination of the extended retractor and the removable handle may be called an extended retractor assembly.

Continue inserting the inner sleeve until the inner sleeve flange contacts the proximal face of the channel retractor.

Internal Retraction Insertion.

Overview.

As noted above, the tube in a tube type secondary retraction provides one family of solutions to the need for providing force to distract tissue distal to a channel retractor such as a tube. Another family of solutions may be called internal retraction insertion. In this family of solutions, an internal retractor assembly (frequently having two blades or arms) is reversibly engaged by a driver (internal retractor inserter) and inserted through the channel retractor so that the distal ends of the retractor blades extends beyond the distal end of the channel retractor and insert into the tissue that needs to be retracted such as the small opening in the psoas muscle prepared above. The internal retractor inserter conveys force from outside the patient to a mechanism in the bladed retractor assembly to cause the distal tips of the bladed retractor assembly to spread apart relative to an insertion path for the internal retractor through the channel retractor and thus controllably retract the tissue distal to the distal end of the channel retractor. One device for providing force from outside the patient to a mechanism is an internal retractor inserter such as internal retractor inserter 1000 discussed below.

After the tissue has been retracted, the internal retractor assembly does not need any additional force from the internal retractor inserter to maintain the tissue in a retracted position. The internal retractor inserter may be disengaged from the internal retractor assembly and removed to avoid being an obstacle to subsequent tool insertion and use through the extended access channel that now includes an enlarged working channel through the psoas muscle.

After work on the surgical site (such as work on a disc space) is completed, the internal retractor inserter may be engaged with the internal retractor assembly to cause the internal retractor assembly to draw the distal ends of the retractor blades sufficiently together to allow removal of the internal retractor assembly through the channel retractor. Examples of force provide by an internal retractor inserter include torque and linear force.

Internal Retractor Assembly.

While those of ordinary skill in the art may take the teachings of the present disclosure and create a variety of internal retractor assemblies that convert torque or other force received from an appropriate retractor inserter into lateral movement of a pair of blades to controllably increase an opening in tissue beyond the channel retractor, showing details of suitable internal retractor assemblies may be helpful to some readers.

Figure 25:
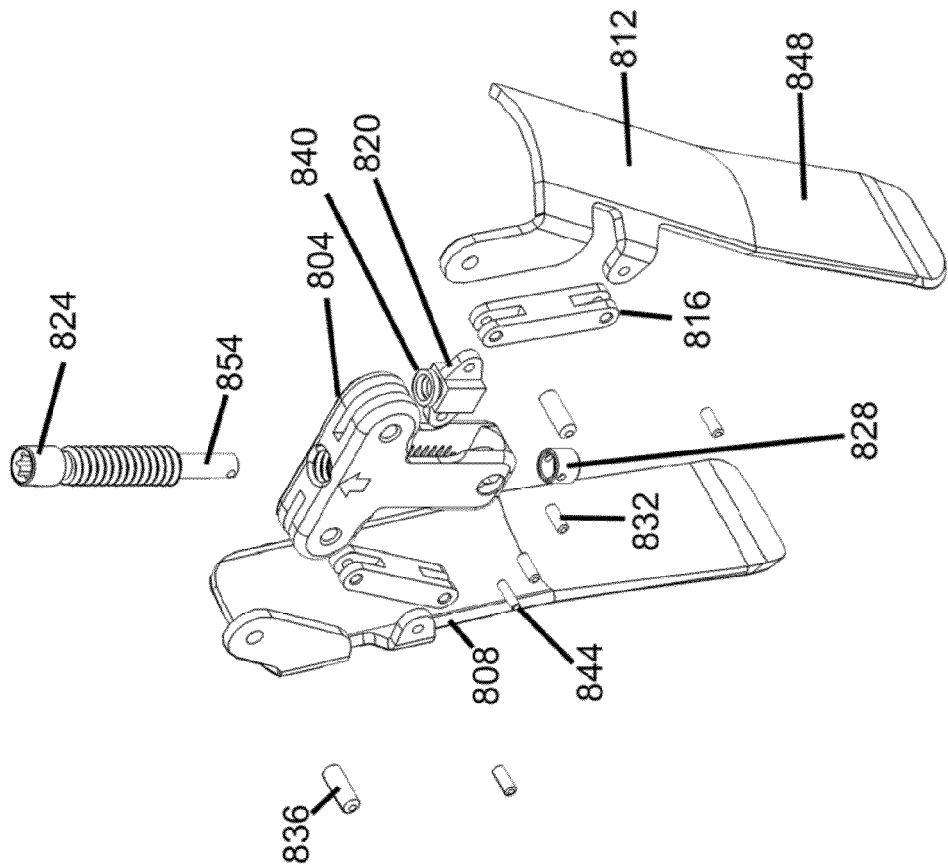
FIG. 25 is an exploded diagram of an internal retractor assembly.

FIG. 25 is an exploded diagram of an internal retractor assembly 800. The components shown are: a housing 804, a left retractor arm 808, a right retractor arm 812, a pair of support arms 816, a retractor nut 820, a retractor screw 824, a retractor stop 828, a set of four support fixation pins 832, a pair of arm fixation pins 836, a thrust washer 840, and a retractor stop fixation pin 844.

When assembled, the unthreaded distal portion 854 of the retractor screw 824 is surrounded by an unthreaded bore in the retractor nut 820. The retractor nut 820 is retained by the retractor stop 828 which is pinned to the unthreaded distal portion 854 of the retractor screw 824 by the retractor stop fixation pin 844.

As the proximal end 858 of the retractor screw 824 receives torque from an internal retractor inserter, the retractor screw 824 rotates and translates relative to the housing 804. The retractor nut 820 does not rotate with the retractor screw 824, but translates within the housing 804 with the retractor screw 824 to move the two support arms 816 which cause lateral movement of the right retractor arm 812 and left retractor arm 808.

Figure 26:
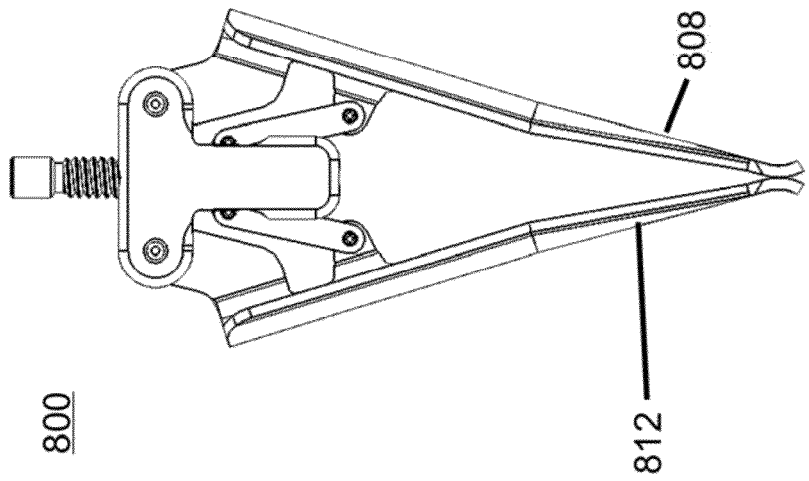
FIG. 26 is a rear perspective view of an assembled internal retractor from FIG. 25.
Figure 27:
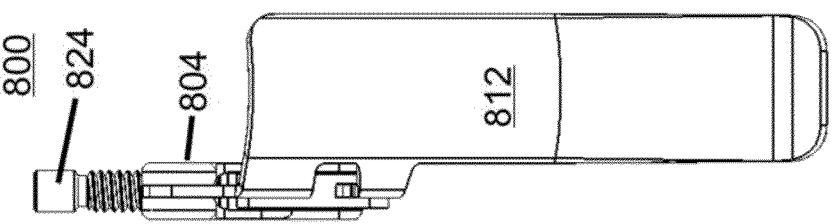
FIG. 27 is a side view of an assembled internal retractor from FIG. 25.
Figure 28:
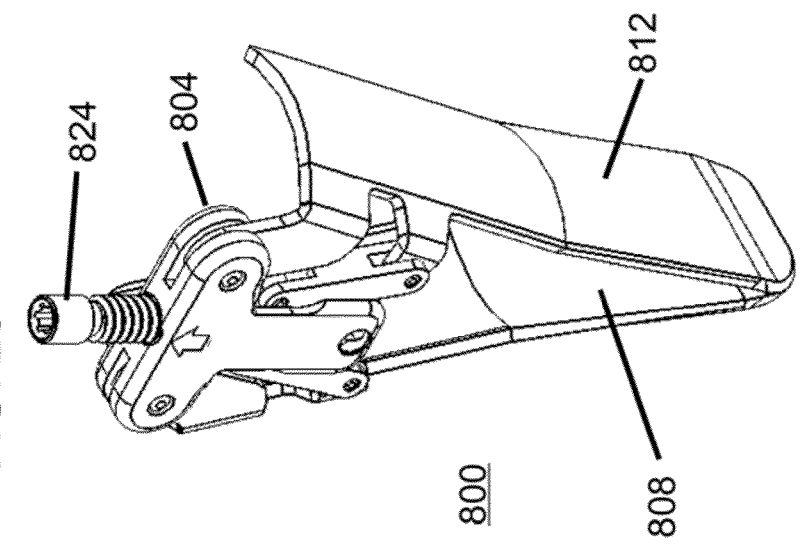
FIG. 28 is a front view of an assembled internal retractor from FIG. 25.

FIG. 26, FIG. 27, and FIG. 28 show a rear perspective view, side view, and front view of an assembled internal retractor assembly 800. These views show how the housing 804 and the retractor screw 824 are positioned along one side of the internal retractor assembly 800. This placement means that the housing 804 does not interfere with movement of tools or implants from the proximal end of the channel retractor down to the gap between the distal tips of the right retractor arm 812 and left retractor arm 808 when those arms are in the expanded position.

Figure 29:
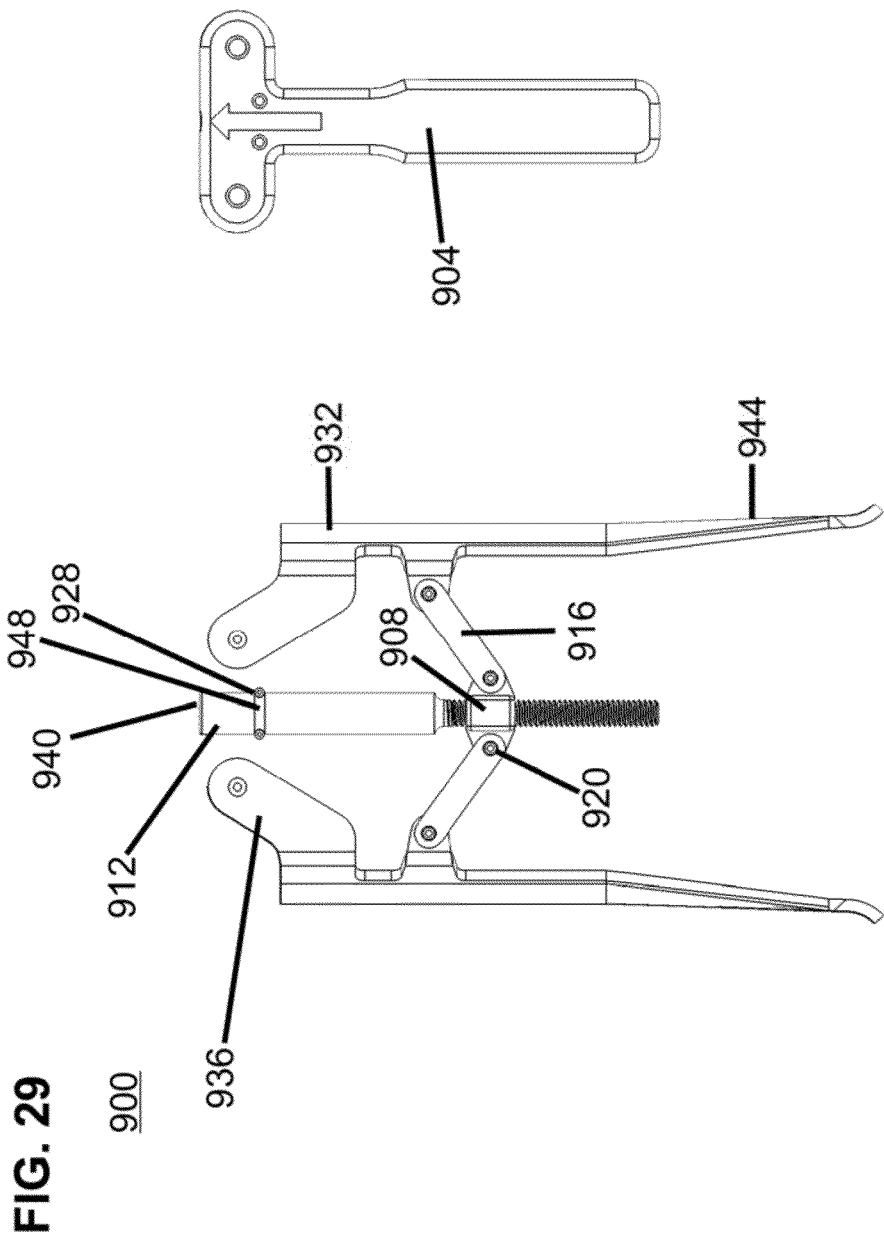
FIG. 29 shows a partially exploded diagram for an alternative design for an internal retractor assembly.
Figure 30:
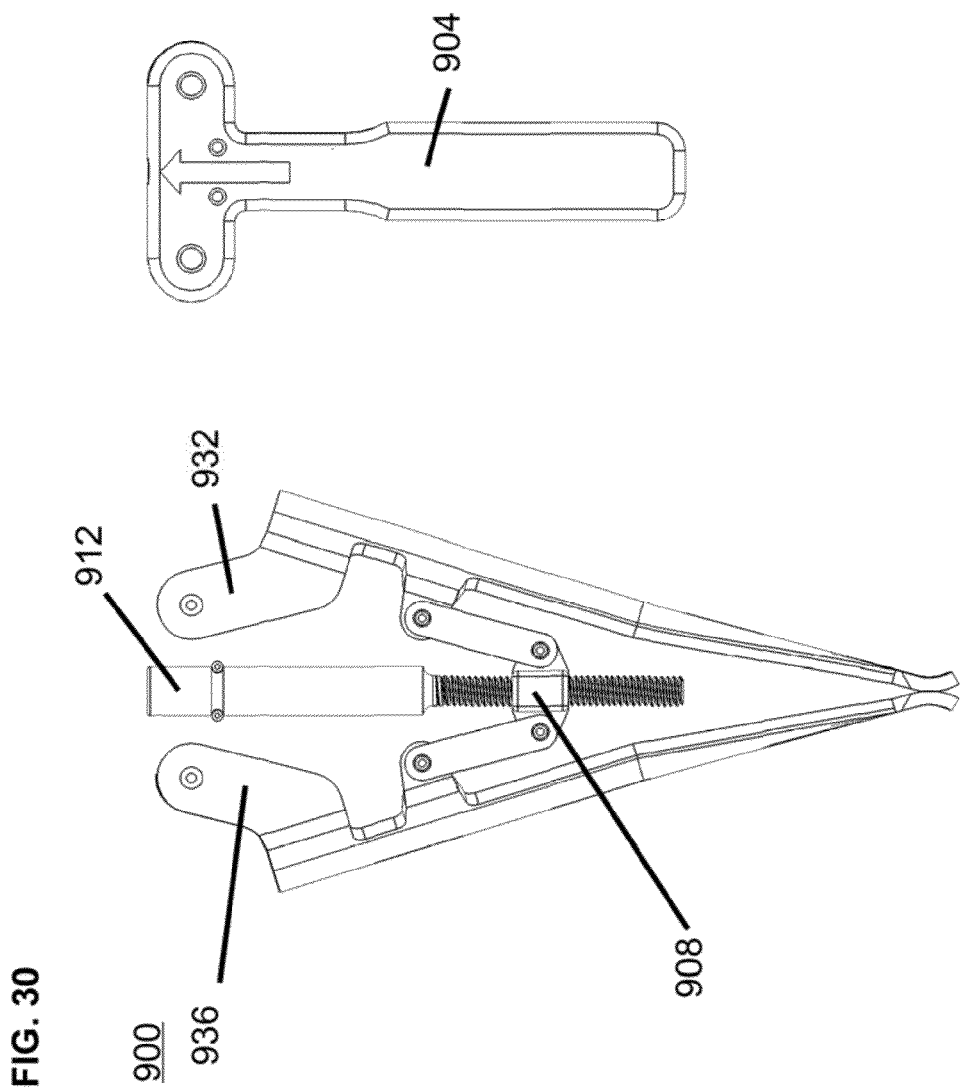
FIG. 30 provides the same partially exploded diagram but for internal retractor assembly in a closed position.

FIG. 29 shows a partially exploded diagram for an alternative design for an internal retractor assembly 900. By partially exploded, FIG. 29 shows an internal retractor assembly 900 in the expanded position with the housing 904 removed and placed to the right of the internal retractor assembly 900 to allow examination of the parts that would be otherwise within the housing 904. FIG. 30 provides the same partially exploded diagram but for internal retractor assembly 900 in a closed position.

Parts visible in FIG. 29 are: housing 904, retractor nut 908, retractor screw 912, a pair of support arms 916, a set of four support arm fixation pins 920, a pair of retractor arm fixation pins 924, a pair of retractor screw retaining pins 928, a right arm 932, and a left arm 936.

One of skill in the art may discern that the translation of torque provided to the proximal end 940 of the retractor screw 912 to movement of the distal ends 944 of the right arm 932 and left arm 936 comes from the movement of the retractor nut 908 within the housing 904. The rotating retractor screw 912 does not translate relative to the housing 904 as the retractor screw 912 spins within the housing 904 while retained by a pair of retractor screw retaining pins 928 that interact with a groove 948 near the proximal end 940 of the retractor screw 912.

Internal Retractor Inserter.

As indicated above, an internal retractor is reversibly connected to an internal retractor inserter and moved from the proximal end of the channel retractor towards the distal end of the channel retractor (possibly even beyond the distal end of the channel retractor). Once the distal portions of the internal retractor arms 848, 944 are positioned as desired in the opening in the psoas muscle, the internal retractor inserter releases the internal retractor and then the internal retractor inserter may be removed from the channel retractor. When there is no longer a need for the internal retractor, the distal end of the internal retractor inserter may be inserted through the channel retractor to engage the internal retractor. Once engaged, force provided from outside the patient is used to bring the distal ends of the arms of the internal retractor back together at least sufficiently to allow the internal retractor to be withdrawn with the distal tip of the internal retractor inserter through the channel retractor and out of the patient.

Figure 31:
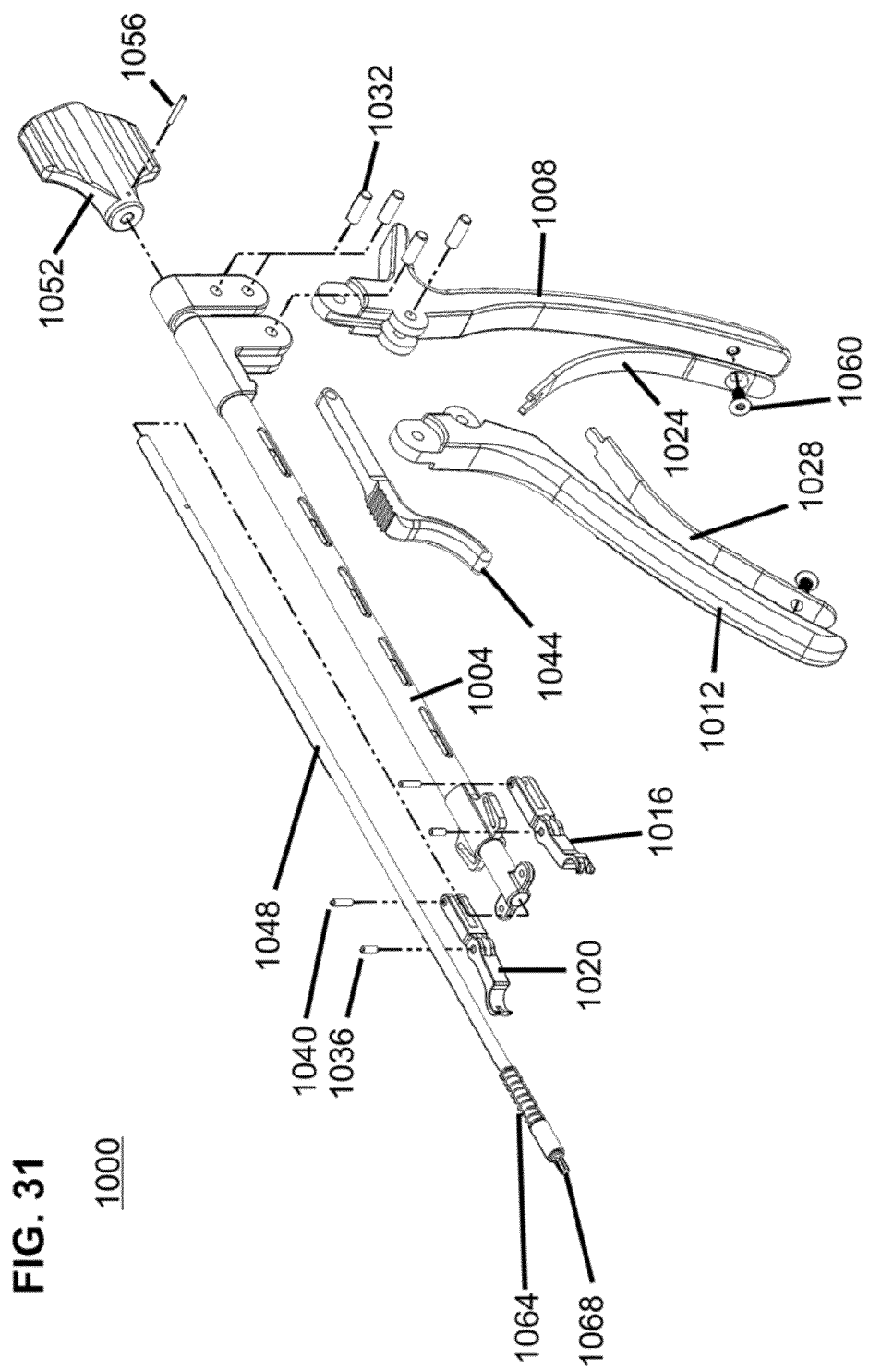
FIG. 31 is an exploded diagram of an internal retractor inserter.

As part of an overall effort to enable this disclosure an example of a suitable internal retractor inserter 1000 is provided in FIG. 31. Those of skill in the art will be able to make other internal retractor inserters that provide suitable functionality for a given internal retractor design. The parts shown in FIG. 31 are: a tube subassembly 1004, a back handle 1008, a front handle 1012, two grasping jaws 1016 and 1020, a back leaf spring 1024, a front leaf spring 1028, a set of four pin type A 1032, a pair of pin type B 1036, a pair of pin type C 1040, a locking spur 1044, a hex rod 1048, a wing knob 1052, a pin type D 1056, a pair of screws 1060, and a compression spring 1064.

Figure 32:
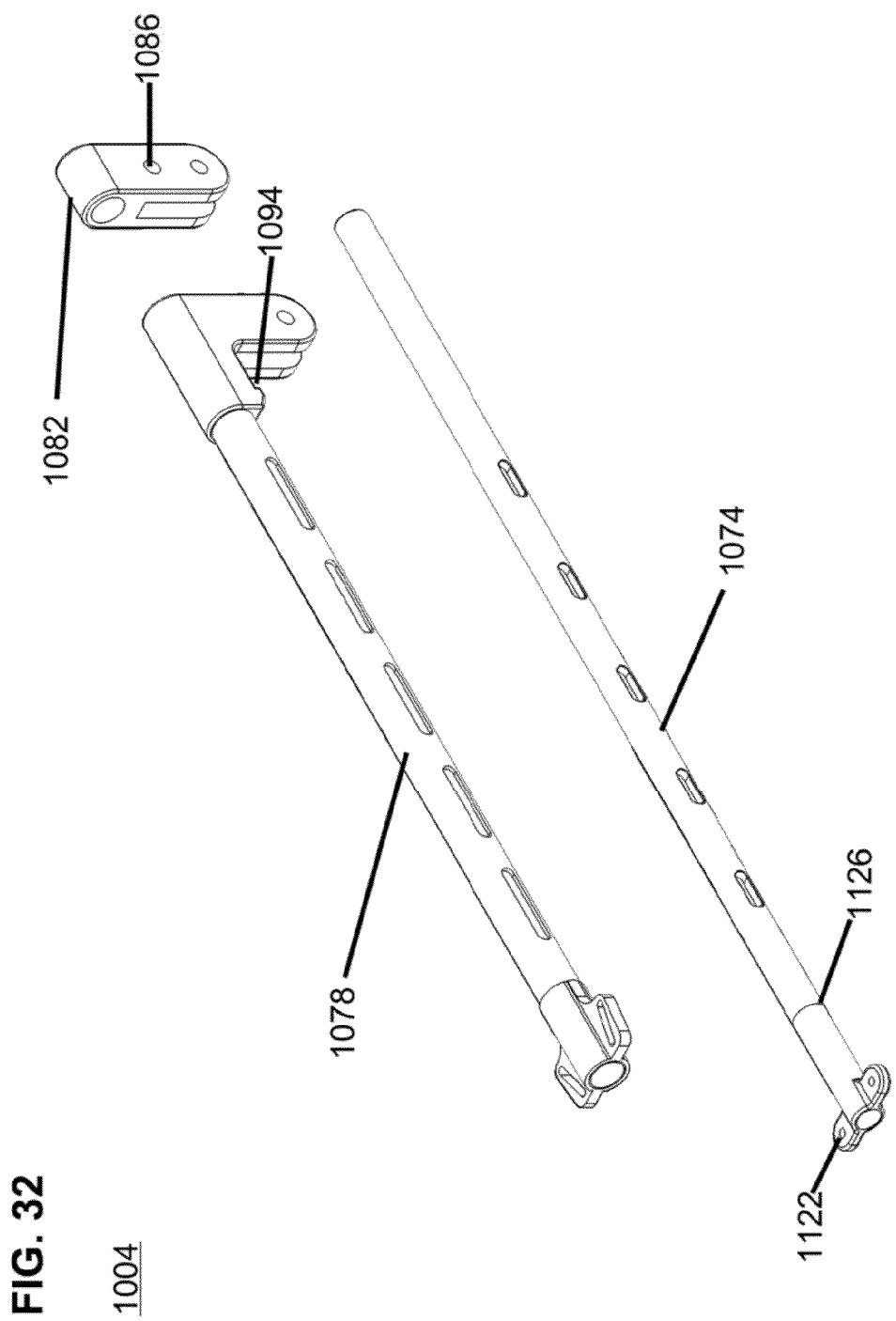
FIG. 32 provides details on the components in the tube subassembly portion of the internal retractor inserter.

FIG. 32 provides details on the components in the tube subassembly portion of the internal retractor inserter including: a tube subassembly 1004, an inner tube subassembly 1074, an outer tube subassembly 1078, and an inner tube collar 1082.

As the distal tip 1068 of the hex rod 1048 makes initial contact with the retractor screw 824 or 912, the hex rod 1048 is moved proximally within the internal retractor inserter assembly 1000 and thus compresses the compression spring 1064 (FIG. 31) which is trapped between a flange (hidden in FIG. 31 by compression spring 1064) of the hex rod 1048 at the distal end of the compression spring 1064 and a flange 1126 on the inner tube subassembly 1074. Adding a spring force to the hex rod 1048 allows the distal tip 1068 of the hex rod 1048 to move distally and stay engaged with the proximal end of the retractor screw 824 for internal retractors 800 that have retractor screws 824 that translate relative to the retractor housing 804. Note, when the internal retractor inserter 1000 is used with an internal retractor 900 that uses a retractor screw 912 that rotates but does not translate relative to the internal retractor housing 904, the compression screw 1064 remains compressed but the internal retractor inserter 1000 is effective for delivering, deploying, and retrieving the internal retractors 900 of this type.

While the hex rod 1048 has a distal tip 1068 with a hexalobe drive, other driver engagement configurations may be used provided they are used on both the distal end of the inserter and the proximal end of the retractor screw. Hexalobe heads are desirable as they provide a secure connection with a reduced likelihood of stripping.

Figure 33:
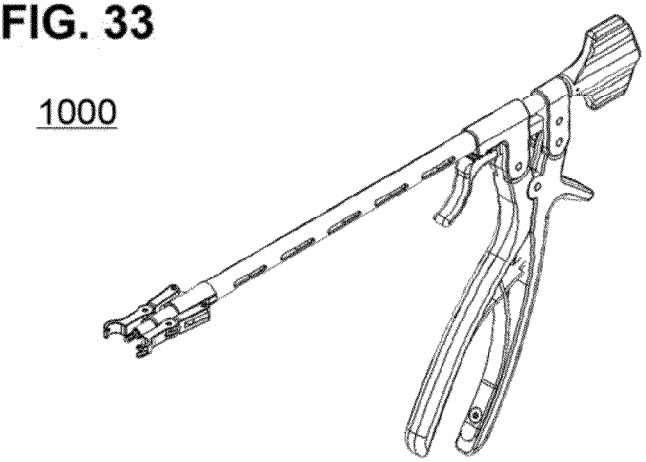
FIG. 33 shows a complete internal retractor inserter in a closed position.
Figure 34:
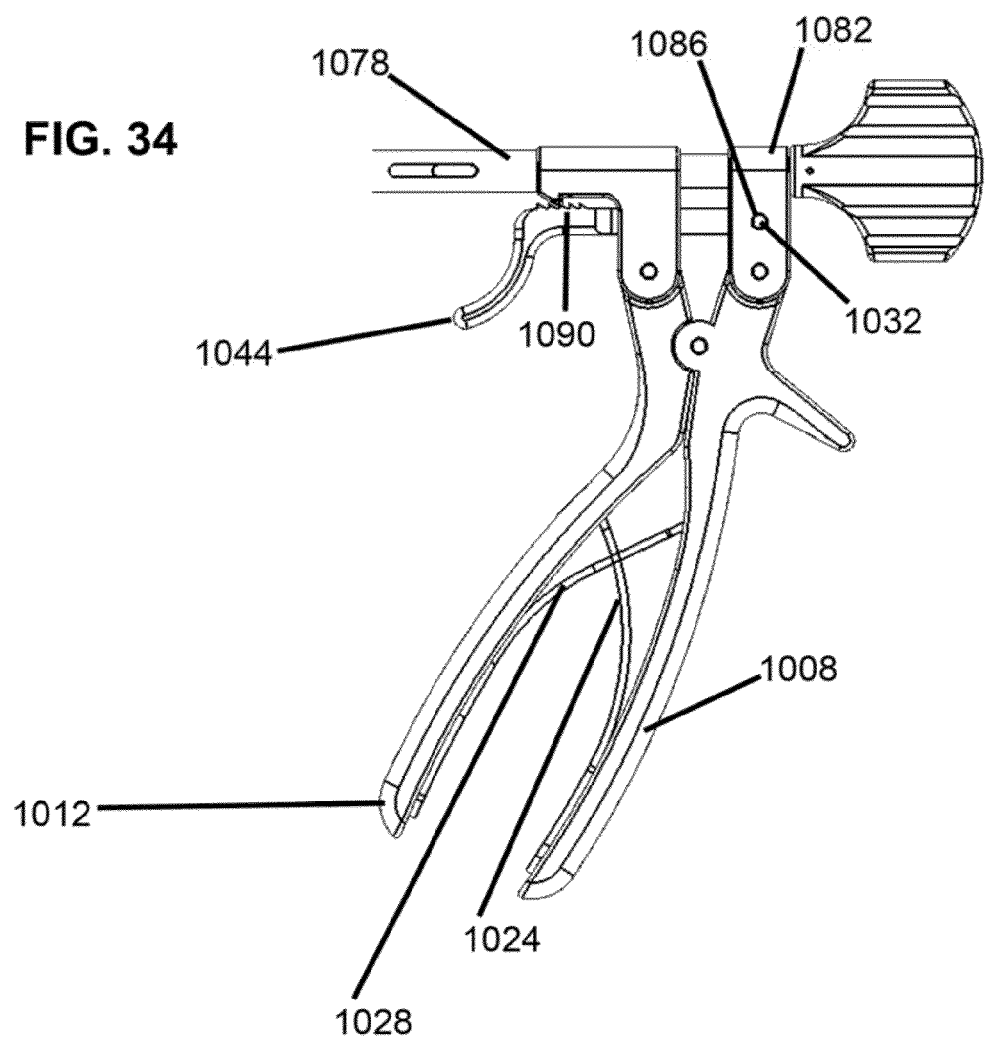
FIG. 34 shows a side view of the handle end of the internal retractor inserter shown in FIG. 33.

A complete internal retractor inserter 1000 is shown in FIG. 33 in a closed position. FIG. 34 shows a side view of the handle end of the internal retractor inserter 1000 shown in FIG. 33. These figures show front handle 1012 and back handle 1008 drawn together against the force from front leaf spring 1028 and back leaf spring 1024 and held by locking spur 1044.

The locking spur 1044 is pinned to the top bore 1086 in the inner tube collar 1082 and thus may rotate relative to the pin type A 1032. The locking spur 1044 has a series of saw tooth projections 1090. A flat face of any one of these saw tooth projections 1090 on locking spur 1044 may engage a projection 1094 (best seen in FIG. 32) of the outer tube subassembly 1078 to prevent distal movement of the outer tube subassembly 1078 relative to the inner tube subassembly 1074 (FIG. 32). As the internal retractor inserter 1000 is moved to make the long axis of the internal retractor inserter 1000 substantially vertical to prepare for travel through the channel retractor, the locking spur 1044 is apt to engage and lock the outer tube assembly 1078. If this does not happen, the user may nudge the locking spur 1044 into position. Subsequent movement to release the locking spur 1044 releases the outer tube subassembly 1078.

Figure 35:
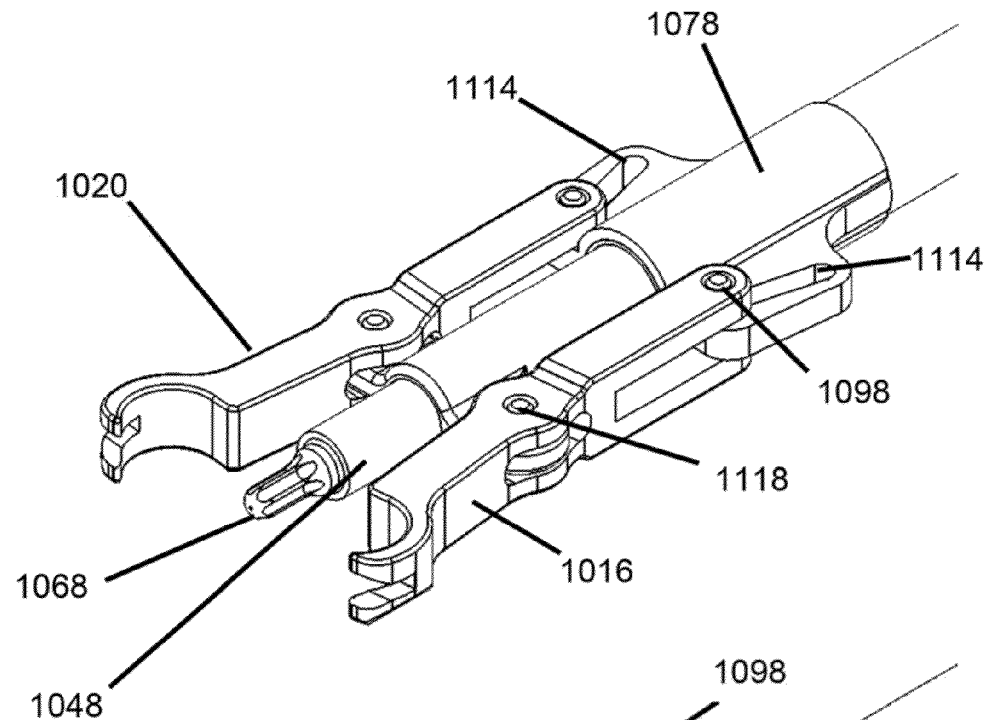
FIG. 35 shows the distal end of internal retractor inserter in the open position.
Figure 36:
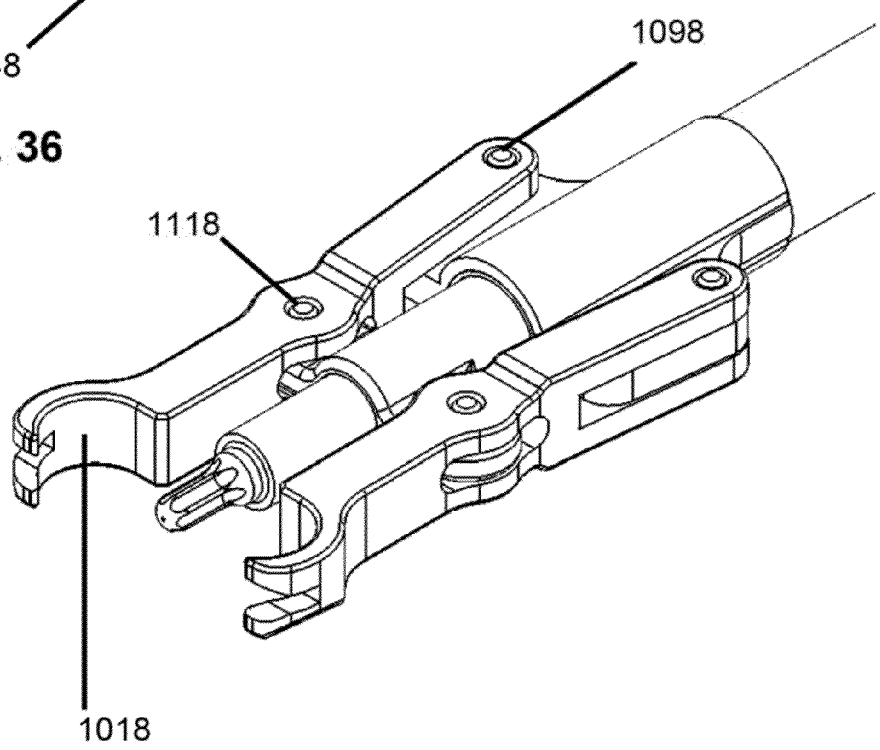
FIG. 36 shows the distal end of internal retractor inserter in the closed position.

FIG. 35 shows the distal end of internal retractor inserter 1000 in the open position. FIG. 36 shows the distal end of internal retractor inserter 1000 in the closed position. Both figures show the pair of grasping jaws 1016, 1020 and the distal end 1068 of the hex rod 1048. One can see that the distal end 1068 of the hex rod 1048 has a tip 1068 to engage with a corresponding portion of the proximal end of the internal retractor so that rotation of the hex rod 1048 by the wing knob 1052 (FIG. 31) provides torque to the retractor screw 912 or 824 to cause movement outward or inward of the distal portions 848, 944 of the retractor arms 932, 936 or 808, 812.

The grasping jaws 1016, 1020 each have a concave end portion 1018 that is adapted to engage a rounded corner 952 such as found on internal retractors 800 or 900. Note that one of skill in the art will recognize that an internal retractor inserter may be used with a range of internal retractor assemblies or other assemblies providing that the grasping jaws are compatible with accessible rounded corners for holding the assembly and the retractor screw has a compatible proximal end for engagement with the distal end 1068 of the hex rod 1048.

Operation of the Grasping Jaws.

Continuing to view FIG. 34, FIG. 35, and FIG. 36, squeezing the front handle 1012 and back handle 1008 together against the resistance of the front leaf spring 1028 and back leaf spring 1024 moves the outer tube subassembly 1078 in the distal direction to move the pinned proximal ends 1098 of the grasping jaws 1016, 1020 apart as the pinned proximal ends 1098 follow angled slots 1114 in the outer tube subassembly 1078. This movement of the pinned proximal ends 1098 rotates the grasping jaws 1016, 1020 around pivot points 1118 where pinned to bores 1122 (FIG. 32) in the inner tube subassembly 1074. Pivoting moves the respective concave end portions 1018 inward to engage a rounded corner 952 such as found on internal retractors 800 or 900.

As explained above, engagement of the locking spur 1044 with the outer tube subassembly 1078 prevents the outer tube subassembly 1078 from moving under force of the leaf springs 1024, 1028 back to the original position. Thus, through use of the locking spur 1044, the grasping jaws 1016, 1020 stay engaged with the rounded corners 952 of the housing 804, 904 of the internal retractor assembly 800, 900 until the locking spur 1044 is released.

Process of Expanding Psoas Muscle with an Internal Retractor Assembly.

After an internal retractor assembly has been engaged with an internal retractor inserter and moved with the distal tip of the internal retractor inserter so that the distal portions of the internal retractor arms are positioned as desired in the opening in the psoas muscle, the internal retractor assembly may be used to increase the size of the opening in the psoas muscle. Sweeping the distal tips of the internal retractor arms may help seat the distal tips of the internal retractor arms against the annulus of the targeted disc space. Optionally, a 90 degree nerve retractor may be used to maintain the split in the psoas muscle while inserting the internal retractor assembly.

Fluoroscopic images may be used to confirm the placement of the distal tips of the internal retractor arms relative to patient anatomy and a set of radio-opaque markers placed in the distal end of the channel retractor.

Once in position, the internal retractor arms 932, 936 or 808, 812 may be expanded by rotating the wing knob 1052 (FIG. 31) which rotates the hex rod 1048 to rotate the proximal end 858, 940 of the retractor screw 824 or 912. This process continues until the sides of the internal retractor arms 932, 936 or 808, 812 abut against the interior wall of the channel retractor (or a hard stop is reached with the mechanism in the internal retractor assembly 800 or 900).

The placement of the internal retractor assembly after expansion may be reviewed via fluoroscopy and through direct visualization from the proximal end of the channel retractor. The distal portions of the retractor arms 932, 936 or 808, 812 should be over the disc space and perpendicular with the endplates of the two vertebrae adjacent to that disc space.

The movement of the distal ends 944 or 848 (FIG. 25) of the retractor arms 932, 936 or 808, 812 can be varied by the design and scale of the retractor inserter assembly. For sake of scale, it may be useful to know that an internal retractor assembly may be configured to open approximately thirty six millimeters at the distal ends 944 or 848.

The internal retractor inserter 1000 may be removed by releasing the locking spur's 1044 engagement with the outer tube subassembly 1078 to allow the spring pressure from the leaf springs 1024, 1028 operate to return the internal retractor inserter grasping jaws 1016, 1020 to their original open position.

After completion of the medical procedure on the spine, the distal tip 1068 of the internal retractor inserter 1000 may be inserted into the channel retractor and re-engaged with the internal retractor assembly 800, 900. For internal retractors assemblies 800 where the retractor screw 824 translates relative to the internal retractor housing 804, the retractor screw 824 will be in a distal position and thus the compression spring 1064 for the internal retractor inserter 1000 will become more compressed as the retractor screw 824 is moved to move the distal ends 848 of the retractor arms 808, 812 together. After the distal ends 848 of the retractor arms 808, 812 are drawn back together, the internal retractor assembly 800 may be withdrawn through the channel retractor with the engaged distal tip 1068 of the internal retractor inserter 1000.

Use of a Linkage Jack.

As an alternative to the use of a tube in tube process to push extended retractors apart to enlarge an opening in tissue such as the psoas muscle, one could use a jack mechanism to push apart a pair of extended retractors by pushing the extended retractors up against the inner wall of the channel retractor.

Figure 37:
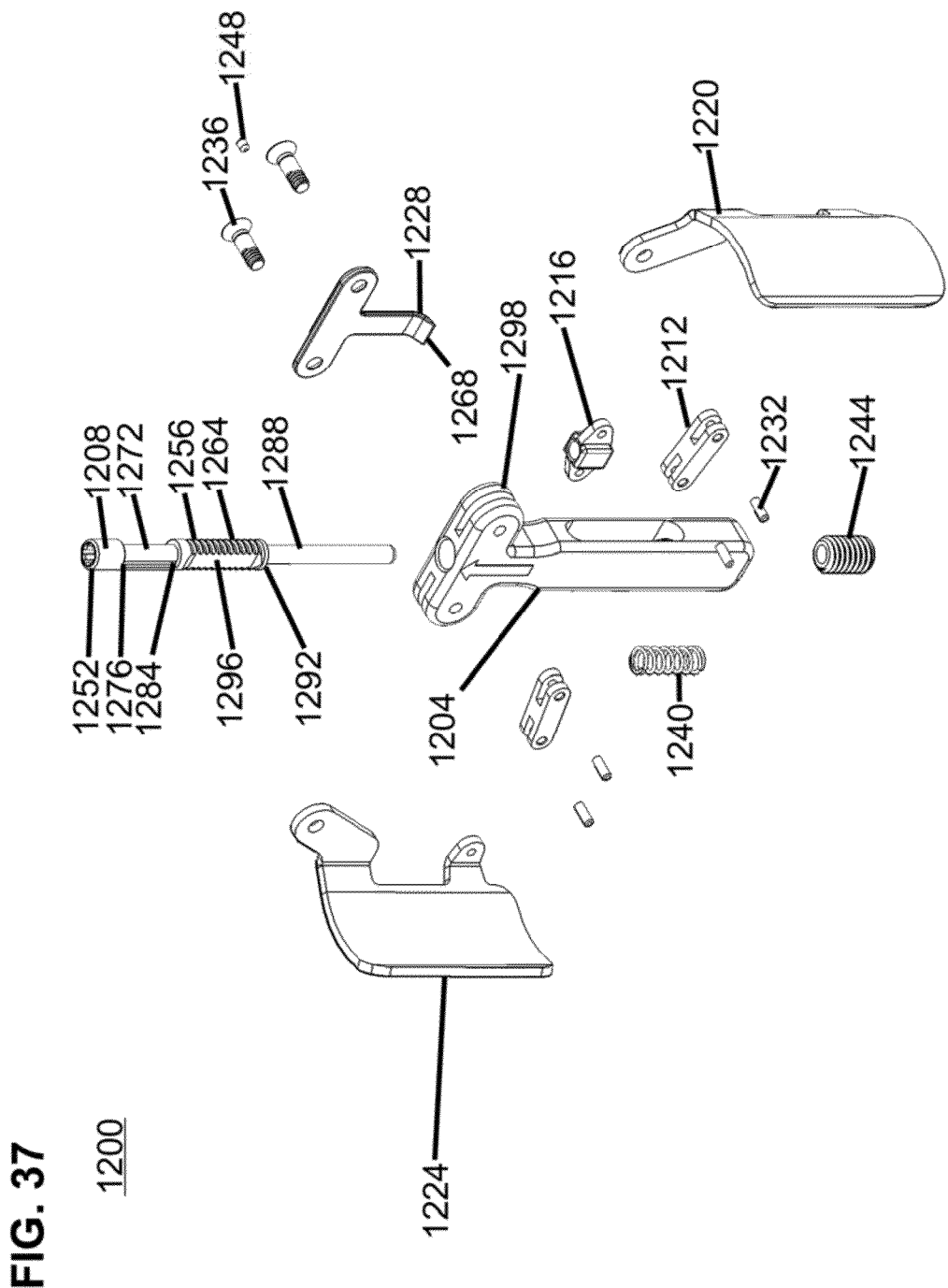
FIG. 37 shows an exploded view of one linkage jack assembly.

FIG. 37 shows an exploded view of one linkage jack assembly 1200. Notice that the linkage jack assembly 1200 does not have blade tips that extend distal of the rest of the linkage jack assembly 1200. The components shown in FIG. 37 are: a housing 1204, a ratchet tube 1208, a pair of support arms 1212, a nut 1216, a left jack arm 1220, a right jack arm 1224, a pawl 1228, a set of four support arm fixation pins 1232, a pair of pawl screws 1236, a compression spring 1240, a pre-load adjustment screw 1244, and a location pin 1248.

Figure 38:
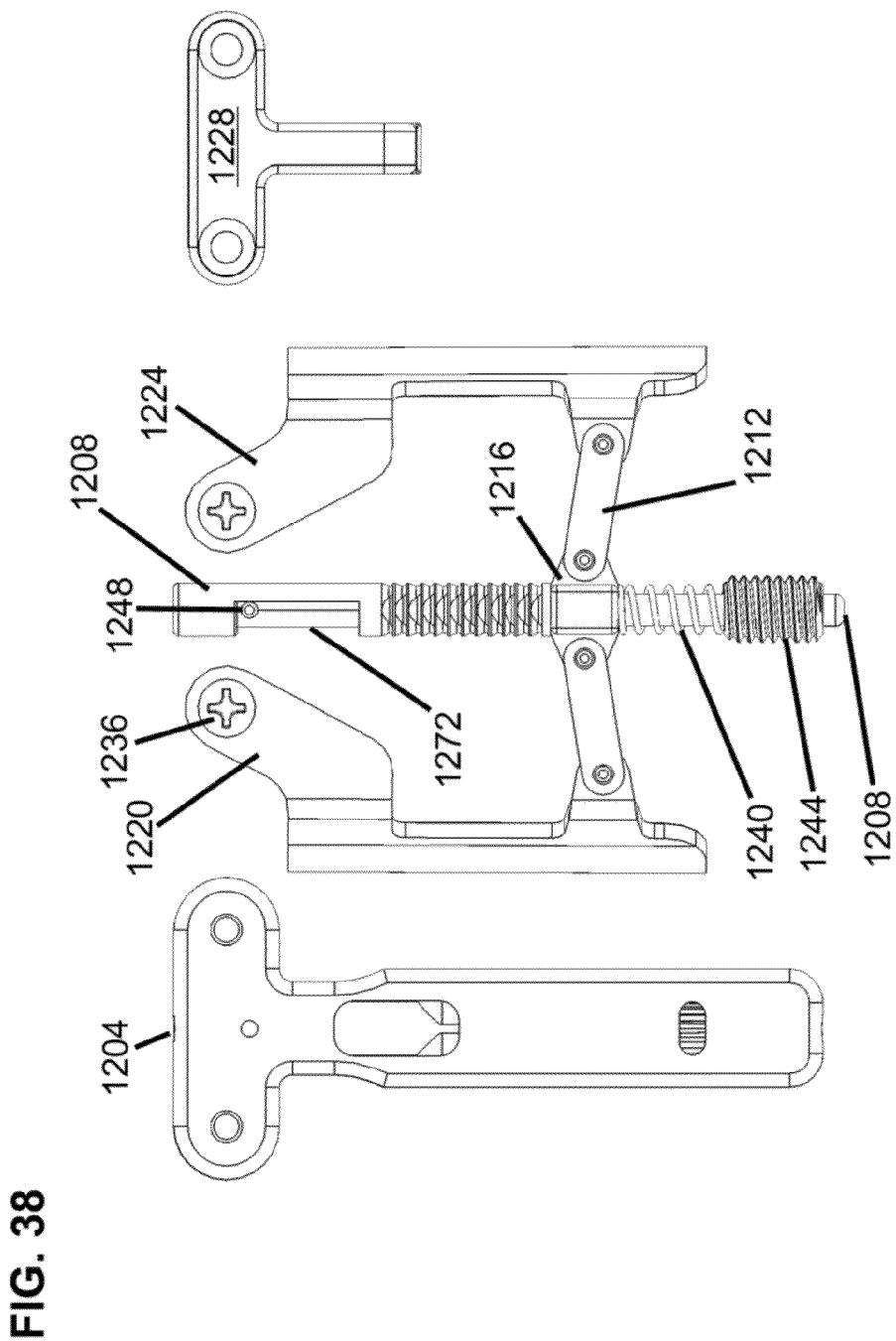
FIG. 38 is a partially exploded view in that only the housing and the pawl have been moved from a linkage jack assembly with jack arms expanded.

FIG. 38 is a partially exploded view in that only the housing 1204 and the pawl 1228 have been moved from a linkage jack assembly 1200 with jack arms 1220 and 1224 expanded. Reviewing FIG. 37 and FIG. 38, the operation of the support arms 1212 and the jack arms 1220, 1224 is similar to the operation of the analogous parts in the internal retractor 1000 described above. The ratchet tube 1208 has a proximal end 1252 with a driver engagement section, such as a female hexalobe connection. The ratchet tube 1208 has a ratchet section 1256 with a set of sawtooth projections 1264 with flat faces on the proximal side. The sawtooth projections 1264 engage with the distal end 1268 of the pawl 1228 so that pressure from a driver may move the ratchet tube 1208 in a distal direction, but the pawl 1228 prevents movement of the ratchet tube 1208 in the proximal direction. The location pin 1248 fits through a bore in the housing 1204 (bore not shown) and engages a recessed section 1272 of the ratchet tube 1208 between a proximal projection 1276 and a distal projection 1284 to limit the range of motion of the ratchet tube 1208 relative to the housing 1204. The jack arms 1220 and 1224 are pinned by unthreaded portions of pawl screws 1236 to the housing 1204.

The location pin 1248 is inserted into the housing 1204 before the pawl 1228 is attached to the housing 1204. The location pin 1248 limits the rotation the ratchet tube 1208 so one can remotely rotate the ratchet tube 1208 to place the ratchet tube 1208 into a first mode that engages with the pawl 1228 and a second mode that moves the ratchet tube 1208 distally to retract the jack arms 1220 and 1224.

The nut 1216 is not a traditional nut as nut 1216 is not threaded. A tubular distal portion 1288 of the ratchet tube 1208 fits through a bore in the nut 1216 and through the compression spring 1240 and at least partially through a bore in the preload adjustment screw 1244. The nut 1216 is thus trapped between the proximal end of the compression screw 1240 and the projection 1292 at the proximal end of the tubular distal portion 1288 of the ratchet tube 1208.

Pushing distally on the proximal end 1252 of the ratchet tube 1208 causes the ratchet tube 1208 to move distally relative to the housing 1204 and that pushes the nut 1216 distally to further compress the compression spring 1240. When the ratchet tube 1208 is pushed distally, the end of the ratchet tube 1208 may extend through the preload adjustment screw 1244. Moving the nut 1216 distally causes the support arms 1212 to move towards a perpendicular orientation with respect to a proximal/distal axis to move the jack arms 1220, 1224 outward. The position of the jack arms 1220, 1224 is maintained as the distal end 1268 of the pawl 1228 engages the ratchet section 1256 of the ratchet tube 1208.

To release the pawl 1228 and draw the jack arms 1220, 1224 together, the ratchet tube 1208 is rotated 180 degrees through rotation of the proximal end 1252 of the ratchet tube

1208. This rotation moves the ratchet section 1256 of the ratchet tube 1208 away from the distal end 1268 of the pawl 1228 and moves a flat surface 1296 in front of the distal end 1268 of the pawl 1208. The distal end 1268 of the pawl 1208 does not engage with the flat surface 1296 and the compression spring 1240 forces the nut 1216 upward which pushes the ratchet tube 1208 upward. As the nut 1216 moves upward, the support arms 1212 move inward and draw in the pair of jack arms 1220, 1224.

The preload adjustment screw 1244 allows a spring force from the compression spring 1240 to be increased before the ratchet tube 1208 is moved distally. Adjusting the preload adjustment screw 1244 can adjust the spring force applied to move the ratchet tube 1208 proximally when the ratchet tube 1208 is rotated to be free of the pawl 1228. One of skill in the art will recognize that the preload adjustment screw 1244 is an optional component as the spring force from compression spring 1240 may be adjusted through use of a bore through housing 1204 that does not extend all the way to the distal end so that the combination of bore depth and the properties of the compression spring 1240 can establish the preload on the compression spring 1240.

Linkage Jack Inserter.

Note a linkage jack assembly 1200 may be inserted by the internal retractor inserter 1000 discussed above, provided that the rounded corners 1298 of the housing 1204 can be grabbed by the grasping jaws 1016, 1020 of the internal retractor inserter 1000. If the hex rod 1048 is sized long enough, the hex rod 1048 will be driven proximally upon contact with the proximal end 1252 of the ratchet tube 1208. Pushing (rather than rotating) the wing knob 1052 will push the hex rod 1048 distally relative to the grasping jaws 1016, 1020 to cause the ratchet tube 1208 to move distally and be held there by the pawl 1228.

When the linkage jack assembly 1000 is to be returned to a non-expanded configuration, the wing knob 1052 may be rotated 180 degrees to place the flat surface 1296 of the ratchet tube 1208 adjacent to the distal end 1268 of the pawl 1228 which then allows the linkage jack compression spring 1240 to move the nut 1216 in the proximal direction and thus draw inward the jack arms 1220, 1224. Those of skill in the art will recognize that other drivers may be used to operate the linkage jack assembly 1200.

Those of skill in the art will recognize that the ratchet mechanism shown in connection with the linkage jack assembly 1200 could be used with an internal retractor and conversely, a screw mechanism could be used to deploy and retract the jack arms rather than a ratchet mechanism.

Figure 39:
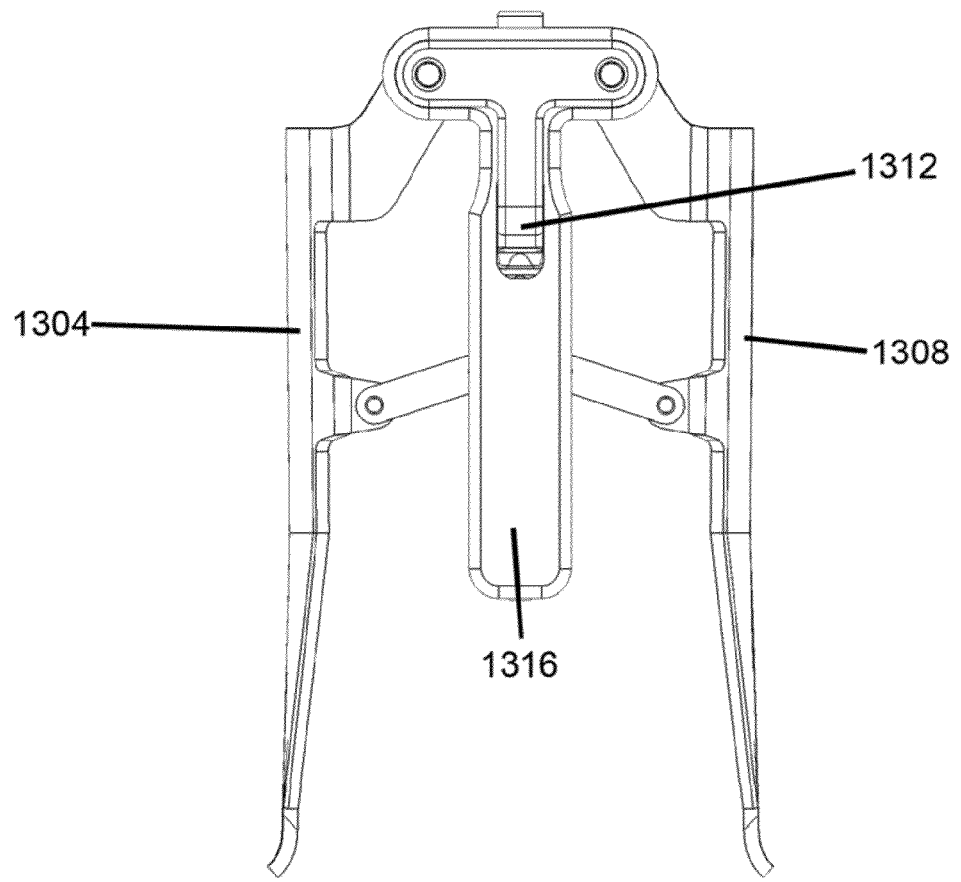
FIG. 39 illustrates an internal retractor with a pawl that is used to hold arms in an expanded position by interacting with a ratchet mechanism within a housing.

FIG. 39 illustrates an internal retractor 1300 with a pawl 1312 that is used to hold arms 1304 and 1308 in an expanded position by interacting with a ratchet mechanism within a housing 1316.

Process of Secondary Retraction Using a Linkage Jack.

Figure 40:
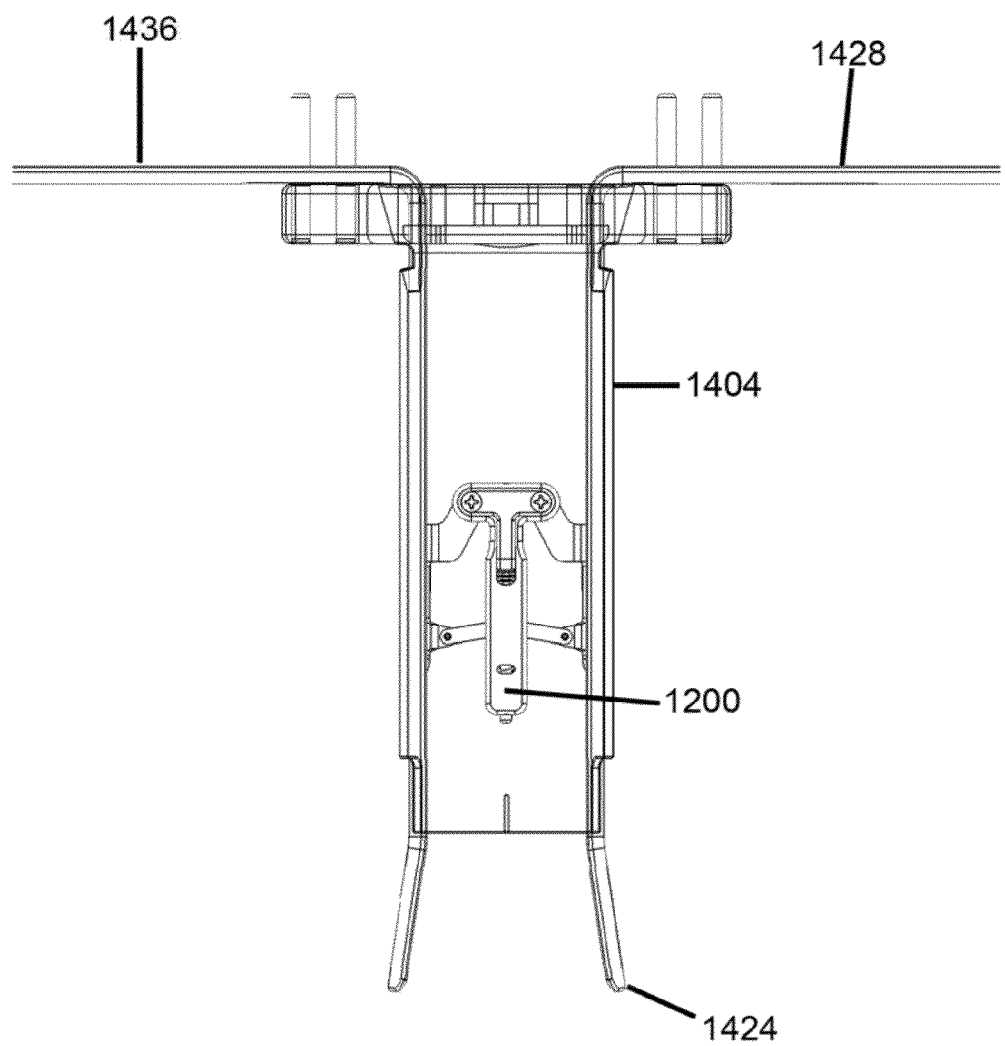
FIG. 40 provides a side view of a cross section of an assembly with linkage jack assembly in an extended position.

FIG. 40 provides a side view of a cross section of an assembly with linkage jack assembly 1200 in an extended position holding extended retractors 1428 and 1436 against an inner perimeter 1408 (FIG. 41) of channel retractor 1404. To provide a focus on the contents of the channel retractor 1404, the handle portions 1440 of extended retractors 1428 and 1436 are truncated in FIG. 40.

Figure 41:
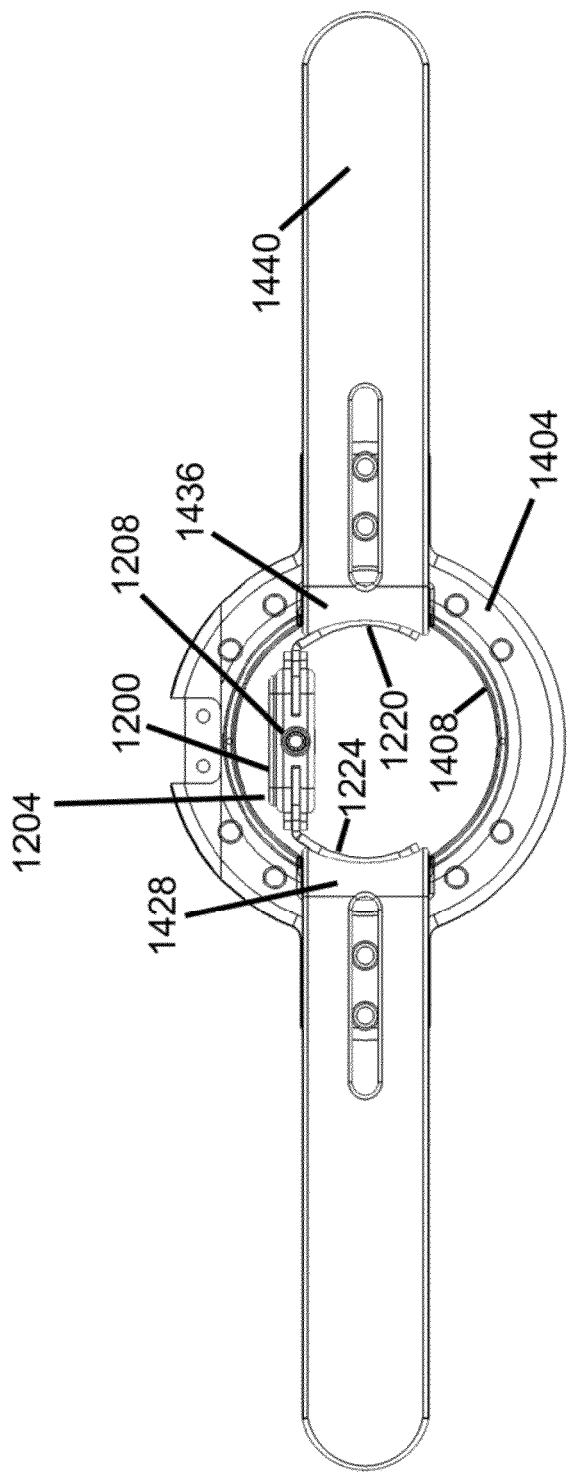
FIG. 41 shows a view looking distally through channel retractor of the assembly shown in FIG. 40.

FIG. 41 shows a view looking distally through channel retractor 1404 of the assembly shown in FIG. 40. Visible in FIG. 41 are linkage jack assembly 1200 including ratchet tube 1208, and jack arms 1220 and 1224 which are pressing extended retractors 1428 and 1436 against the inner perimeter 1408 of channel retractor 1404. Note that extended retractors 1428 and 1436 have elongated handle sections 1440.

The process of using the linkage jack assembly 1200 may be done as follows.

After creating a small opening through the psoas muscle with a dissector tool such as the angled Cobb dissector 176 (above), a nerve retractor tool such as a 90 degree nerve retractor may be inserted along the dissector to retract the muscle posteriorly. Alternatively, a Penfield or Cobb distractor may be used instead of the 90 degree nerve retractor.

A first extended retractor 1428 may be used to retract the psoas muscle anteriorly. As the muscle is retracted, the distal end 1424 of the extended retractor 1428 is maintained in contact with the annulus and the vertebral body. The extended retractor 1428 may be provided in more than one length. For example the extended retractor 1428 may be provided in two lengths, 165 millimeters and 205 millimeters. As noted above, the channel retractor 1404 may come in several lengths. The choice of length for use in a procedure is impacted primarily by the choice of channel retractor length but secondarily by the thickness of the psoas muscle as the extended retractor 1428 will need to extend through the channel retractor 1408 and the split psoas muscle to reach the spine. Depth markings on the angled Cobb dissector 176 or other tool may be helpful to judge insertion depth as may fluoroscopy.

While maintaining gentle pressure on the first extended retractor 1428, the 90 degree nerve retractor may be removed.

A second extended retractor 1436 may be inserted into the split psoas muscle to retract the psoas muscle posteriorly while maintaining contact with the annulus.

After engaging the linkage jack assembly 1200 with an appropriate insertion tool (such as internal retractor inserter 1000), insert the linkage jack assembly 1200 distally through a portion of the channel retractor 1404 to push the extended retractors 1428, 1436 outward. As noted above, the extended retractors 1428, 1436 may optionally be engaged with the channel retractor 1404 to limit movement of the extended retractors 1428, 1436 around the perimeter of the channel retractor 1404.

As the linkage jack assembly 1200 is advanced distally in the channel retractor 1404 towards the spine, the wedge shape of the linkage jack assembly 1200 causes the extended retractors 1428 and 1436 to move towards the walls of the channel retractor 1404 which moves the distal ends 1424 of the extended retractors 1428 and 1436 outward.

Once the linkage jack assembly 1200 is placed where desired in the channel retractor 1404, the linkage jack assembly 1200 may be operated to continue to push the extended retractors 1428 and 1436 towards the walls of the channel retractor 1404. This movement further expands the opening in the psoas muscle. As noted above, the linkage jack assembly may be actuated via a screw mechanism, or by pushing a ratchet mechanism. While frequently, the process to open linkage jack assembly will continue until the extended retractors 1428 and 1436 abut the inner perimeter 1408 of the channel retractor 1404, this is not required in all situations and a partial opening may be chosen.

FIG. 41 shows completed assembly with the internal retractor inserter (such as internal retractor inserter 1000) removed from the perspective of a surgeon looking distally through the channel retractor 1404 towards the surgical site. Notice that the widest part of the channel retractor 1404 is substantially open as the space between the two extended retractors 1428 and 1436 is occupied by the relatively thin linkage jack arms 1220, 1224 but the thicker linkage jack housing 1204 is not located between the two extended retractors 1428 and 1436 and thus does not impinge significantly on the access route being preserved near the longitudinal midline of the channel retractor 1404.

An alternative not shown is a driver tool for use with a linkage jack 1200 that remains connected to the ratchet tube 1208 and leaves a shaft from the driver tool above the ratchet tube 1208 rather than disconnect the linkage jack 1200 from the driver.

Material Choices.

One choice for material for use in the various channel retractors shown above is medical grade Radel® R5500 (Polyphenylsulfone). This material can withstand sterilization techniques such as Ethylene oxide (EtO) gas, radiation, steam autoclaving, dry heat, and cold sterilization. Other desirable attributes are that the material is dimensionally stable and may be marked with lasers. One of skill in the art will recognize that other materials could be used instead of Radel® R5500. PEEK is another material choice that may be used as it is radiolucent. Composites of carbon fibers and polymers may be selected for creating channel retractors or extended retractors.

Provision of Therapy after Creating an Access Channel.

After creating an access channel first to the psoas muscle then through the psoas muscle using any of the methods described above, a lateral portion of the spine may be accessed for the provision of therapy. One form of therapy is to fuse two adjacent vertebrae together. Some surgeons provide the therapy of spinal fusion without using an implant. Other surgeons use a spinal implant in the process of providing therapy to achieve spinal fusion. Spinal fusion typically involves the use of osteogenic, osteoconductive, or osteoinductive material (bone graft). Bone graft is the material that is used to promote bone growth and forms the scaffold that bridges the adjacent vertebral bodies comprising a motion segment in the spine. Two fused vertebrae do not move with respect to one another.

It is useful to have one name for the variety of materials used to promote fusion. Thus, fusion promoting materials include osteogenic, osteoconductive, and/or osteoinductive material including bone graft material whether the material is autograft or allograft and various bone graft substitutes or bone graft extenders. Various techniques for promoting effective fusion of adjacent vertebrae are well known to those of skill in the art so a minimal summary is sufficient for this document.

Preparation of Disc Space

One process to promote fusion is to conduct a discectomy to remove nucleus pulposus of the disc and to abrade the vertebral endplates adjacent to the disc space as bleeding from the endplates promoted bone growth and fusion. An interbody implant (sometimes called a fusion cage) may be introduced into the disc space along with quantities of one or more fusion promoting materials. Frequently, the nature of the access channel used to access the disc space will impact the dimensions of the cage that may be delivered to the disc space.

Frequently, tools are inserted that serve as trial implants. These tools provide guidance to the surgeon on the most appropriate size of implant to use for a particular patient's anatomy for a particular access route. The position of the trial implant may be assessed via fluoroscopy. One dimension that may be ascertained by trial devices is the appropriate choice of height for the implant. In some instance it may be that assertive insertion of a series of progressively larger trial devices will serve to increase the distance between adjacent vertebrae (vertebral distraction) which may be a desired outcome of the surgical intervention.

There are other forms of therapies that may be provided to the spine and the methods of providing access set forth above are not limited to the provision of any one particular therapy.

Implants.

Figure 42:
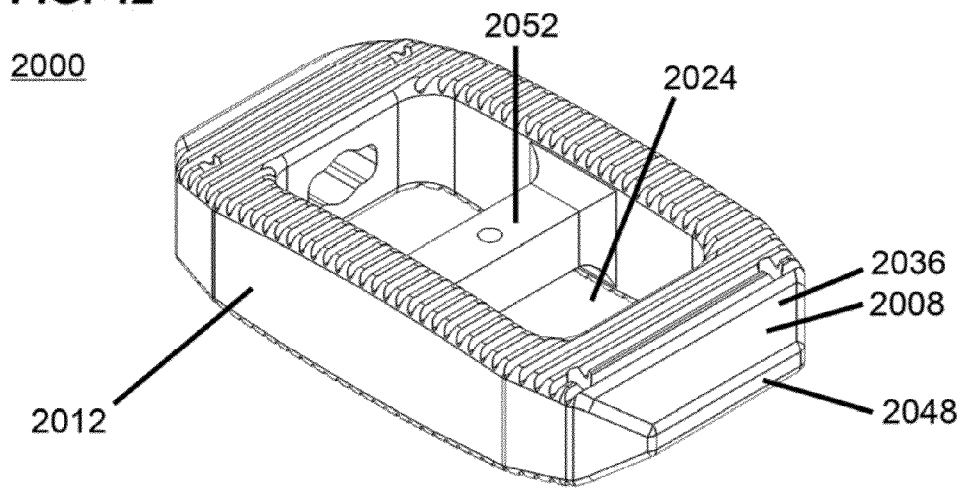
FIG. 42 is a front perspective view of an implant.
Figure 43:
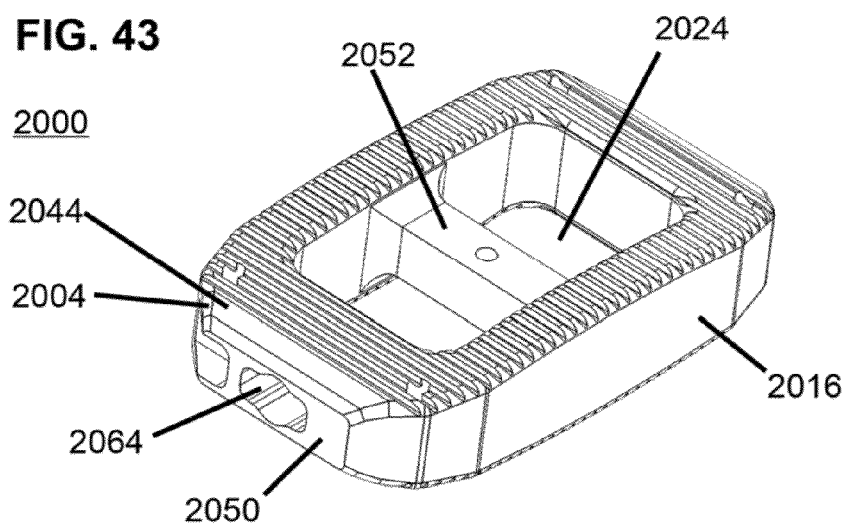
FIG. 43 is a rear perspective view of an implant.
Figure 44:
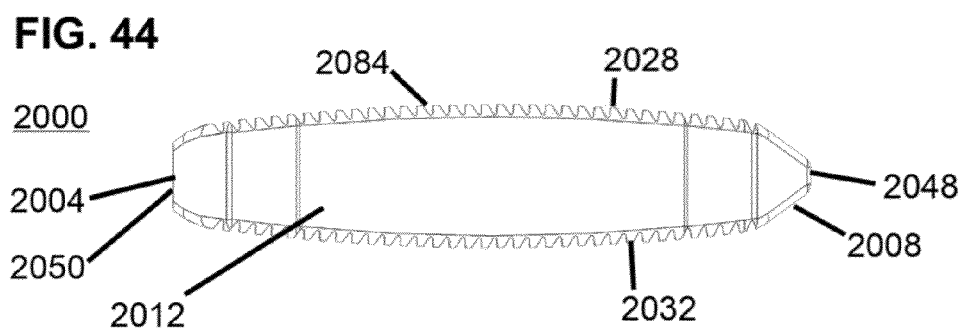
FIG. 44 is a side view of an implant.

FIG. 42, FIG. 43 and FIG. 44 show a front perspective view, a rear perspective view, and a side plan view of an implant 2000 that may be delivered through the psoas muscle and into a disc space as part of surgery to create fusion of two adjacent vertebrae from a motion segment.

More specifically, these three figures show an implant 2000 for positioning in a motion segment between a cephalad vertebra and an adjacent caudal vertebra. The implant 2000 having a trailing edge or end portion 2004 that may be engaged by an implant movement tool. The term implant movement tool includes: a tool designed to place an implant into a disc space; any tool used to reposition the implant within the disc space, and a tool designed to remove a previously placed implant from a disc space. These tools may be one in the same, but often the tools for removing an implant that has been in place since an earlier surgical procedure may be different as bone ingrowth may make movement more difficult.

The figures show a leading edge or end portion 2008 on the opposite side of the implant from the trailing end portion 2004. The leading end portion 2008 and the trailing end portion 2004 are connected by a first connecting wall 2012 and a second connecting wall 2016. The combination of the leading end portion 2008, first connecting wall 2012, trailing end portion 2004, and second connecting wall 2016 form a perimeter frame that partially encloses a space that may be called the fusion cavity 2024. The fusion cavity 2024 may be filled or partially filled with fusion promoting materials. The fusion cavity 2024 may be filled with fusion promoting materials before delivery to the disc space. Additional fusion promoting materials may be provided to the fusion cavity 2024 and to the disc space after the delivery of the implant 2000 to the disc space.

A cephalad side 2028 of the implant 2000 is adapted to make contact with an endplate of the more cephalad of the two adjacent vertebrae. The opposite side of the implant is the caudal side 2032 intended to make contact with an endplate of the more caudal of the two adjacent vertebrae. In some implants, the two vertebral sides, the cephalad side 2028 and the caudal side 2032 of the implant 2000 are mirror images. These implants 2000 are sometimes called parallel implants even if the curved sides are not parallel to one another. Given an appropriate tool to deliver the implant 2000, it is possible that either side of a parallel implant could become the cephalad side.

Other implants seek to impose a correction to the curvature of the spine by having a wedge shape. In order to provide the wider part of the wedge where it is needed the orientation of the implant for a particular delivery route is limited.

One of skill in the art will recognized that part of the sloped faces of the leading and trailing ends (discussed below) will not make contact with the vertebral endplates.

The cephalad side 2028 will contact the cephalad side of the first connecting wall 2012 and the cephalad side of the second connecting wall 2016. The caudal side 2032 will have the corresponding parts.

Notice that in both the leading edge portion 2008 and the trailing end portion 2004 there are a front quadrilateral pyramidal frusta 2036 and a back quadrilateral pyramidal frusta 2044 with rounded edges. Thus, a leading face 2048 and a trailing face 2050 are vertical faces.

A cross bar 2052 may be included in the implant 2000 to augment the structure. The cross bar 2052 may be sized so that the cross bar 2052 is not part of the cephalad side 2028 that makes contact with the vertebra or the caudal side 2032 that makes contact with the vertebra as the thickness of the cross bar 2052 in the cephalad caudal direction is less than the thickness of the first connecting wall 2012 and the second connecting wall 2016. By having almost the entire cross bar 2052 thinner than the connecting walls 2012, 2016, fusion promoting material may be placed on all four sides of the cross bar 2052 to facilitate bone growth to fuse the two vertebrae.

The fusion cavity 2024 allows bone growth through the fusion promoting material to connect the cephalad vertebral endplate to the caudal vertebral endplate. Optionally, a series of one or more passages (not shown) connect the fusion cavity 2024 from the inner side of a connecting wall to an outer side of the connecting wall. These passages may have bone ingrowth, particularly if packed with fusion promoting material. Likewise a non-circular bore 2064 in the trailing end portion 2004 may provide another connecting passageway for the bone ingrowth into the fusion cavity 2024.

FIG. 45 is a top view of implant 2000. FIG. 46 is a front view of implant 2000. The implant 2000 may include a set of markers 2068 that are more radio-opaque than the material used for creating the implant 2000. The use of relatively opaque markers 2068 allows the markers 2068 to show up clearly on the fluoroscopic view to allow the placement of the implant 2000 to be judged as the implant 2000 is intended for delivery with a specific orientation with respect to the patient's anatomy.

One radio-opaque material that may be used for markers 2000 is tantalum, although other materials may be used. The markers used in the implant 2000 are a set of four corner markers 2072 which are rods oriented vertically (will become the cephalad/caudal direction) and a cross bar marker 2076 located in the center of the cross bar 2052. Other marker sets may be used. For example, a three rod marker set could be used with a pair or vertical (cephalad/caudal) rods near the intersection of each of the connecting walls 2012, 2016 near the start of the trailing end portion 2004 and a third rod running across the leading end portion 2008 (perpendicular to the two vertical rods). (See FIG. 55 and FIG. 56 discussed below.)

As described in more detail below, the implant 2000 may be provided with a set of anti-migration features 2084 that engage the vertebral endplates to resist movement of the implant 2000 towards the place where the implant was introduced. Thus the anti-migration features 2084 provide more resistance to movement towards the trailing edge 2004 of the implant 2000 than resistance towards the leading edge 2008 of the implant 2000.

FIG. 47 shows a cross section of implant 2000 through the midline of the cross bar 2052 (taken along the cephalad/caudal and anterior/posterior plane). The cross bar 2052 connects the first connecting wall 2012 to the second connecting wall 2016. The cross bar 2052 may have a cross bar flare 2088 at either end to flare into the connecting walls 2012, 2016. As the cephalad/caudal thickness of the cross bar 2052 is less than the cephalad/caudal thickness of the connecting walls 2012, 2016 adjacent to the cross bar 2052, there is space for fusion promoting material above and below the cross bar 2052. The cross bar marker 2076 may be a rod or some other shape such as an implanted sphere. The cross bar marker 2076 rod could be shorter than the rods used for the corner markers 2072. While the orientation of the cross bar marker 2076 may be vertical as shown, cross bar markers could be placed in the anterior/posterior direction or the distal/proximal direction. Placement of the cross bar marker 2076 approximately half-way along the distal/proximal axis of the implant 2000 allows the cross bar marker 2076 to be used via an anterior/posterior fluoroscopic image to align the implant 2000 with the spinous process and check the implant orientation. Note that when the implant 2000 is properly aligned, the closest corner markers 2072 will be aligned with a corresponding pair of corner markers 2072 in an anterior/posterior fluoroscopic image.

FIG. 48 shows a view of the trailing end portion 2004 of implant 2000 with the four sloped faces 2092 of the quadrilateral pyramid frusta 2044 surrounding the trailing face 2050. The edges 2080 between the four sloped faces 2092 are rounded. While the edges between the four sloped faces 2092 and the trailing face 2050 are not rounded, these edges could be rounded analogous to the rounded edges between a leading face 2048 and the four sloped faces 2096 on the leading end portion 2008 shown in front plan view in FIG. 46.

FIG. 48 shows the non-circular bore 2064 and the lateral engagement feature 2096 that may be used with an implant movement tool. One of skill in the art will recognized that additional lateral engagement features may be added to the trailing edge portion 2004. It is preferred that the lateral engagement feature 2096 be sufficiently deep that the implant movement tool may engage with the lateral engagement feature 2096 so that an implant 2000 engaged with an implant movement tool is not wider than the maximum width of the implant 2000 so that the difference between the maximum width of the implant 2000 and the delivery channel width may be minimized.

Lordotic Implants.

In some instances the implant is not a parallel implant but may have a difference in average cephalad/caudal height along the first connecting wall compared with the average height of the second connecting wall. When inserted laterally, this difference in height from anterior to posterior helps maintain a lordotic angle in the spine. The implant may be designed to have a greater height on the anterior portion of the disc space than on the posterior portion of the disc space. Thus instead of a zero degree slope between the outer edge of the first connecting wall to the second connecting wall, there may be a slope in the range of something more than zero to about twelve degrees. A six degree lordotic angle may be suitable for many patients requiring this correction.

Figure 49:
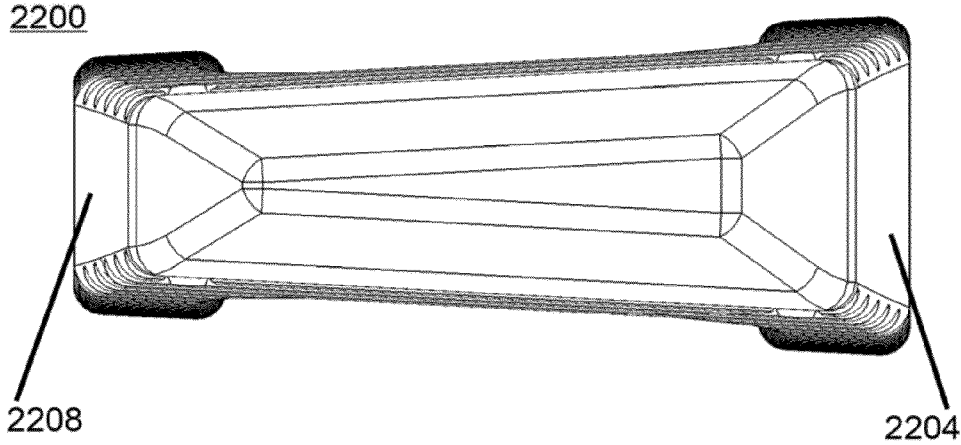
FIG. 49 shows a front plan view of an implant with a six degree lordotic angle.
Figure 50:
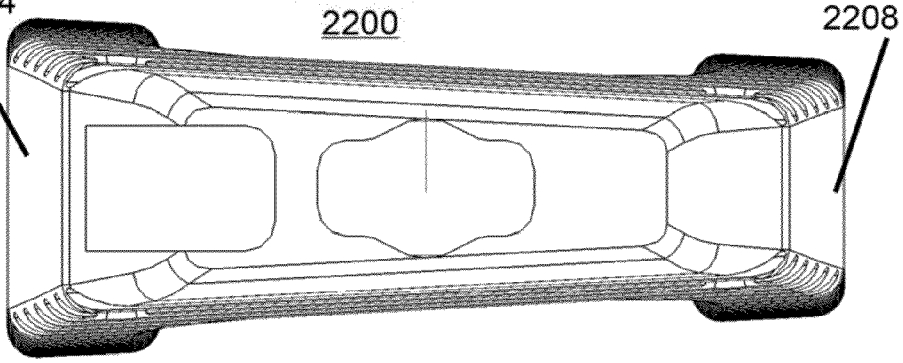
FIG. 50 shows a rear plan view of the implant from FIG. 49.
Figure 51:
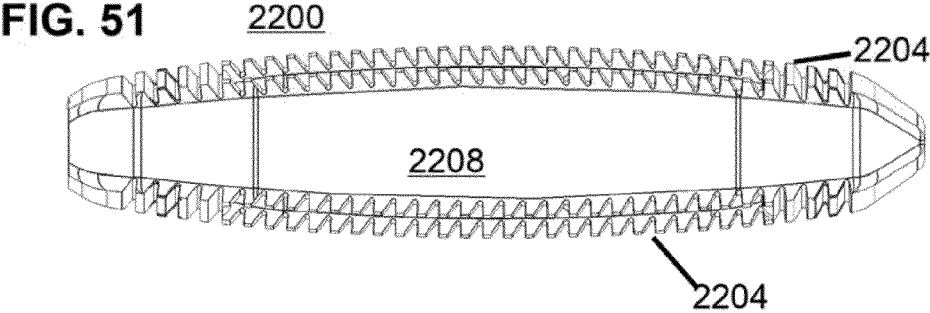
FIG. 51 is a side view of the implant from FIG. 49.

A variation of the implant discussed above is an implant 2200 with a six degree lordotic angle. FIG. 49, FIG. 50 and FIG. 51 illustrate the lordotic aspect of such as implant. FIG. 49 shows a front plan view of an implant 2200 with a six degree lordotic angle. The average height of the anterior connecting wall 2204 is greater than the average height of the posterior connecting wall 2208. FIG. 50 which is a rear plan view of the implant 2200 which shows that the anterior connecting wall 2204 has a greater height than the posterior connecting wall 2208. FIG. 51 shows a side view of the posterior wall 2208 with the larger anterior wall 2204 visible in the background. Other features for implant 2200 may be similar to implant 2000. If a cross bar is used, then the height may be constant or may vary from anterior to posterior.

Size Ranges.

The dimensions of the implants will be a function of the location of within the spine that receives the implant as the disc spaces get larger towards the lower portion of the spine. An implant intended for the L4/L5 disc space will tend to be larger for a given patient than an implant for the L1/L2 disc space. The dimensions of the implants will also be a function of the size of the patient as some patients have larger bones than other patients. Thus, the anterior to posterior dimension and the lateral dimension will vary based on the size of the relevant vertebral endplates. The height of the implant will be selected to match the surgeon's preference for the spacing of the two vertebrae after the surgical intervention. As noted above, there may be a lordotic angle of up to approximately twelve degrees. A summary of the range of typical dimensions for a lateral implant for the L1/L2, L2/L3, L3/L4 and L4/L5 disc spaces are summarized in the table below.

| Dimension | Range |
| --- | --- |
| Height | 7 mm to 17 mm (typically 7 mm to 15 mm) |
| Width | 17 mm to 26 mm |
| Length | 40 mm to 70 mm |
| Lordotic Angle | Zero to Twelve degrees (often six degrees) |

Coronal Wedge Implants.

Sometimes an implant varies in height in two ways. Thus rather than a simple lordotic implant, that varies from the anterior side of the disc to the posterior side of the disc, the implant may vary from the one lateral side of the disc to the other lateral side of the disc.

FIG. 52, FIG. 53, and FIG. 54 show the two aspects of variation for an oblique lordotic implant 2300. FIG. 52 is a front perspective view of an oblique lordotic implant 2300 shown without optional passages 2056 or the implant movement tool features (such as 2064 or 2096 discussed above). As shown in FIG. 53, the oblique lordotic implant 2300 grows from posterior side 2296 to anterior side 2292 and from the distal end 2088 to the proximal end 2082. The difference from posterior side 2296 to anterior side 2292 is approximately six degrees although other angles may be selected for particular applications. FIG. 54 is a side view that shows the growth from distal end 2088 to the proximal end 2082 (leading end to trailing end) at a slope approximated at four degrees although other angles may be chosen for particular situations. Note that as shown in FIG. 54, the growth in implant height is in both directions (cephalad and caudal) from the longitudinal centerline.

Implant Movement Tools.

The particulars of the tools for movement of the implant are beyond the focus of this application but implant movement tools include insertion tools, extraction tools, and tools that may be used for both purposes. An insertion tool may have a distal tip on a circular shaft such that the distal tip when properly aligned fits through the non-circular bore into the interior of the implant, possibly into the fusion cavity. Rotation of the distal tip of the implant tool results in a lack of alignment between the distal tip of the insertion tool and the non-circular bore so that the insertion tool remains engaged with the implant. Having at least one lateral engagement feature (such as 2096 discussed above) provides a second point of engagement with the insertion tool so that the implant is not free to rotate with respect to the insertion tool.

One of skill in the art will recognized that a rotated distal tip of an insertion tool that abuts an interior wall of the implant may be used to extract an implant. Force may be applied to the implant thought the use of a reverse slap hammer to enable the surgeon to remove an implant.

An alternative to a non-circular bore is a threaded bore that engages with a corresponding threaded tip of an implant movement device. The distal tip would rotate relative to the threaded bore. The implant would be precluded from rotating while the distal tip rotates relative to the implant as the implant movement device would be engaged with the implant via the lateral engagement feature (or more than one lateral engagement feature). This may be called a multi-point engagement.

Figure 55:
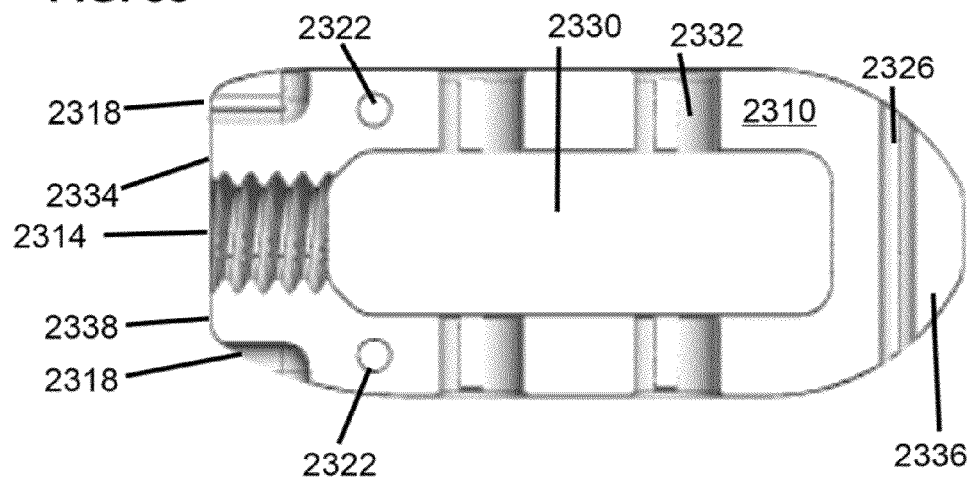
FIG. 55 shows a cross section of an implant that has a threaded bore and two lateral engagement features.

FIG. 55 shows an implant 2310 that has a threaded bore 2314 and two lateral engagement features 2318. The threaded bore 2314 in FIG. 55 connects the fusion cavity 2330 to a vertical face 2334 of the trailing end portion 2338. The implant 2310 shown in FIG. 55 does not have a cross bar as a cross bar is an optional aspect of an implant.

The implant 2310 in FIG. 55 uses a three rod marker system with two vertical rods 2322 near the trailing end portion 2338 and one horizontal rod 2326 in the leading end portion 2336.

Figure 56:
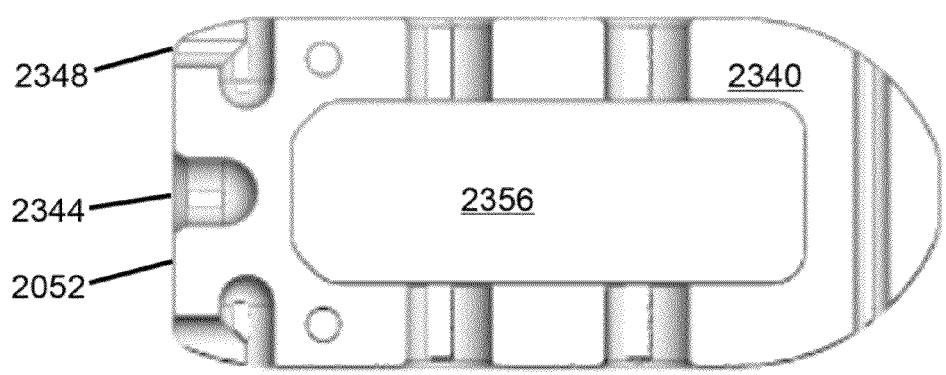
FIG. 56 shows a cross section of an implant that has a no-threaded bore and two lateral engagement features.
Figure 62:
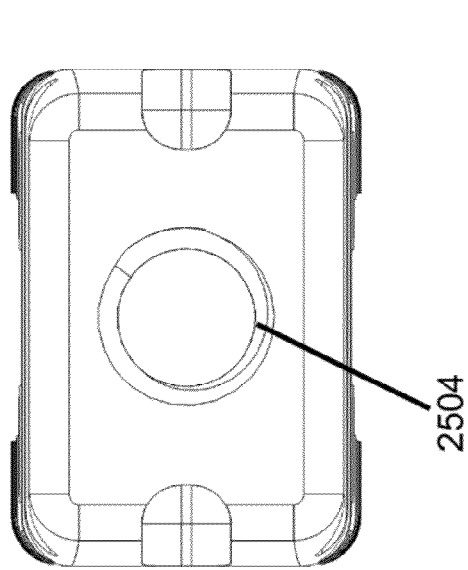
FIG. 62 is a rear view of the implant in FIG. 61.
Figure 64:
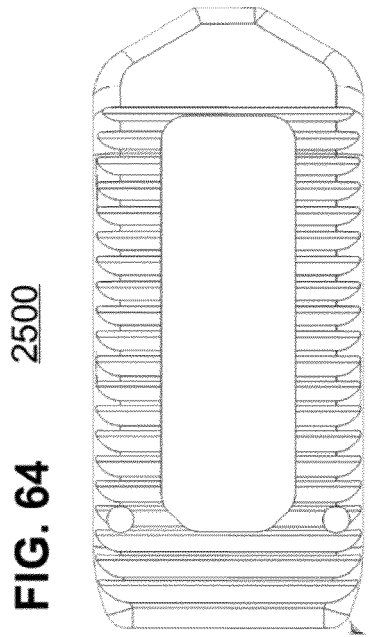
FIG. 64 is a top view of the implant in FIG. 61.
Figure 61:
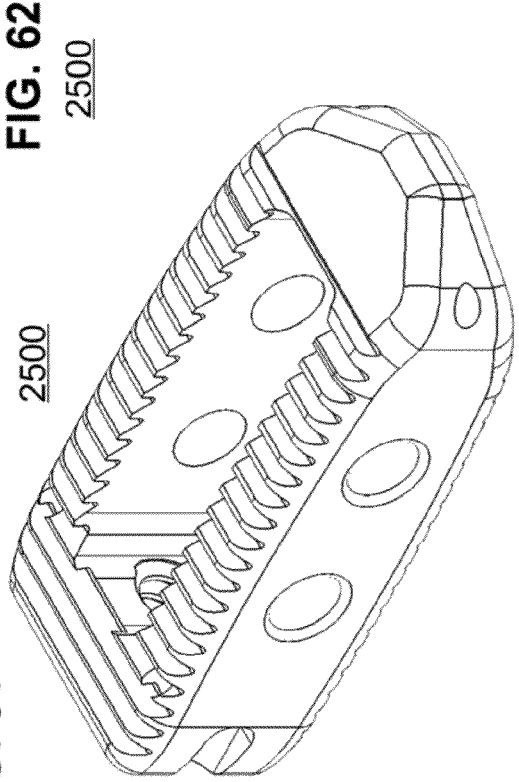
FIG. 61 is a front perspective view of an implant.
Figure 63:
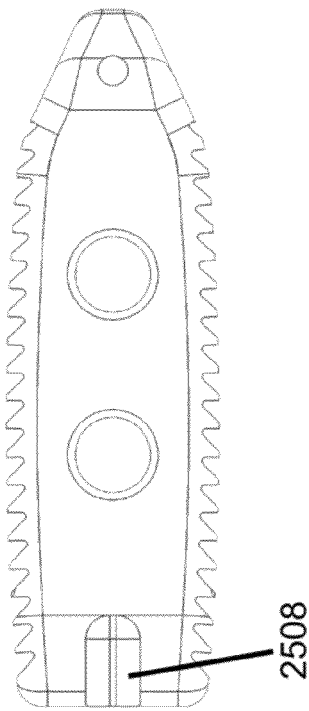
FIG. 63 is a side view of the implant in FIG. 61.
Figure 66:
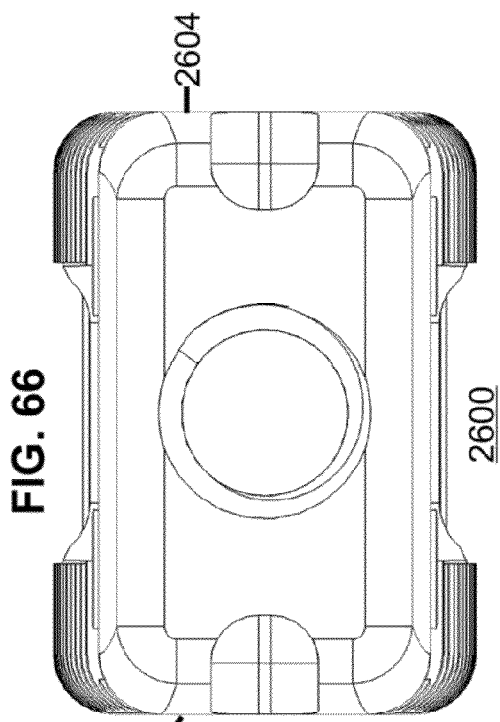
FIG. 66 is a rear view of the implant in FIG. 65.
Figure 68:
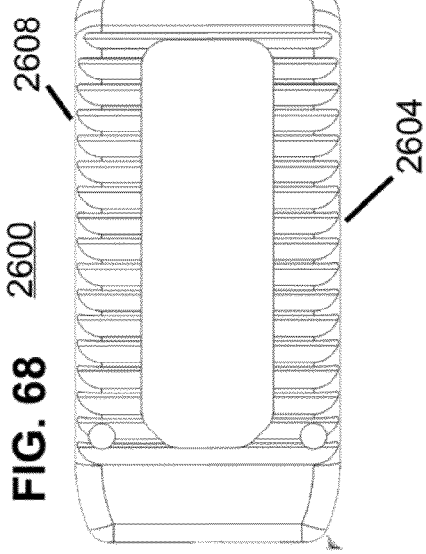
FIG. 68 is a top view of the implant in FIG. 65.
Figure 65:
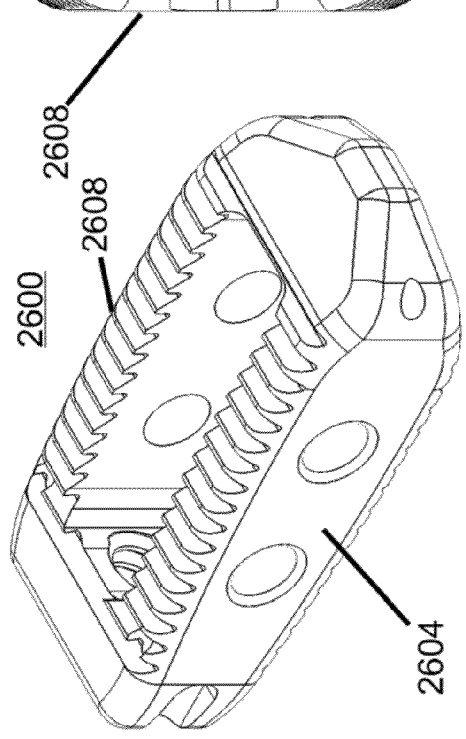
FIG. 65 is a front perspective view of an implant.
Figure 67:
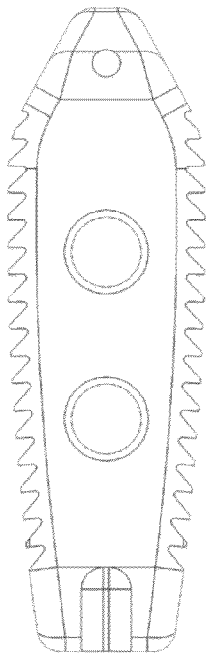
FIG. 67 is a side view of the implant in FIG. 65.

The implant 2340 in FIG. 56 is much like the implant 2310 in FIG. 55 except that the engagement with the implant movement tool is through a central bore 2344 and a pair of lateral engagement features 2348. An appropriate tool that squeezes the trailing edge portion 2052 of the implant 2340 between arms that engage the pair of lateral engagement features 2348 would have a firm grip on the implant 2340. Notice that the central bore 2344 is circular and does not extend through the trailing end portion 2352 to the fusion cavity 2356.

An extraction tool for removing an implant that has been present in a gap between two vertebrae long enough to have bone ingrowth into the fusion cavity may be made with a tap on the external end of the extraction tool to convert a non-threaded bore (including the central bore in the bow-tie shaped non-circular bore) into a tapped connection to allow large forces to be exerted on the implant to remove the implant from between the vertebrae.

Implants for TLIF or PLIF Access Routes.

While the bulk of this disclosure has addressed lateral approaches to a disc space, there are other access routes for access to the disc space. An approach from the posterior direction is known as the Posterior Lumbar Interbody Fusion or PLIF. Another related approach from the posterior is the Transforaminal Lumbar Interbody Fusion or TLIF. One difference between a TLIF and PLIF approach is the angle at which the disc is approached but both procedures are done through an incision in the patient's back. A difference in approach from a lateral approach as discussed above may require difference in the implants. Some implants may be adapted to be delivered via either a TLIF or PLIF approach.

Due to the posterolateral angle of approach in a TLIF, a TLIF implant is often inserted at an angle across the disc space. The angle is typically from the posterolateral corner of the disc entry to the anterior contralateral corner of the disc. Since the anterior part of the disc is taller in height than that the posterior part of the disc, it is beneficial to have a TLIF implant that matches the lordosis angle of the endplates for the path of insertion. Thus, it may be useful to have a substantially rectangular and asymmetric oblique-lordotic implant that is tallest at the leading corner closes the anterior side of the disc and progressively gets shorter on an angle towards the posterior lateral corner. The other two corners of the implant are at heights between the tallest corner and the shortest corner. An implant for a TLIF procedure may be designed to be inserted with the anti-migration features initially inserted in an anterior/posterior orientation before the implant is rotated to place the anti-migration features in their traditional cephalad/caudal orientation. This rotation of the implant may increase the distance between the cephalad and caudal vertebrae which is known as distraction. Distraction may decompress and alleviate spinal impingement on nerves.

The dimensions of a TLIF implant may be different than a lateral implant used for the same spinal level for the same patient as the approach route impacts the dimensions. A straight TLIF/PLIF implant will frequently have a height of between 7 to 17 mm, a width of 10 to 11 mm and a length of 23 to 35 mm. The lordotic angle will be 0 to 8 degrees.

Examples of Implants Adapted for Other Access Routes.

FIG. 57, FIG. 58, FIG. 59, and FIG. 60, show four view of an implant 2400 which has more height in the cephalad/caudal direction than width in the anterior/posterior direction. The implant 2400 has wedge shaped nose 2404 on the front end portion 2412. To facilitate placement within the available space within a disc space for an implant delivered via a particular access angle, the trailing end portion 2408 has a cut corner portion 2416 which could be placed on the posterior lateral portion of the disc space. This type of implant 2400 may be useful in a TLIF approach. The optional passages 2456 have elongated dimensions in the cephalad/caudal direction. The bore 2424 is threaded. The TLIF delivery route may encourage a design without stress concentrators so the design may choose as here to avoid a bowtie or other non-circular bore.

The marker set uses three rods 2428. The fusion cavity 2432 does not have the optional cross bar. Representative dimensions for implant 2400 are about 17 millimeters cephalad/caudal, about 10 millimeters width, and about 23 millimeters in length.

FIG. 61, FIG. 62, FIG. 63, and FIG. 64, show four view of an implant 2500. The implant 2500 uses a threaded bore 2504 and a pair of lateral engagement features 2508. The other features are self-documenting given the discussion of other implants already provided. Representative dimensions for implant 2500 are about 7 millimeters cephalad/caudal, about 10 millimeters width, and about 23 millimeters in length. Ranges for dimensions are about 7 to about 17 millimeters cephalad/caudal, about 10 millimeters width, and about 23 to about 35 millimeters in length.

FIG. 65, FIG. 66, FIG. 67, and FIG. 68, show four view of an implant 2600 that is similar in many ways to implant 2500. This implant may be used in a TLIF or PLIF procedure to provide an implant with a lordotic angle of approximately six degrees. Note that for an implant inserted from a posterior path, the anterior to posterior difference in cephalad/caudal height is done by varying the height of both connecting walls 2604, 2608 as there is not an anterior sidewall and a posterior sidewall as one would find via a lateral approach.

FIG. 69, FIG. 70, FIG. 71, and FIG. 72, show four view of a curved implant 2700. A curved implant 2700 may be an advantageous shape for certain access routes to the disc space. The marker set for curved implant 2700 is three vertical rods 2704, 2708, and 2712 with the rod 2712 for the cross bar being wider and shorter than the other two rods 2704 and 2708. Rod 2712 could be replaced with a different marker such as a sphere. Curved implant 2700 does not have passages through the connecting walls 2716 and 2720.

FIG. 73, FIG. 74, and FIG. 75 show three views of a curved implant 2800 that is similar to curved implant 2700 but has a different height/width aspect ratio compared with curved implant 2700 as curved implant 2700 is wider than it is tall (11 millimeters versus 6 millimeters). In contrast, curved implant 2800 is taller than it is wide (17 millimeters tall versus 11 millimeters wide). Curved implant 2800 differs from curved implant 2700 in that curved implant 2800 has a lordotic angle of about eight degrees. The lordotic angle is not as apparent as the lordotic angle in implants with less height, but the lordotic angle is visible in FIG. 74 as the anterior connecting wall 2804 is taller than the posterior connecting wall 2808.

One of skill in the art will recognize that a family of curved implants will likely have various combinations of implant height (as measured on the taller side) of about 6 millimeters to about 17 millimeters, length of about 27 millimeters to about 35 millimeters, or lordotic angle of zero degrees to about 8 degrees. These ranges may be different for different applications such as a different part of the spine or for a special population of patients.

Alternatives and Variations.

One of skill in the art will recognize that a channel retractor with a closed inner perimeter may be comprised of one or more components, even if none of the individual components placed in the patient tissue have a closed inner perimeter. Thus two or more U-shaped components could be attached in a way to allow use as a channel retractor.

While various channel retractors have been discussed above and these have used different channel shapes including round and oblong, other channel shapes could be used with appropriate modification to the other components that need to form an assembly with the channel retractor. A "D" shaped channel retractor is one possibility as are a variety of polygons.

Number of Extended Retractors.

While the examples discussed above frequently used two extended retractors, one of skill in the art will appreciate that other combinations are within the scope of this disclosure. For example, three or more extended retractors could be positioned to either create an enlarged opening in tissue distal to the distal end of the channel retractor or three or more extended retractors could be used to maintain an opening in tissue distal to the distal end of the channel retractor. The channel retractor may have a set of concavities equal to the number of extended retractors and the corresponding inner sleeve may have convex surfaces to push or maintain retractors into those concavities. For example, a three-lobed channel retractor may be used with a set of three extended retractors and a corresponding inner sleeve.

Alternatively, some surgeons may prefer to use a single extended retractor rather than two or more extended retractors. These surgeons may find it attractive to have a process that is biased to enlarge the opening in the tissue in one direction more than the other. For example, a surgeon may prefer to place a single extended retractor on the anterior side of a split created in the psoas muscle so that subsequent insertion of an inner sleeve or use of a jack assembly pushes the one extended retractor in the anterior direction to open the psoas muscle more in the anterior direction than in the posterior direction.

Extended Retractor Retention.

A tube in a tube type retractor system may use one of several adaptations in order to bias the extended retractors to stay in proximity with the inner perimeter of the proximal end of the channel retractor. The interaction between the slot in the handle and a rim protrusion as shown in FIG. 8 or the interaction between the handle protrusion and slot as shown in FIG. 13 will serve to bias the extended retractors to stay near the inner perimeter of the proximal end of the channel retractor. These two adaptations also limit the ability of the extended retractors to move around the circumference of the channel retractor. Some surgeons may prefer an extended tube retention adaptation that does not limit circumferential movement of the extended retractors.

One such adaptation is to use horizontal slots in the channel retractor rather than vertical slots. The use of extended retractors with protrusions with a channel retractor with a horizontal slot would allow a surgeon to temporarily place the extended retractor protrusion in the slot so that the extended retractor stays near the inner perimeter of the extended retractor while the second extended retractor is placed into the gap in the psoas muscle. The surgeon can engage a protrusion from the second extended retractor with a horizontal slot on the opposite side of the channel retractor to keep the second extended retractor near the inner perimeter of the channel retractor until an inner sleeve is inserted to hold the two extended retractors to the inner perimeter of the channel retractor. While one or more horizontal slots will allow the extended retractors to move some distance around the circumference of the inner perimeter of the channel retractor, the horizontal slots will not allow substantial movement in the proximal direction.

Another adaptation for retaining the extended retractors in against the inner perimeter of the proximal end of the channel retractor is the use of elongated shallow vertical slots cut into the channel retractor so that an extended retractor could be press fit into the elongated slot with little effort. This solution would serve to hold the extended retractor to the inner perimeter of the proximal end of the channel retractor and limit the ability of the extended retractor to move around the circumference of the channel retractor.

Another adaptation for retaining the extended retractors to the inner perimeter of the proximal end of the channel retractor is the use of magnets. Magnets imbedded in the channel retractor may engage magnetic materials used in making the intermediate or proximal portions of the channel retractor. The magnetic attraction may be increased by imbedding magnets in the intermediate or proximal portions of the extended retractors if the polarity of the magnetism can be managed. By managed, it would be important to avoid having like polarities between an extended retractor and a corresponding magnet for the channel retractor as that would tend to push the extended retractor away from the inner perimeter of the channel retractor.

Another adaptation for retaining the extended retractors in engagement with the inner perimeter of the proximal end of the channel retractor is the use of clips on the extended retractors to allow a quick connection to the proximal end of the channel retractor. Yet another adaptation for retaining the extended retractors to the inner perimeter of the proximal end of the channel retractor is the use of clips on the channel retractor to quickly connect to an extended retractor to retain the extended retractor to the inner perimeter of the distal end of the channel retractor.

Neuromonitoring.

While the techniques set forth above allow access through the psoas muscle without the use of neuromonitoring, a surgeon may opt to add neuromonitoring in order to provide an additional method for avoiding nerve trauma from dilators.

Other Integrated Lights.

The disclosure teaches the use of a stadium light or a variety of lighting options using the various configurations of inner sleeves. One of skill in the art will recognize that the light could be integrated within the channel retractor rather than the inner sleeve. Thus light would travel through at least a portion of channel retractor between the inner perimeter and an outer perimeter. While it is likely that the light would be provided to a portion of the channel retractor that extends outside of the patient, this is not required. As with the inner sleeve, fiber optic fibers could be used so that one or more relatively narrow entrance paths into the channel retractor could provide light for a substantial fraction (possibly all) of the distal perimeter of the channel retractor. Likewise one of skill in the art will recognize that the light does not have to be emitted from the distal ends of the channel retractor of the inner sleeve but could be emitted on an angle partway down the channel retractor or inner sleeve to direct light to the tissue distal to the channel retractor.

One of skill in the art will recognize that a component may emit light that is provided to the component through a light channel of some type, or the component may emit light created within the component.

Camera Use.

The disclosure teaches that lights can be placed along a proximal rim at the proximal end of the channel retractor, integrated with the inner sleeve (including inner sleeves that emit light along a distal end), or integrated with the channel retractor. These same locations may be used to position one or more cameras including cameras providing real time video imaging of the surgical procedure including the tissue beyond the opening at the distal end of the channel retractor. The camera may include a lighting source or may rely on lighting from another source.

Multi-Level Surgery.

While for convenience, the description set forth above focused on providing therapy to a single motion segment (one disc space between two adjacent vertebrae), one of skill in the art will recognize that the process set forth above may be repeated so that more than one motion segment receives therapy (such as fusion) during a single surgical intervention.

Cross Bars.

One of skill in the art will recognize that instead of one cross bar, an implant may have two or more cross bars. As noted above, the cross bar is optional and the implant may not have a cross bar at all. While there is an advantage of having space above and below a cross bar for fusion promoting materials, an implant may be made with a cross bar that forms part of the first vertebral surface or the second vertebral surface or both. The cross bar may include the anti-migration feature if the cross bar is part of a vertebral surface of an implant.

Open Surgery.

While the focus of this disclosure has been on a minimally invasive lateral access approach to the disc space, the various implants described in this application may be used with other access routes including open surgery rather than a minimally invasive approach.

Kits.

One of skill in the art will recognize that the surgical procedures set forth above may benefit from various kits of tools and components for use in these procedures. Kits may focus on reusable or disposable components for creating an access route. Other kits may focus on the tools for preparing the disc space. A kit may include many (possibly even all) the components necessary for a particular procedure including the components needed to create the access route, prepare the disc space and even the an assortment of implants.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art. Individual claims may be tailored to claim particular embodiments out of the array of embodiments disclosed above. Some claims may be tailored to claim alternative embodiments rather than preferred embodiments. Some claims may cover an embodiment set forth above with a modification from another embodiment as the present disclosure does not include drawings of all possible combinations of feature sets.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. An implant for positioning in a motion segment between a cephalad vertebra and caudal vertebra, the implant comprising:
   a trailing edge portion that may be engaged by an implant movement tool; the trailing edge portion includes:
      at least one non-circular bore that engages with the implant movement tool for movement; and
      at least one lateral engagement feature which is non-contiguous with the at least one non-circular bore such that the tool for movement of the implant can engage the at least one non-circular bore and the at least one lateral engagement feature to provide a multi-point engagement with the tool for movement of the implant;
   a leading edge portion on an opposite side of the implant from the trailing edge portion;
   a first connecting wall connecting the leading edge portion to the trailing edge portion;
   a second connecting wall with a height greater than the first connecting wall connecting the leading edge portion to the trailing edge portion, the leading edge portion, trailing edge portion, and first and second connecting walls forming a perimeter frame around a fusion cavity;
   a first vertebral side;
   a second vertebral side; and
   the leading edge portion having a leading vertical face, which is a small end of a quadrilateral pyramidal frusta with rounded edges that extends a set of four sloped faces from the leading vertical face to the first connecting wall, second connecting wall, first vertebral side, and second vertebral side;
   wherein the quadrilateral pyramidal frusta for the leading edge portion has a leading edge of the sloped face of the first vertebral side that is not parallel to a leading edge of the sloped face for the second vertebral side;
   wherein the trailing edge portion has a trailing vertical face which is a small end of a quadrilateral pyramidal frusta with rounded edges that extends a set of four sloped faces from the trailing vertical face to the first connecting wall, second connecting wall, first vertebral, and second vertebral side;
   wherein the quadrilateral pyramidal frusta for the trailing edge portion has a trailing edge of the sloped face of the first vertebral side that is not parallel to a trailing edge of the sloped face for the second vertebral side;
   wherein the first connecting wall is connected to the second connecting wall through the trailing edge portion, the leading edge portion, and at least one cross bar; and
   the implant is made from a material that is much less radio-opaque than a set of markers placed in the implant, including a marker in the at least one crossbar so that implant orientation may be discerned by fluoroscopy.

2. The implant of claim 1 wherein:
   the first vertebral side that comprises:
      a part of a first side of the leading edge portion;
      a part of a first side of the trailing edge portion;
      a first side of the first connecting wall; and
      a first side of the second connecting wall; and
   the second vertebral side that comprises:
      a part of a first side of the leading edge portion;
      a part of a second side of the trailing edge portion;
      a second side of the first connecting wall; and
      a second side of the second connecting wall; and
   wherein the first vertebral side and the second vertebral side have anti-migration features adapted to resist movement of the implant towards the trailing edge more than movement of the implant towards the leading edge and the anti-migration features are present on the leading edge portion between the first connecting wall and the second connecting wall and on the trailing edge portion between the first connecting wall and the second connecting wall.

3. An implant for positioning in a motion segment between a cephalad vertebra and caudal vertebra, the implant comprising:
   a trailing edge portion that may be engaged by an implant movement tool;
   a leading edge portion on an opposite side of the implant from the trailing edge portion;
   a first connecting wall connecting the leading edge portion to the trailing edge portion;
   a second connecting wall connecting the leading edge portion to the trailing edge portion;
   a perimeter frame around a fusion cavity including the leading edge portion, the trailing edge portion, the first connecting wall and the second connecting wall;
   a first vertebral side;
   a second vertebral side; and
   the leading edge portion having a leading vertical face which may be advanced into tissue without tissue engaging an interior of the implant through the leading edge portion, the leading edge portion being a small end of a quadrilateral pyramidal frusta with rounded edges that extends a set of four sloped faces from the leading vertical face to the first connecting wall, second connecting wall, first vertebral side, and second vertebral side;
   wherein the quadrilateral pyramidal frusta for the leading edge portion has a leading edge of the sloped face of the first vertebral side that is not parallel to a leading edge of the sloped face for the second vertebral side;
   wherein the trailing edge portion has a trailing vertical face which is a small end of a quadrilateral pyramidal frusta with rounded edges that extends a set of four sloped faces from the trailing vertical face to the first connecting wall, second connecting wall, first vertebral side, and second vertebral side;
   wherein the quadrilateral pyramidal frusta for the trailing edge portion has a trailing edge of the sloped face of the first vertebral side that is not parallel to a trailing edge of the sloped face for the second vertebral side;
   wherein the first connecting wall is connected to the second connecting wall through the trailing edge portion, the leading edge portion, and at least one cross bar; and
   the implant is made from a material that is much less radio-opaque than a set of markers placed in the implant, including a marker in the at least one crossbar so that implant orientation may be discerned by fluoroscopy.

4. The implant of claim 3 wherein:
   the first vertebral side that comprises:
      a part of a first side of the leading edge portion;
      a part of a first side of the trailing edge portion;
      a first side of the first connecting wall; and
      a first side of the second connecting wall; and
   the second vertebral side that comprises:
      a part of a first side of the leading edge portion;
      a part of a second side of the trailing edge portion;
      a second side of the first connecting wall; and
      a second side of the second connecting wall; and
   wherein the first vertebral side and the second vertebral side have anti-migration features adapted to resist movement of the implant towards the trailing edge more than movement of the implant towards the leading edge and the anti-migration features are present on the leading edge portion between the first connecting wall and the second connecting wall and on the trailing edge portion between the first connecting wall and the second connecting wall.

5. The implant of claim 3 wherein the trailing edge portion includes:
   at least one non-circular bore that engages with the implant movement tool for movement; and
   at least one lateral engagement feature, separate from the non-circular bore, such that the tool for movement of the implant can engage the at least one non-circular bore and the at least one lateral engagement feature to provide a multi-point engagement with the tool for movement of the implant.

6. An implant for positioning in a motion segment between a cephalad vertebra and a caudal vertebra, the implant comprising:
   a trailing edge portion that may be engaged by an implant movement tool;
   a leading edge portion on an opposite side of the implant from the trailing edge portion;
   a first connecting wall connecting the leading edge portion to the trailing edge portion;
   a second connecting wall connecting the leading edge portion to the trailing edge portion wherein the leading edge portion, the trailing edge portion, the first connecting wall, and the second connecting wall form a perimeter frame around a fusion cavity;
   the first connecting wall is connected to the second connecting wall through the trailing edge portion, the leading edge portion, and at least one cross bar;
   the implant having a set of four markers located in each of a set of four intersections of the trailing edge portion with the first connecting wall and the second connecting wall, and the leading edge portion and the first connecting wall and the second connecting wall such that a failure of two of the markers to line up at either corner connecting the leading edge portion indicates a lack of alignment with a fluoroscopic view; and
   a cross bar marker may be used to center the implant with respect to a spinous process as the cross bar marker is half way between a leading edge of the implant and a trailing edge of the implant;
   wherein the leading edge portion has a leading vertical face which is a small end of a quadrilateral pyramidal frusta with rounded edges that extends a set of four sloped faces from the leading vertical face to the first connecting wall, the second connecting wall, a first vertebral side, and a second vertebral side; and
   wherein the quadrilateral pyramidal frusta for the leading edge portion has a leading edge of the sloped face of the first vertebral side that is not parallel to a leading edge of the sloped face for the second vertebral side;
   wherein the trailing edge portion has a trailing vertical face which is a small end of a quadrilateral pyramidal frusta with rounded edges that extends a set of four sloped faces from the trailing vertical face to the first connecting wall, the second connecting wall, the first vertebral side, and the second vertebral side; and
   wherein the quadrilateral pyramidal frusta for the trailing edge portion has a trailing edge of the sloped face of the first vertebral side that is not parallel to a trailing edge of the sloped face for the second vertebral side.

7. The implant of claim 6 wherein:
   the first vertebral side that comprises:
      a part of a first side of the leading edge portion;
      a part of a first side of the trailing edge portion;
      a first side of the first connecting wall; and
      a first side of the second connecting wall; and
   the second vertebral side that comprises:
      a part of a first side of the leading edge portion;
      a part of a second side of the trailing edge portion;
      a second side of the first connecting wall; and
      a second side of the second connecting wall; and
   wherein the first vertebral side and the second vertebral side have anti-migration features adapted to resist movement of the implant towards the trailing edge more than movement of the implant towards the leading edge and the anti-migration features are present on the leading edge portion between the first connecting wall and the second connecting wall and on the trailing edge portion between the first connecting wall and the second connecting wall.

8. The implant of claim 6 wherein the trailing edge portion includes:
   at least one non-circular bore that engages with the implant movement tool for movement; and
   at least one lateral engagement feature, separate from the non-circular bore, such that the tool for movement of the implant can engage the at least one non-circular bore and the at least one lateral engagement feature to provide a multi-point engagement with the tool for movement of the implant.

\* \* \* \* \*